(12) United States Patent
Ab et al.

(10) Patent No.: US 9,133,275 B2
(45) Date of Patent: *Sep. 15, 2015

(54) FOLATE RECEPTOR 1 ANTIBODIES AND IMMUNOCONJUGATES AND USES THEREOF

(71) Applicant: ImmunoGen, Inc., Waltham, MA (US)

(72) Inventors: Olga Ab, Millis, MA (US); Daniel Tavares, Natick, MA (US); Lingyun Rui, Weston, MA (US); Gillian Payne, Waban, MA (US); Viktor S. Goldmakher, Newton, MA (US)

(73) Assignee: ImmunoGen, Inc., Waltham, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 13/800,835

(22) Filed: Mar. 13, 2013

(65) Prior Publication Data

US 2013/0295119 A1 Nov. 7, 2013

Related U.S. Application Data

(62) Division of application No. 13/033,723, filed on Feb. 24, 2011, now Pat. No. 8,557,966.

(60) Provisional application No. 61/307,797, filed on Feb. 24, 2010, provisional application No. 61/346,595, filed on May 20, 2010, provisional application No. 61/413,172, filed on Nov. 12, 2010.

(51) Int. Cl.
*A61K 39/395* (2006.01)
*A61K 39/00* (2006.01)
*C07K 16/30* (2006.01)
*A61K 47/48* (2006.01)
*C07K 16/28* (2006.01)
*A61K 45/06* (2006.01)

(52) U.S. Cl.
CPC ....... *C07K 16/3069* (2013.01); *A61K 39/39558* (2013.01); *A61K 45/06* (2013.01); *A61K 47/48384* (2013.01); *A61K 47/48407* (2013.01); *A61K 47/48561* (2013.01); *C07K 16/28* (2013.01); *C07K 2317/24* (2013.01); *C07K 2317/732* (2013.01)

(58) Field of Classification Search
None
See application file for complete search history.

(56) References Cited

U.S. PATENT DOCUMENTS

| 5,416,016 | A | 5/1995 | Low et al. |
|---|---|---|---|
| 5,720,954 | A | 2/1998 | Hudziak et al. |
| 5,855,866 | A | 1/1999 | Thorpe et al. |
| 6,051,230 | A | 4/2000 | Thorpe et al. |
| 7,033,594 | B2 | 4/2006 | Low et al. |
| 7,112,317 | B2 | 9/2006 | Thorpe et al. |
| 7,125,541 | B2 | 10/2006 | Thorpe et al. |
| 7,740,854 | B2 | 6/2010 | Low et al. |
| 8,557,966 | B2 | 10/2013 | Ab et al. |
| 2003/0028009 | A1 | 2/2003 | Huse |
| 2003/0148406 | A1 | 8/2003 | King et al. |
| 2003/0157090 | A1 | 8/2003 | Benvenuto et al. |
| 2003/0229208 | A1 | 12/2003 | Queen et al. |
| 2003/0233675 | A1 | 12/2003 | Cao et al. |
| 2004/0031072 | A1 | 2/2004 | La Rosa et al. |
| 2004/0087478 | A1 | 5/2004 | Gillen et al. |
| 2004/0157214 | A1 | 8/2004 | McCafferty et al. |
| 2004/0170630 | A1 | 9/2004 | Huang et al. |
| 2004/0180386 | A1 | 9/2004 | Carr et al. |
| 2004/0235840 | A1 | 11/2004 | Chari et al. |
| 2005/0025763 | A1 | 2/2005 | Williams et al. |
| 2005/0244901 | A1 | 11/2005 | Peschen et al. |
| 2006/0030524 | A1 | 2/2006 | Cohen et al. |
| 2006/0110771 | A1 | 5/2006 | Katagiri et al. |
| 2006/0228349 | A1 | 10/2006 | Acton et al. |
| 2006/0239910 | A1 | 10/2006 | Nicolaides et al. |
| 2007/0041985 | A1 | 2/2007 | Unger et al. |
| 2007/0098719 | A1 | 5/2007 | Smith et al. |
| 2007/0099251 | A1 | 5/2007 | Zhang et al. |
| 2007/0231266 | A1 | 10/2007 | Low et al. |
| 2007/0294782 | A1 | 12/2007 | Abad et al. |
| 2008/0081047 | A1 | 4/2008 | Berry et al. |
| 2008/0104734 | A1 | 5/2008 | Kav et al. |
| 2008/0138396 | A1 | 6/2008 | Low et al. |
| 2008/0181888 | A1 | 7/2008 | Ambrose et al. |
| 2008/0227704 | A1 | 9/2008 | Kamens |
| 2008/0260748 | A1 | 10/2008 | Iwamoto et al. |
| 2009/0081710 | A1 | 3/2009 | Low et al. |
| 2009/0104215 | A1 | 4/2009 | Ekiel et al. |
| 2009/0136516 | A1 | 5/2009 | Tedder et al. |
| 2009/0169547 | A1 | 7/2009 | Sahin et al. |
| 2009/0186027 | A1 | 7/2009 | Solomon et al. |

(Continued)

FOREIGN PATENT DOCUMENTS

| CN | 101139613 A | 3/2008 |
|---|---|---|
| CN | 101440130 A | 5/2009 |

(Continued)

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*

(Continued)

*Primary Examiner* — Hong Sang
(74) *Attorney, Agent, or Firm* — Sterne, Kessler, Goldstein & Fox PLLC

(57) ABSTRACT

Novel anti-cancer agents, including, but not limited to, antibodies and immunoconjugates, that bind to human folate receptor 1 are provided. Methods of using the agents, antibodies, or immunoconjugates, such as methods of inhibiting tumor growth are further provided.

44 Claims, 21 Drawing Sheets

(56) References Cited

U.S. PATENT DOCUMENTS

Figure 3:
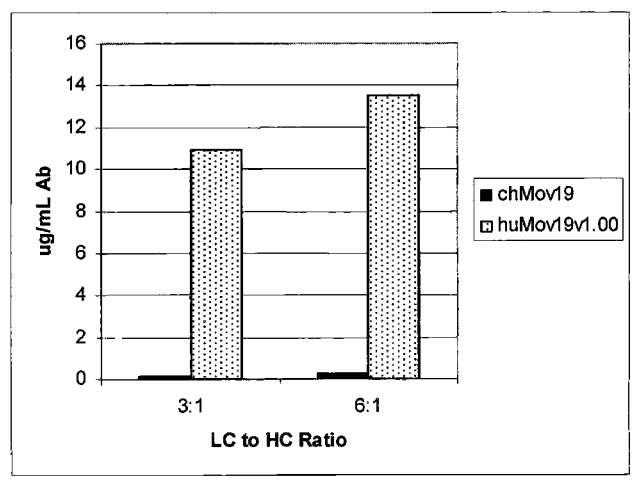

| | | |
|---|---|---|
| 2009/0214636 A1 | 8/2009 | Low et al. |
| 2009/0215165 A1 | 8/2009 | Rance et al. |
| 2009/0232822 A1 | 9/2009 | Joseloff et al. |
| 2009/0274697 A1 | 11/2009 | Grasso et al. |
| 2009/0274713 A1 | 11/2009 | Chari et al. |
| 2009/0280124 A1 | 11/2009 | Labat et al. |
| 2009/0280128 A1 | 11/2009 | Kamogawa et al. |
| 2009/0285795 A1 | 11/2009 | Patell |
| 2009/0285813 A1 | 11/2009 | Frey et al. |
| 2009/0317921 A1 | 12/2009 | Groome et al. |
| 2009/0324491 A1 | 12/2009 | Aburatani et al. |
| 2009/0324594 A1 | 12/2009 | Nicolaides et al. |
| 2010/0055034 A1 | 3/2010 | Martin et al. |
| 2010/0086537 A1 | 4/2010 | Sooknanan et al. |
| 2010/0087509 A1 | 4/2010 | Van Rompaey et al. |
| 2010/0104626 A1 | 4/2010 | Leamon et al. |
| 2010/0111852 A1 | 5/2010 | Yoshida |
| 2010/0111866 A1 | 5/2010 | Kratz |
| 2010/0129314 A1 | 5/2010 | Singh et al. |
| 2010/0239581 A1 | 9/2010 | Joseloff et al. |
| 2010/0255479 A1 | 10/2010 | Mikolajczyk et al. |
| 2010/0272741 A1 | 10/2010 | Knutson et al. |
| 2010/0323973 A1 | 12/2010 | Leamon et al. |
| 2010/0330572 A1 | 12/2010 | Assaraf et al. |
| 2011/0059469 A1 | 3/2011 | Aburatani et al. |
| 2011/0195022 A1 | 8/2011 | Deckert et al. |
| 2012/0177664 A1 | 7/2012 | Yokoseki et al. |
| 2012/0183552 A1 | 7/2012 | Joseloff et al. |
| 2012/0207771 A1 | 8/2012 | O'Shannessy et al. |
| 2012/0253021 A1 | 10/2012 | Li et al. |
| 2012/0259100 A1 | 10/2012 | Jin |
| 2012/0282175 A1 | 11/2012 | Carrigan et al. |
| 2012/0282282 A1 | 11/2012 | Lutz et al. |
| 2014/0099332 A1 | 4/2014 | Testa et al. |
| 2014/0363451 A1 | 12/2014 | Running et al. |

FOREIGN PATENT DOCUMENTS

| | | |
|---|---|---|
| EP | 1 900 752 A1 | 3/2008 |
| EP | 1 864 133 B1 | 3/2010 |
| WO | WO 94/29351 A2 | 12/1994 |
| WO | WO 97/11971 A1 | 4/1997 |
| WO | WO 02/071928 A2 | 9/2002 |
| WO | WO 2004/110498 A1 | 12/2004 |
| WO | WO 2005/003154 A2 | 1/2005 |
| WO | WO 2005/080431 A2 | 9/2005 |
| WO | WO 2006/105141 A1 | 10/2006 |
| WO | WO 2006/116592 A2 | 11/2006 |
| WO | WO 2007/006041 A2 | 1/2007 |
| WO | WO 2007/094754 A2 | 8/2007 |
| WO | WO 2007/147265 A1 | 12/2007 |
| WO | WO 2008/021290 A2 | 2/2008 |
| WO | WO 2008/031577 A1 | 3/2008 |
| WO | WO 2008/072723 A1 | 6/2008 |
| WO | WO 2008/101231 A2 | 8/2008 |
| WO | WO 2008/145136 A1 | 12/2008 |
| WO | WO 2009/080759 A1 | 7/2009 |
| WO | WO 2009/087978 A1 | 7/2009 |
| WO | WO 2009/132081 A2 | 10/2009 |
| WO | WO 2010/033733 A1 | 3/2010 |
| WO | WO 2010/111388 A2 | 9/2010 |
| WO | WO/2012/135675 A2 | 10/2012 |
| WO | WO/2012/138749 A1 | 10/2012 |
| WO | WO 2014/186403 A2 | 11/2014 |

OTHER PUBLICATIONS

Chen et al., Current Drug Delivery, 2004, 1(4): 361-376.*

Final Office Action, mailed Dec. 12, 2013, in U.S. Appl. No. 13/435,857, filed Mar. 30, 2012.

International Search Report in International Application No. PCT/US2013/057682, International Searching Authority, United States, Alexandria, VA mailed Jan. 10, 2014.

Ab, O., et al., "Antibody-Maytansinoid Conjugates Targeting Folate Receptor 1 for Cancer Therapy," *2010 EORTC-NCI-AACR Symposium*—Berlin, Germany (Nov. 16-19, 2010), Abstract 236, 1 Page, American Association for Cancer Research, Germany (distributed in print Nov. 16, 2010; available online Oct. 29, 2010).

Ab, O., et al., "IMGN853, an anti-Folate Receptor I antibody-maytansinoid conjugate for targeted cancer therapy," *102nd Annual AACR Meeting*—Orlando, FL (Apr. 2-6, 2011), Abstract 4576, 1 Page, American Association for Cancer Research, United States (distributed on print Mar. 8, 2011; available online Feb. 25, 2011).

Ab, O., et al., "IMGN853, an anti-Folate Receptor I antibody-maytansinoid conjugate for targeted cancer therapy," *102nd Annual AACR Meeting*—Orlando, FL (Apr. 2-6, 2011), Abstract 4576 Poster, American Association for Cancer Research, United States (Apr. 2, 2011).

Carrigan, C.N., et al., "Evaluation of Folate Receptor 1 (FOLR1) expression by calibrated immunohistochemistry identifies candidate tumor subtypes for targeting by IMGN853, an anti-FOLR1-maytansinoid conjugate," *102nd Annual AACR Meeting*—Orlando, FL (Apr. 2-6, 2011), Abstract 3617, 1 Page, American Association for Cancer Research, United States (distributed on print Mar. 8, 2011; available online Feb. 25, 2011).

Carrigan, C.N., et al., "Evaluation of Folate Receptor 1 (FOLR1) Expression by Calibrated Immunohistochemistry Identifies Candidate Tumor Subtypes for Targeting by IMGN853, an Anti-FOLR1-Maytansinoid Conjugate," *102nd Annual AACR Meeting*—Orlando, FL (Apr. 2-6, 2011), Abstract 3617 Poster, American Association for Cancer Research, United States (Apr. 2, 2011).

Chen, J., et al., "Antibody-cytotoxic agent conjugates for cancer therapy," *Expert Opin. Drug Deliv.* 2(5):873-890, Ashley Publications, England (2005).

Singh, R. and Erickson, H.K., "Antibody-Cytotoxic Agent Conjugates: Preparation and Characterization," in *Therapeutics Antibodies: Methods and Protocols* vol. 525, Dimitrov, A.S., ed., pp. 445-467, Humana Press, United States (2009).

Whiteman, K.R., et al., "Preclinical evaluation of IMGN853, an anti-FOLR1 antibody-maytansinoid conjugate as a potential therapeutic for ovarian cancer," *102nd Annual AACR Meeting*—Orlando, FL (Apr. 2-6, 2011), Abstract 1760, 1 Page, American Association for Cancer Research, United States (distributed in print Mar. 8, 2011; available online Feb. 25, 2011).

Whiteman, K.R., et al., "Preclinical evaluation of IMGN853, an anti-FOLR1 antibody-maytansinoid conjugate, as a potential therapeutic for ovarian cancer," *102nd Annual AACR Meeting*—Orlando, FL (Apr. 2-6, 2011), Abstract 1760 Poster, American Association for Cancer Research, United States (Apr. 2, 2011).

Yuan, Y., et al., "Expression of the folate receptor genes *FOLR1* and *FOLR3* differentiates ovarian carcinoma from breast carcinoma and malignant mesothelioma in serious effusions,"*Human Pathology* 40:1453-1460, Elsevier Inc., United States (2009).

Supplementary European Search Report for European Application No. EP 11748067.3, The Hague, Netherlands, dated Jun. 26, 2013.

International Preliminary Report on Patentability, mailed Oct. 10, 2013, in International application No. PCT/US2012/031544, filed Mar. 30, 2012.

International Preliminary Report on Patentability, mailed Oct. 17, 2013, in International application No. PCT/US2012/032155, filed Apr. 4, 2012.

Non-Final Office Action, mailed Apr. 2, 2013, in U.S. Appl. No. 13/435,857, filed Mar. 30, 2012.

Non-Final Office Action, mailed Oct. 11, 2013, in U.S. Appl. No. 13/439,493, filed Apr. 4, 2012.

Co-pending, U.S. Appl. No. 14/015,653 inventors Testa N.E., et al., filed August. 30, 2013 (Not Published).

Armstrong, D.K., et al., "Exploratory phase II efficacy study of MORAb-003, a monoclonal antibody against folate receptor alpha, in platinum-sensitive ovarian cancer in first relapse," *J. Clin. Oncol. Suppl.* 26:293s, American Society of Clinical Oncology, United States (May 2008).

Conde, F.P., et al., "The *Aspergillus* toxin restrictocin is a suitable cytotoxic agent for generation of immunoconjugates with monoclonal antibodies directed against human carcinoma cells," *Eur. J. Biochem.* 178:795-802, Federation of European Biochemical Societies, United Kingdom (1989).

(56) References Cited

OTHER PUBLICATIONS

Coney, L.R., et al., "Chimeric Murine-Human Antibodies Directed against Folate Binding Receptor Are Efficient Mediators of Ovarian Carcinoma Cell Killing," *Cancer Res.* 54:2448-2455, American Association for Cancer Research, United States (May 1994).

Coney, L.R., et al., "Cloning of a Tumor-associated Antigen: MOv18 and MOv19 Antibodies Recognize a Folate-binding Protein," *Cancer Res.* 51:6125-6132, American Association for Cancer Research, United States (Nov. 1991).

Ebel, W., et al. "Preclinical evaluation of MORAb-003, a humanized monocolonal antibody antagonoizing folate receptor-alpha," *Cancer Immunon.* 7:6-13, Luigi Grasso, United States (Mar. 2007).

Ferrini, S., et al., "Bispecific monoclonal antibodies directed to CD16 and to a tumor-associated antigen induce target-cell lysis by resting NK cells and by a subset of NK clones," *Int. J. Cancer* 48:2247-233, Wiley-Liss, Inc., United States (1991).

Ferrini, S., et al., "Retargeting of T-cell-receptor gamma/delta+ lymphocytes against tumor cells by bispecific monoclonal antibodies. Induction of cytolytic activity and lymphokine production," *Int. J. Cancer Suppl.* 4:53-55, Alan R. Liss, Inc., United States (1989).

Gould H.J., et al., "Comparison of IgE and IgG antibody-dependent cytotoxicity in vitro and in a SCID mouse xenograft model of ovarian carcinoma," *Eur. J. Immunol.* 29:3527-3537, Wiley-VCH Verlag GmbH, Germany (1999).

Karagiannis, S. N., et al., "IgE-Antibody-Dependent Immunotherapy of Solid Tumors: Cytotoxic and Phagocytic Mechanisms of Eradication of Ovarian Cancer Cells," *J. Immunol.* 179:2832-2843, American Association of Immunologists, United States (Sep. 2007).

Melani, C., et al., "Targeting of Interleukin 2 to Human Ovarian Carcinoma by Fusion with a Single-Chain Fv of Antifolate Receptor Antibody," *Cancer Res.* 58:4146-4154, American Association for Cancer Research, United States (Sep. 1998).

Mezzanzanica, D., et al., "Human ovarian carcinoma lysis by cytotoxic T cells targeted by bispecific monoclonal antibodies: analysis of the antibody components," *Int. J. Cancer* 41:609-615, Alan R, Liss, Inc., United States (1988).

Miotti, S., et al., "Characterization of human ovarian carcinoma-associated antigens defined by novel monoclonal antibodies with tumor-restricted specificity," *Int. J. Cancer* 39:297-303, Alan R, Liss, Inc., United States (1987).

Smith-Jones, P.M., et al., "Preclinical Radioimmunotargeting of Folate Receptor Alpha using the Monoclonal Antibody Conjugate DOTA-MORAb-003," *Nucl. Med. Biol.* 35(3):343-351, Elsevier, United States (Apr. 2008).

Widdison, W.C., et al., "Semisynthetic Maytansine Analogues for the Targeted Treatment of Cancer,"*J. Med. Chem.* 49:4392-4408, American Chemical Society, United States (2006).

Zacchetti, A., et al., "$^{177}$Lu-labeled MOv18 as compared to $^{131}$I- or $^{90}$Y-labeled MOv18 has the better therapeutic effect in eradication of alpha folate receptor-expressing tumor xenografts," *Nucl. Med. Biol.* 36:759-770, Elsevier Inc., United States (2009).

International Search Report for International Application No. PCT/US2011/26079, International Searching Authority, United States, mailed on Aug. 2, 2011.

Armstrong, D.K., et al., "Efficacy and safety of farletuzumab, a humanized monoclonal antibody to folate receptor alpha, in platinum-sensitive relapsed ovarian cancer subjects: preliminary data from a phase-2 study," *Eur. J. Cancer Suppl.* 7:450, Elsevier Science Ltd., England (2009).

Nishiyama, T., et al., "A9SZW6 (A9SZW6_PHYPA) Unreviewed, UniProtKB/TrEMBL," UniProt, 3 pages, last modified Sep. 21, 2011, accessed at <http://www.uniprot.org/uniprot/A9SZW6>.

Copeland, A., et al., "B1G510 (B1G510_9BURK) Unreviewed, UniProtKB/TrEMBL," UniProt, 3 pages, last modified Dec. 14, 2011, accessed at <http://www.uniprot.org/uniprot/B1G510>.

Lim, J., et al., "C5A929 (C5A929_BURGB) Unreviewed, UniProtKB/TrEMBL", UniProt, 4 pages, last modified Apr. 18, 2012, accessed at <http://www.uniprot.org/C5A929>.

English language Abstract of Chinese Patent Publication No. CN 101139613A European Patent Office, espacenet database—Worldwide, (2012) (listed as document FP4 on the accompanying form PTO/SB/08A).

English language Abstract of Chinese Patent Publication No. CN 101440130A, European Patent Office, espacenet database—Worldwide, (2012) (listed as document FP6 on the accompanying form PTO/SB/08A).

Cagle, P.T., et al., "Folate Receptor in Adenocarcinoma and Squamous Cell Carcinoma of the Lung Potential Target for Folate-Linked Therapeutic Agents," *Arch Pathol Lab Med Epub*: 1-4, College of Amercian Pathologists, United States (2012).

Franklin, W.A., et al., "New Anti-Lung-Cancer-antibody Cluster 12 Reacts With Human Folate Receptors Present on Adenocarcinoma," *Int. J. Cancer Supplement 8*: 89-95, Wiley-Liss, Inc., United States (1994).

Hartmann, L.C., et al., "Folate receptor overexpression is associated with poor outcome in breast cancer," *Int. J. Cancer 121*: 938-942, Wiley-Liss, Inc., United States (2007).

Jones, M.B., et al., "Rationale for folate receptor alpha targeted therapy in "high risk" endometrial carcinomas," *Int. J. Cancer 123*1699-1703, Wiley-Liss, Inc., United States (2008).

Scorer, P., et al., "A Full Immunohistochemical Evaluation of a Novel Monoclonal Antibody to Folate Receptor—alpha (FR-α)," *reAGENTS 3*: 8-12, Leica Biosystems Newcastle Ltd, United Kingdom (May 2010).

Smith, A.E., et al., "A Novel Monoclonal Antibody for Detection of Folate Receptor Alpha in Paraffin-Embedded Tissues," *HYBRIDOMA 26(5)*:281-288, Mary Ann Liebert, Inc., United States (2007).

International Search Report in International Application No. PCT/US2012/031544, International Searching Authority, United States, Alexandria, VA, mailed Sept. 21, 2012.

International Search Report in International Application No. PCT/US2012/032155, International Searching Authority, United States, Alexandria, VA, mailed Jul. 6, 2012.

Figini, M., et al., "Panning Phage Antibody Libraries on Cells: Isolation of Human Fab Fragments against Ovarian Carcinoma Using Guided Selection," *Cancer Research* 58:991-996, American Association of Cancer Research, United States (1998).

Bendig, M.M., "Humanization of Rodent Monoclonal Antibodies by CDR Grafting," *Methods: A Comparison to Methods in Enzymology* 8:83-93, Academic Press, Inc., United States (1995).

Colman, P.M., "Effects of amino acid sequence changes on antibody-antigen interactions," *Research in Immunology* 145:33-36, Elsevier, France (1994).

Colnaghi, M.I., "Generation of Monoclonal Antibodies for In Vivo Approaches," *Nucl. Med. Biol.* 18(1):15-18, Pergamon Press plc, England (1991).

Paul, W.E., "Structure and Function of Immunoglobulins," in *Fundamental Immunology, Third Edition*, pp. 292-295, Raven Press, Ltd., New York, United States (1993).

Portolano, S., et al., "Lack of Promiscuity in Autoantigen-Specific H and L Chain Combinations as Revealed by Human H and L Chain 'Roulette,'" *The Journal of Immunology 150(3)*:880-887, The American Association of Immunologists, United States (1993).

Rudikoff, S., et al., "Single amino acid substitution altering antigen-binding specificity," *Proc. Natl. Acad. Sci. USA* 79:1979-1983, National Academy of Sciences, United States (1982).

Lu, Y. and Low, P.S., "Immunotherapy of folate receptor-expressing tumors: review of recent advances and future prospects," *Journal of Controlled Release* 91:17-29, Elsevier B.V., Netherlands (2003).

NCL-L-FRalpha, "Novocastra™ Liquid Mouse Monoclonal Antibody Folate Receptor Alpha: Product Code: NCL-L-FRalpha," 40 Pages, Leica Biosystems Newcastle Ltd, England (2009).

Pagnelli, G., et al., "Two-step tumour targetting in ovarian cancer patients using.biotinylated monoclonal antibodies and radioactive streptavidin," *Eur J Nucl Med* 19:322-329, Springer-Verlag, Germany (1992).

Allard, J.E., et al., "Overexpression of folate binding protein is associated with shortened progression-free survival in uterine adenocarcinomas," *Gynecologic Oncology 107(1)*:52-57, Academic Press, United States (2007).

(56) References Cited

OTHER PUBLICATIONS

Bueno, R., et al., "The α Folate Receptor is Highly Activated in Malignant Pleural Mesothelioma," *The Journal of Thoracic and Cardiovascular Surgery 121(2)*:225-233, Mosby, United States (2001).

Farrell, C., et al., "Population pharmacokinetics of farletuzumab, a humanized monoclonal antibody against folate receptor alpha, in epithelial ovarian cancer," *Cancer Chemotherapy and Pharmacology 70(5)*:727-734, Springer Verlag, Germany (Nov. 2012, Epub: Sep. 7, 2012).

Figini, M., et al., "Conversion of murine antibodies to human antibodies and their optimization for ovarian cancer therapy targeted to the folate receptor," *Cancer Immunology and Immunotherapy 58(4)*:531-546, Springer Verlag, Germany (2009).

Kalli, R.K., et al., "Folate receptor alpha as a tumor target in epithelial ovarian cancer," *Gynecologic Oncology 108(3)*:619-626, Academic Press, United States (2008).

Lawson, N. and Scorer, P., "Evaluation of Antibody to Folate Receptor alpha (FR-a)," published online on May 31, 2010, accessed at www.leicabiosystems.com/pathologyleaders/evaluation-of-antibody-to-folate-receptor-alpha-fr-%CE%B1/, accessed on Oct. 27, 2014 (1 page).

Nutt, J.E., et al., "The role of folate receptor alpha (Fα) in the response of malignant pleural mesothelioma to pemetrexed-containing chemotherapy," *British Journal of Cancer 102(3)*:553-560, Nature Publishing Group, England (2010).

Office Action mailed Dec. 24, 2014, in U.S. Appl. No. 14/015,653, Testa, N.E., et al., filed Aug. 30, 2013.

International Search Report for International Application No. PCT/US2014/037911, International Searching Authority, United States, mailed on Oct. 31, 2014.

Supplementary Partial European Search Report for EP Application No. EP 12 76 4885, The Hague, Netherlands, mailed on Nov. 21, 2014.

Search Report and Written Opinion for SG Patent Application No. 20130770040, Intellectual Property Office of Singapore, Singapore, mailed on Dec. 30, 2014.

Mantovani, L.T., et al., "Folate Binding Protein Distribution in Normal Tissues and Biological Fluids From Ovarian Carcinoma Patients as Detected by the Monoclonal Antibodies MOv18 and MOv19," *European Journal of Cancer 30A(3)*:363-369, Pergamon Press, England (1994).

\* cited by examiner

Figure 1A

| Light Chain | | | | |
|---|---|---|---|---|
| Kabat # | muMov19 | DPK19 | huMov19v1.00 | huMov19v1.60 |
| 1 | D | D | D | D |
| 3 | E | *V* | *V* | *V* |
| 5 | T | T | T | T |
| 9 | A | *L* | *L* | *L* |
| 15 | L | L | L | L |
| 17 | Q | Q | Q | Q |
| 18 | R | *P* | *P* | *P* |
| 40 | P | P | P | P |
| 41 | G | G | G | G |
| 42 | Q | Q | Q | Q |
| 45 | K | *R* | *R* | *R* |
| 57 | G | G | G | G |
| 60 | T | *D* | *D* | *D* |
| 67 | S | S | S | S |
| 70 | D | D | D | D |
| 74* | N | K | N | *T\** |
| 76 | H | *S* | *S* | *S* |
| 80 | E | *A* | *A* | *A* |
| 81 | E | E | E | E |
| 100 | G | G | G | G |
| 103 | K | K | K | K |
| 105 | E | E | E | E |
| 107 | K | K | K | K |
| 108 | R | R | R | R |

Figure 1B

| | Heavy Chain | | |
|---|---|---|---|
| Kabat # | muMov19 | 8m27 | huMov19 |
| 1 | Q | Q | Q |
| 3 | Q | Q | Q |
| 5 | Q | *V* | *V* |
| 9 | A | A | A |
| 11 | L | *V* | *V* |
| 13 | K | K | K |
| 14 | P | P | P |
| 19 | K | K | K |
| 23 | K | K | K |
| 28 | S | *T* | *T* |
| 41 | H | *P* | *P* |
| 42 | G | G | G |
| 43 | K | *Q* | *Q* |
| 61 | Q | Q | Q |
| 62 | N | *K* | *K* |
| 64 | K | *Q* | *Q* |
| 65 | D | *G* | *G* |
| 73 | K | K | K |
| 74 | S | S | S |
| 82B | S | S | S |
| 84 | S | S | S |
| 85 | E | E | E |
| 105 | Q | Q | Q |
| 112 | S | S | S |
| 113 | S | S | S |

Figure 1C and 1D

C

| FR1-21 V$_l$ | | |
|---|---|---|
| Kabat position | Murine residue | Human residue |
| 1 | D | D |
| 3 | V | V |
| 9 | S | S |
| 10 | Y | *S* |
| 15 | L | *V* |
| 18 | R | R |
| 40 | P | P |
| 41 | G | G |
| 42 | N | *K* |
| 45 | R | *K* |
| 57 | G | G |
| 60 | S | S |
| 67 | S | S |
| 80 | Q | Q |
| 81 | T | *P* |
| 100 | S | *Q* |
| 103 | K | K |
| 105 | E | E |
| 107 | K | K |
| 108 | R | R |

D

| FR1-21 V$_H$ | | |
|---|---|---|
| Kabat position | Murine residue | Human residue |
| 1 | E | E |
| 3 | K | *Q* |
| 11 | L | *V* |
| 13 | K | K |
| 14 | P | P |
| 17 | S | S |
| 19 | K | K |
| 41 | P | P |
| 42 | D | *G* |
| 43 | K | K |
| 44 | R | *G* |
| 60 | P | *S* |
| 61 | D | *P* |
| 63 | V | *F* |
| 64 | K | *Q* |
| 65 | G | G |
| 73 | N | *K* |
| 74 | A | *S* |
| 75 | K | K |
| 83 | K | K |
| 84 | S | *A* |
| 85 | E | E |
| 105 | Q | Q |
| 112 | S | S |

Figure 2

A

```
                                      1                                                           60
SEQ. ID NO: 18    muMov19 LC          DIELTQSPASLAVSLGQRAIISCKASQSVSFAGTSLMHWYHQKPGQQPKLLIYRASNLEA
SEQ ID NO: 10     huMov19LCv1.00      --V-----L--------P----------------------------R-----------
SEQ ID NO: 11     huMov19LCv1.60      --V-----L--------P----------------------------R-----------

61                                                         112
                  muMov19 LC          GVPTRFSGSGSKTDFTLNIHPVEEEDAATYYCQQSREYPYTFGGGTKL
                  huMov19LCv1.00      ---D------------N-S---A------------------------EIKR
                  huMov19LCv1.60      ---D------------T-S---A------------------------EIKR
```

B

```
                                      1                                                           60
SEQ ID NO: 17     muMov19 HC          QVQLQQSGAELVKPGASVKISCKASGYSFTGYFMNWVKQSHGKSLEWIGRIHPYDGDTFY
SEQ ID NO: 4      huMov19 HC          ----V-----V----------------T-----------P-Q-----------------

61                                                        118
                  muMov19 HC          NQNFKDKATLTVDKSSNTAHMELLSLTSEDFAVYYCTRYDGSRAMDYWGQGTTVTVS
                  huMov19 HC          --K-QG---------------------------------------------------S
```

C

```
                                      1                                                           60
SEQ ID NO: 35     muFR1-21 LC         DIQMTQSSSYLSVSLGGRVTITCKASDHINNWLAWYQQKPGNAPRLLISGATSLETGVPS
SEQ ID NO: 41     huFR1-21 LC         ----------S----V------------------------K--K---------------

61                                                        108
SEQ ID NO: 36     muFR1-21 LC         RFSGSGSGKDYTLSISSLQTEDVATYYCQQYWSTPFTFGSGTKLEIKR
SEQ ID NO: 42     huFR1-21 LC         ------------------P----------------Q--------
```

D

```
                                      1                                                           60
                  muFR1-21 HC         EVKLVESGGDLVKPGGSLKLSCAASGFTFSSYGMSWVRQTPDKRLECVATISSGGSYTYY
                  huFR1-21 HC         --Q-------V--------------------------G-G-------------------

61                                                        120
                  muFR1-21 HC         PDGVKGRFTISRDNAKNTLYLQMSSLKSEDTAMYYCARDGEGGLYAMDYWGQGTSVTVSS
                  huFR1-21 HC         SP-FQ--------KS------------A--------------------------------
```

Figure 5

| Clone | Isotype | Affinity on SKOV3 cells, Kd, nM | Cytotoxic activity of PEG4-mal-DM4 conjugates on KB cells, IC50, nM (continuous exposure) |
|---|---|---|---|
| HuMov19 | IgG1 | 0.07 | 0.15 |
| muFR1-9 | IgG1 | 0.13 | 0.22 |
| muFR1-13 | IgG2b | 0.66 | 0.15 |
| muFR1-22 | IgG2a | 0.69 | 0.14 |
| muFR1-23 | IgG2a | 0.55 | 0.13 |
| huFR1-23 | IgG1 | 0.60 | |
| muFR1-21 | IgG2b | 0.07 | 0.10 |
| huFR1-21 | IgG1 | 0.07 | 0.10 |

10 mg/kg single injection day 6 post inoculation, KB model

Figure 12
A
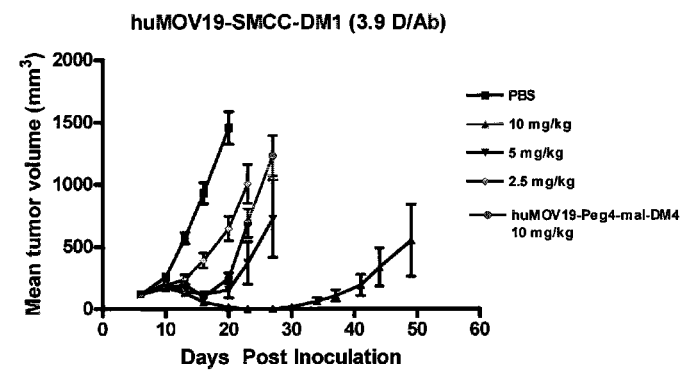
B
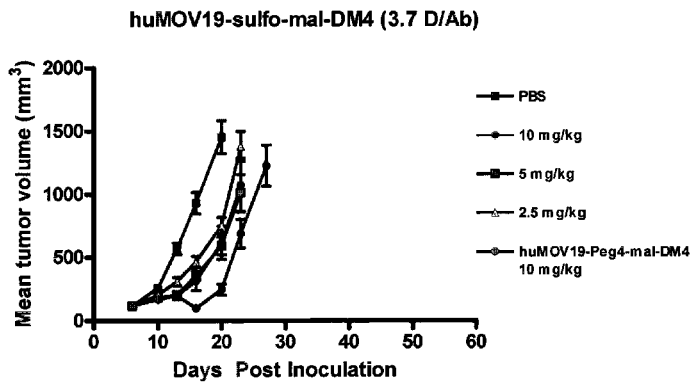
C
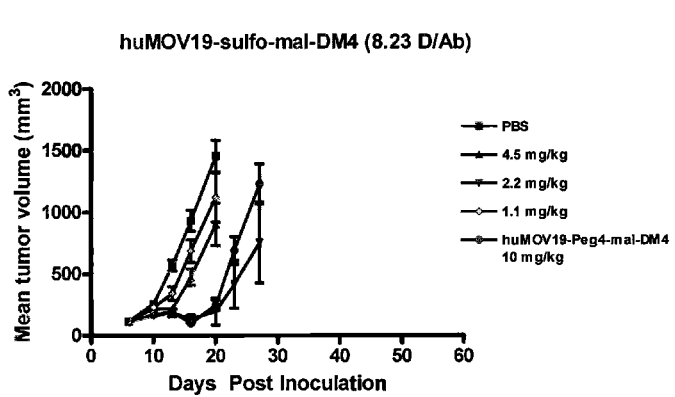

Figure 13
A. 5 mg/kg
single injection
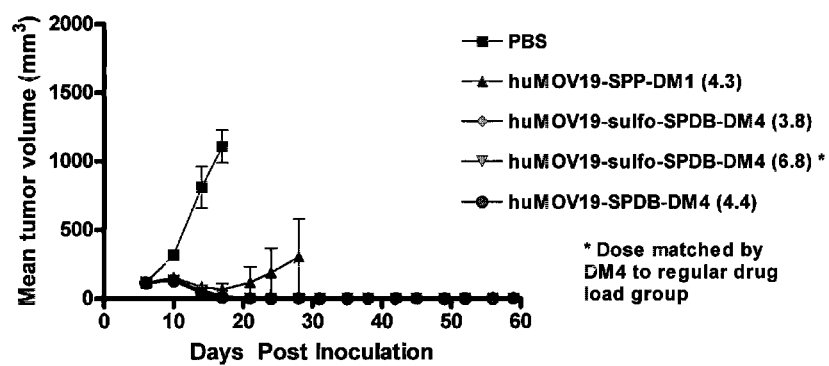
B. 2.5 mg/kg
single injection
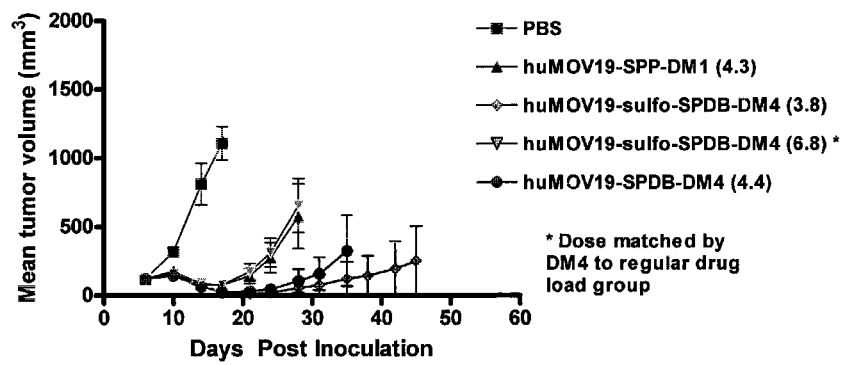

| MODEL | Dosage per injection | T/C (%) | (T-C) in days | log cell kill | Regressions | | Tumor free survivors day 208 | Comments |
|---|---|---|---|---|---|---|---|---|
| | | | | | Partial | Complete | | |
| OVCAR-3 | 25 µg/kg | 18 | 21.0 | 0.7 | 2/6 | 1/6 | 0/6 | active |
| | 50 µg/kg | 0 | 74.5 | 2.4 | 6/6 | 4/6 | 0/6 | highly active |
| | 100 µg/kg | 0 | 120.0 | 3.9 | 6/6 | 6/6 | 0/6 | highly active |

| MODEL | Dosage per injection | T/C (%) | (T-C) in days | log cell kill | Regressions Partial | Complete | Tumor free survivors day 120 | Comments |
|---|---|---|---|---|---|---|---|---|
| IGROV-1 | 25 µg/kg | 55 | 6.0 | 0.2 | 0/6 | 0/6 | 0/6 | inactive |
| | 50 µg/kg | 7 | 41.0 | 1.1 | 5/6 | 0/6 | 0/6 | highly active |
| | 100 µg/kg | 5 | 67.0 | 1.8 | 6/6 | 0/6 | 0/6 | highly active |

| MODEL | Dosage per injection | T/C (%) | (T-C) in days | log cell kill | Regressions Partial | Complete | Tumor free survivors day 92 | Comments |
|---|---|---|---|---|---|---|---|---|
| OV-90 | 25 µg/kg | 77 | 5.0 | 0.2 | 0/6 | 0/6 | 0/6 | inactive |
| | 50 µg/kg | 36 | 26.0 | 1.2 | 0/6 | 0/6 | 0/6 | active |
| | 100 µg/kg | 18 | 40.0 | 1.9 | 2/6 | 0/6 | 0/6 | active |

Figure 18
(A)
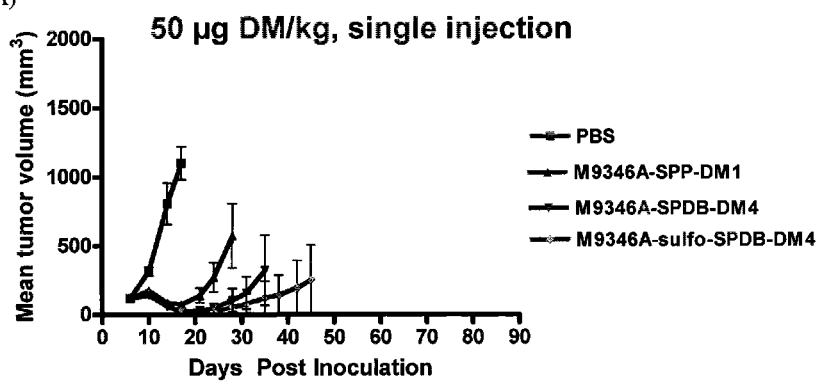
(B)
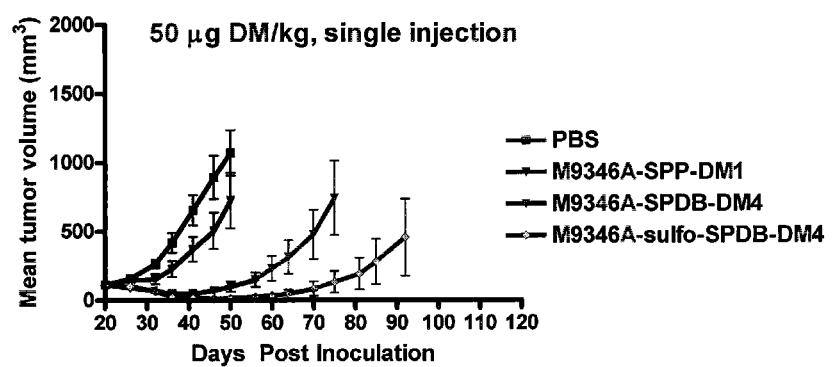

SEQUENCE LISTING

```
<160> NUMBER OF SEQ ID NOS: 131

<210> SEQ ID NO 1
<211> LENGTH: 5
<212> TYPE: PRT
<213> ORGANISM: Artificial sequence
<220> FEATURE:
<223> OTHER INFORMATION: huMov19 vHC CDR1

<400> SEQUENCE: 1

Gly Tyr Phe Met Asn
1               5

<210> SEQ ID NO 2
<211> LENGTH: 17
<212> TYPE: PRT
<213> ORGANISM: Artificial sequence
<220> FEATURE:
<223> OTHER INFORMATION: huMov19 vHC CDR2

<400> SEQUENCE: 2
```

Arg Ile His Pro Tyr Asp Gly Asp Thr Phe Tyr Asn Gln Lys Phe Gln
1               5                   10                  15

Gly

<210> SEQ ID NO 3
<211> LENGTH: 9
<212> TYPE: PRT
<213> ORGANISM: Artificial sequence
<220> FEATURE:
<223> OTHER INFORMATION: huMov19 vHC CDR3

<400> SEQUENCE: 3

Tyr Asp Gly Ser Arg Ala Met Asp Tyr
1               5

<210> SEQ ID NO 4
<211> LENGTH: 118
<212> TYPE: PRT
<213> ORGANISM: Artificial sequence
<220> FEATURE:
<223> OTHER INFORMATION: huMov19 vHC

<400> SEQUENCE: 4

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 5
<211> LENGTH: 440
<212> TYPE: DNA
<213> ORGANISM: Artificial sequence
<220> FEATURE:
<223> OTHER INFORMATION: huMov19 vHC nucleic acid sequence

<400> SEQUENCE: 5
aagcttgcca ccatgggttg gtcatgcatc atcctcttct tggttgcaac tgctaccgga      60
gtgcacagtc aggtacagct cgtgcagtcc ggcgccgagg tggtgaagcc tggtgccagc     120
gtgaagatct cctgtaaagc cagtggatac acattcaccg gttatttat gaattgggtg      180 aaacagagcc caggccaatc cctcgaatgg ataggggcgaa tccacccata tgacggggac    240 acctttttaca accagaaatt ccaggggaaa gccactctga cagtggacaa gagttccaac    300
actgcacaca tggagcttct ctccctgacc agcgaagact cgctgtttta ttactgtacc     360
cgttatgatg gttcccgtgc aatggactac tggggccaag gaccactgt caccgtaagt     420 tccgccagca ccaagggccc                                                 440

```
<210> SEQ ID NO 6
<211> LENGTH: 448
<212> TYPE: PRT
<213> ORGANISM: Artificial sequence
<220> FEATURE:
<223> OTHER INFORMATION: huMov19 HC amino acid sequence

<400> SEQUENCE: 6

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
```

```
                370               375               380
Asn Gly Gln Pro Glu Asn Asn Tyr Lys Thr Thr Pro Pro Val Leu Asp
385                 390               395               400

Ser Asp Gly Ser Phe Phe Leu Tyr Ser Lys Leu Thr Val Asp Lys Ser
            405               410               415

Arg Trp Gln Gln Gly Asn Val Phe Ser Cys Ser Val Met His Glu Ala
                420               425               430

Leu His Asn His Tyr Thr Gln Lys Ser Leu Ser Leu Ser Pro Gly Lys
        435               440               445

<210> SEQ ID NO 7
<211> LENGTH: 15
<212> TYPE: PRT
<213> ORGANISM: Artificial sequence
<220> FEATURE:
<223> OTHER INFORMATION: huMov19 vLC CDR1

<400> SEQUENCE: 7

Lys Ala Ser Gln Ser Val Ser Phe Ala Gly Thr Ser Leu Met His
1               5                   10                  15

<210> SEQ ID NO 8
<211> LENGTH: 7
<212> TYPE: PRT
<213> ORGANISM: Artificial sequence
<220> FEATURE:
<223> OTHER INFORMATION: huMov19 vLC CDR2

<400> SEQUENCE: 8

Arg Ala Ser Asn Leu Glu Ala
1               5

<210> SEQ ID NO 9
<211> LENGTH: 9
<212> TYPE: PRT
<213> ORGANISM: Artificial sequence
<220> FEATURE:
<223> OTHER INFORMATION: huMov19 vLC CDR3

<400> SEQUENCE: 9

Gln Gln Ser Arg Glu Tyr Pro Tyr Thr
1               5

<210> SEQ ID NO 10
<211> LENGTH: 112
<212> TYPE: PRT
<213> ORGANISM: Artificial sequence
<220> FEATURE:
<223> OTHER INFORMATION: huMov19 vLCv1.00

<400> SEQUENCE: 10

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
```

```
                    85                  90                  95

Glu Tyr Pro Tyr Thr Phe Gly Gly Gly Thr Lys Leu Glu Ile Lys Arg
                100                 105                 110
```

<210> SEQ ID NO 11
<211> LENGTH: 112
<212> TYPE: PRT
<213> ORGANISM: Artificial sequence
<220> FEATURE:
<223> OTHER INFORMATION: huMov19 vLCv1.60

<400> SEQUENCE: 11

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
                100                 105                 110
```

<210> SEQ ID NO 12
<211> LENGTH: 218
<212> TYPE: PRT
<213> ORGANISM: Artificial sequence
<220> FEATURE:
<223> OTHER INFORMATION: huMov19 LCv1.00

<400> SEQUENCE: 12

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 13
<211> LENGTH: 218
<212> TYPE: PRT
<213> ORGANISM: Artificial sequence
<220> FEATURE:
<223> OTHER INFORMATION: huMov19 LCv1.60

<400> SEQUENCE: 13

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 14
<211> LENGTH: 408
<212> TYPE: DNA
<213> ORGANISM: Artificial sequence
<220> FEATURE:
<223> OTHER INFORMATION: huMov19 LCv1.00 nucleic acid

<400> SEQUENCE: 14
gaattcgcca ccatgggctg gagctgcatt atccttttc tggtagccac agctacaggc      60
gtgcatagcg atatcgtgct gacacaatcc cccctctctc tggccgtgtc actcggacag     120
cccgctatca tcagctgcaa agccagccag tctgtcagct cgctggaaac aagtcttatg     180
cattggtatc atcagaagcc tggccagcaa cccaggctgc tgatctatcg agcctcaaac     240
```

```
ttggaagcag gagtgccaga ccggttttct gggtccggga gtaaaaccga ttttacactt    300
aatatctcac ctgtcgaggc cgaggacgcc gccacctact actgtcagca gagccgagag    360
tacccttaca cttttggcgg tgggactaaa ctggaaataa aacgtacg                 408
```

<210> SEQ ID NO 15
<211> LENGTH: 408
<212> TYPE: DNA
<213> ORGANISM: Artificial sequence
<220> FEATURE:
<223> OTHER INFORMATION: huMov19 LCv1.60 nucleic acid

<400> SEQUENCE: 15

```
gaattcgcca ccatgggctg gtcttgtatc atcctgtttc tggtggccac cgcaaccggt     60
gttcactccg acattgtgct gacacagtcc cccctttcac tggctgtatc cctcggccag    120
cccgctatca tcagctgcaa ggctagccag agcgtgagtt ttgccggcac ttcacttatg    180
cattggtacc atcagaaacc aggccagcaa cctaggctgc tgatttatcg ggctagcaac    240
ctggaggccg gcgtgcccga ccgctttagc gggagcggct ccaagactga cttcactctg    300
accatctccc ccgtagaagc agaagatgct gcaacctact actgtcagca gtctcgcgag    360
tatccttata cattcggagg cggaactaaa ctggagatta aacgtacg                 408
```

<210> SEQ ID NO 16
<211> LENGTH: 17
<212> TYPE: PRT
<213> ORGANISM: Artificial sequence
<220> FEATURE:
<223> OTHER INFORMATION: muMov19 vHC CDR2

<400> SEQUENCE: 16

Arg Ile His Pro Tyr Asp Gly Asp Thr Phe Tyr Asn Gln Asn Phe Lys
1               5                   10                  15

Asp

<210> SEQ ID NO 17
<211> LENGTH: 117
<212> TYPE: PRT
<213> ORGANISM: Artificial sequence
<220> FEATURE:
<223> OTHER INFORMATION: muMov19 vHC_CAA68252

<400> SEQUENCE: 17

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Phe Met Asn Trp Val Lys Gln Ser His Gly Lys Ser Leu Glu Trp Ile
            35                  40                  45

Gly Arg Ile His Pro Tyr Asp Gly Asp Thr Phe Tyr Asn Gln Asn Phe
        50                  55                  60

Lys Asp Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser
        115

<210> SEQ ID NO 18
<211> LENGTH: 108
<212> TYPE: PRT
<213> ORGANISM: Artificial sequence
<220> FEATURE:
<223> OTHER INFORMATION: muMov19 vLC_CAA68253

<400> SEQUENCE: 18

```
Asp Ile Glu Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Lys Leu Leu Ile Tyr Arg Ala Ser Asn Leu Glu Ala Gly Val Pro Thr
    50                  55                  60

Arg Phe Ser Gly Ser Gly Ser Lys Thr Asp Phe Thr Leu Asn Ile His
65                  70                  75                  80

Pro Val Glu Glu Glu Asp Ala Ala Thr Tyr Tyr Cys Gln Gln Ser Arg
                85                  90                  95

Glu Tyr Pro Tyr Thr Phe Gly Gly Gly Thr Lys Leu
            100                 105
```

<210> SEQ ID NO 19
<211> LENGTH: 448
<212> TYPE: PRT
<213> ORGANISM: Artificial sequence
<220> FEATURE:
<223> OTHER INFORMATION: chMov19 HC

<400> SEQUENCE: 19

```
Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile His Pro Tyr Asp Gly Asp Thr Phe Tyr Asn Gln Asn Phe
    50                  55                  60

Lys Asp Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 20
<211> LENGTH: 218
<212> TYPE: PRT
<213> ORGANISM: Artificial sequence
<220> FEATURE:
<223> OTHER INFORMATION: chMov19 LC

<400> SEQUENCE: 20

Asp Ile Glu Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Lys Leu Leu Ile Tyr Arg Ala Ser Asn Leu Glu Ala Gly Val Pro Thr
    50                  55                  60

Arg Phe Ser Gly Ser Gly Ser Lys Thr Asp Phe Thr Leu Asn Ile His
65                  70                  75                  80

Pro Val Glu Glu Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 441
<212> TYPE: DNA
<213> ORGANISM: Artificial sequence
<220> FEATURE:
<223> OTHER INFORMATION: chMov19 HC nucleic acid

<400> SEQUENCE: 21
aagcttgcca ccatggggttg gtcttgtatt atcctctttc tcgtcgcaac cgcaacaggc     60
gtccattcac aagtccaact gcagcaatcc ggcgccgaac tcgttaaacc tggagcatct    120
gttaaaatct catgtaaagc atcaggatac tcatttactg gctatttat gaactgggtc     180 aaacaatcac acggaaaatc acttgaatgg atcggacgta ttcaccccta tgatggcgat    240 acttttaca accagaactt caaagacaaa gctacactca ccgttgacaa atcatctaac     300
accgctcaca tggaactcct ttcactcaca tctgaagact cgctgttta ttactgtact    360 agatacgatg gatcaagagc tatggattat tggggacaag gaacaacagt cacagtctca    420
tctgcatcaa ctaagggccc a                                               441

<210> SEQ ID NO 22
<211> LENGTH: 408
<212> TYPE: DNA
<213> ORGANISM: Artificial sequence
<220> FEATURE:
<223> OTHER INFORMATION: chMov19 LC nucleic acid

<400> SEQUENCE: 22
gaattcgcca ccatgggttg gtcttgtatt atcctctttc tcgtcgcaac cgcaacaggc     60
gtccattcag atatcgaact cacacaatca ccagcttccc tcgcagtctc tctcggtcaa    120
cgcgcaatca tctcttgtaa agcctcccaa tcagtctcat cgccggcac gtccctcatg     180 cattggtacc atcaaaaacc cggtcagcaa cccaaactcc ttatctatag agcaagcaac    240
ctcgaagcag gcgttcccac cagatttagc ggatcaggaa gtaaaccga tttcacactc    300 aacattcatc cagtcgaaga agaagatgca gctacttatt attgccaaca gtctagagaa    360
tatccataca cattcggagg gggtaccaaa cttgaaatta acgtacg                   408

<210> SEQ ID NO 23
<211> LENGTH: 117
<212> TYPE: PRT
<213> ORGANISM: Artificial sequence
<220> FEATURE:
<223> OTHER INFORMATION: muMov19 vHC_CAA68252

<400> SEQUENCE: 23
```

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile His Pro Tyr Asp Gly Asp Thr Phe Tyr Asn Gln Asn Phe
    50                  55                  60

Lys Asp Lys Ala Thr Leu Thr Val Asp Lys Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser
            115

<210> SEQ ID NO 24
<211> LENGTH: 108
<212> TYPE: PRT
<213> ORGANISM: Artificial sequence
<220> FEATURE:
<223> OTHER INFORMATION: muMov19 vLC_CAA68253

<400> SEQUENCE: 24

Asp Ile Glu Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Lys Leu Leu Ile Tyr Arg Ala Ser Asn Leu Glu Ala Gly Val Pro Thr
    50                  55                  60

Arg Phe Ser Gly Ser Gly Ser Lys Thr Asp Phe Thr Leu Asn Ile His
65                  70                  75                  80

Pro Val Glu Glu Glu Asp Ala Ala Thr Tyr Tyr Cys Gln Gln Ser Arg
                85                  90                  95

Glu Tyr Pro Tyr Thr Phe Gly Gly Gly Thr Lys Leu
            100                 105

<210> SEQ ID NO 25
<211> LENGTH: 257
<212> TYPE: PRT
<213> ORGANISM: Homo sapiens
<220> FEATURE:
<221> NAME/KEY: MISC_FEATURE
<222> LOCATION: (1)..(257)

<400> SEQUENCE: 25

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr

```
              65                  70                  75                  80
Leu Tyr Arg Phe Asn Trp Asn His Cys Gly Glu Met Ala Pro Ala Cys
                85                  90                  95
Lys Arg His Phe Ile Gln Asp Thr Cys Leu Tyr Glu Cys Ser Pro Asn
            100                 105                 110
Leu Gly Pro Trp Ile Gln Val Asp Gln Ser Trp Arg Lys Glu Arg
        115                 120                 125
Val Leu Asn Val Pro Leu Cys Lys Glu Asp Cys Glu Gln Trp Trp Glu
    130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Ala Val Gly Ala Ala Cys Gln
                165                 170                 175
Pro Phe His Phe Tyr Phe Pro Thr Pro Thr Val Leu Cys Asn Glu Ile
                180                 185                 190
Trp Thr His Ser Tyr Lys Val Ser Asn Tyr Ser Arg Gly Ser Gly Arg
            195                 200                 205
Cys Ile Gln Met Trp Phe Asp Pro Ala Gln Gly Asn Pro Asn Glu Glu
        210                 215                 220
Val Ala Arg Phe Tyr Ala Ala Ala Met Ser Gly Ala Gly Pro Trp Ala
225                 230                 235                 240
Ala Trp Pro Phe Leu Leu Ser Leu Ala Leu Met Leu Leu Trp Leu Leu
                245                 250                 255
Ser

<210> SEQ ID NO 26
<211> LENGTH: 771
<212> TYPE: DNA
<213> ORGANISM: Homo sapiens
<220> FEATURE:
<221> NAME/KEY: misc_feature
<222> LOCATION: (1)..(771)

<400> SEQUENCE: 26
atggctcagc ggatgacaac acagctgctg ctccttctag tgtgggtggc tgtagtaggg      60
gaggctcaga caaggattgc atgggccagg actgagcttc tcaatgtctg catgaacgcc     120
aagcaccaca aggaaaagcc aggccccgag gacaagttgc atgagcagtg tcgaccctgg     180
aggaagaatg cctgctgttc taccaacacc agccaggaag cccataagga tgtttcctac     240
ctatatagat tcaactggaa ccactgtgga gagatggcac tgcctgcaa acggcatttc      300 atccaggaca cctgcctcta cgagtgctcc cccaacttgg ggccctggat ccagcaggtg     360
gatcagagct ggcgcaaaga gcgggtactg aacgtgcccc tgtgcaaaga ggactgtgag     420
caatggtggg aagattgtcg cacctcctac acctgcaaga gcaactggca caagggctgg     480
aactggactt cagggtttaa caagtgcgca gtgggagctg cctgccaacc tttccatttc     540
tacttcccca cacccactgt tctgtgcaat gaaatctgga ctcactccta caaggtcagc     600
aactacagcc gagggagtgg ccgctgcatc cagatgtggt tcgacccagc caagggcaac     660
cccaatgagg aggtggcgag gttctatgct gcagccatga gtggggctgg gccctgggca     720
gcctggcctt tcctgcttag cctggcccta atgctgctgt ggctgctcag c              771

<210> SEQ ID NO 27
<211> LENGTH: 11
<212> TYPE: PRT
<213> ORGANISM: Artificial sequence
```

<220> FEATURE:
<223> OTHER INFORMATION: FR1-21 vLC CDR1

<400> SEQUENCE: 27

Lys Ala Ser Asp His Ile Asn Asn Trp Leu Ala
1               5                   10

<210> SEQ ID NO 28
<211> LENGTH: 7
<212> TYPE: PRT
<213> ORGANISM: Artificial sequence
<220> FEATURE:
<223> OTHER INFORMATION: FR1-21 vLC CDR2

<400> SEQUENCE: 28

Gly Ala Thr Ser Leu Glu Thr
1               5

<210> SEQ ID NO 29
<211> LENGTH: 9
<212> TYPE: PRT
<213> ORGANISM: Artificial sequence
<220> FEATURE:
<223> OTHER INFORMATION: FR1-21 vLC CDR3

<400> SEQUENCE: 29

Gln Gln Tyr Trp Ser Thr Pro Phe Thr
1               5

<210> SEQ ID NO 30
<211> LENGTH: 6
<212> TYPE: PRT
<213> ORGANISM: Artificial sequence
<220> FEATURE:
<223> OTHER INFORMATION: FR1-21 vHC CDR1

<400> SEQUENCE: 30

Ser Ser Tyr Gly Met Ser
1               5

<210> SEQ ID NO 31
<211> LENGTH: 10
<212> TYPE: PRT
<213> ORGANISM: Artificial sequence
<220> FEATURE:
<223> OTHER INFORMATION: FR1-21 vHC CDR2

<400> SEQUENCE: 31

Thr Ile Ser Ser Gly Gly Ser Tyr Thr Tyr
1               5                   10

<210> SEQ ID NO 32
<211> LENGTH: 11
<212> TYPE: PRT
<213> ORGANISM: Artificial sequence
<220> FEATURE:
<223> OTHER INFORMATION: FR1-21 vHC CDR3

<400> SEQUENCE: 32

Asp Gly Glu Gly Gly Leu Tyr Ala Met Asp Tyr
1               5                   10

<210> SEQ ID NO 33
<211> LENGTH: 17
<212> TYPE: PRT
<213> ORGANISM: Artificial sequence
<220> FEATURE:

<223> OTHER INFORMATION: FR1-21 Kabat murine CDR-H2

<400> SEQUENCE: 33

Thr Ile Ser Ser Gly Gly Ser Tyr Thr Tyr Tyr Pro Asp Gly Val Lys
1               5                   10                  15

Gly

<210> SEQ ID NO 34
<211> LENGTH: 17
<212> TYPE: PRT
<213> ORGANISM: Artificial sequence
<220> FEATURE:
<223> OTHER INFORMATION: FR1-21 Kabat human CDR-H2

<400> SEQUENCE: 34

Thr Ile Ser Ser Gly Gly Ser Tyr Thr Tyr Tyr Ser Pro Gly Phe Gln
1               5                   10                  15

Gly

<210> SEQ ID NO 35
<211> LENGTH: 108
<212> TYPE: PRT
<213> ORGANISM: Artificial sequence
<220> FEATURE:
<223> OTHER INFORMATION: muFR1-21 vLC

<400> SEQUENCE: 35

Asp Ile Gln Met Thr Gln Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Ser Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys Arg
            100                 105

<210> SEQ ID NO 36
<211> LENGTH: 120
<212> TYPE: PRT
<213> ORGANISM: Artificial sequence
<220> FEATURE:
<223> OTHER INFORMATION: muFR1-21 vHC

<400> SEQUENCE: 36

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Cys Val
        35                  40                  45

Ala Thr Ile Ser Ser Gly Gly Ser Tyr Thr Tyr Tyr Pro Asp Gly Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Gly Glu Gly Gly Leu Tyr Ala Met Asp Tyr Trp Gly Gln
            100                 105                 110

Gly Thr Ser Val Thr Val Ser Ser
        115                 120

<210> SEQ ID NO 37
<211> LENGTH: 323
<212> TYPE: DNA
<213> ORGANISM: Artificial sequence
<220> FEATURE:
<223> OTHER INFORMATION: muFR1-21 vLC DNA sequence

<400> SEQUENCE: 37
gacatccaga tgacacaatc ttcatcctac ttgtctgtat ctctaggagg cagagtcacc    60
attacttgca aggcaagtga ccacataaat aattggttag cctggtatca gcagaaacca   120
ggaaatgctc ctaggctctt aatatctggt gcaaccagtt tggaaactgg ggttccttca   180
agattcagtg gcagtggatc tggaaaggat acactctca gcatttccag tcttcagact   240
gaagatgttg ctacttatta ctgtcaacag tattggagta ctccattcac gttcggctcg   300
gggacaaagt tggaaataaa acg                                           323

<210> SEQ ID NO 38
<211> LENGTH: 360
<212> TYPE: DNA
<213> ORGANISM: Artificial sequence
<220> FEATURE:
<223> OTHER INFORMATION: muFR1-21HCvarPat

<400> SEQUENCE: 38
gaagtgaagc tggtggagtc tggggagac ttagtgaagc ctggagggtc cctgaaactc    60
tcctgtgcag cctctggatt cactttcagt agctatggca tgtcttgggt tcgccagact   120
ccagacaaga ggttggagtg tgtcgcaacc attagtagtg gtggtagtta cacctactat   180
ccagacggtg tgaaggggcg attcaccatc tccagagaca tgccaagaa caccctgtac   240 ctgcaaatga gcagtctgaa gtctgaggac acagccatgt attactgtgc aagggacggc   300 gagggggggcc tctatgctat ggactactgg ggtcaaggaa cctcagtcac cgtctcctca   360

<210> SEQ ID NO 39
<211> LENGTH: 214
<212> TYPE: PRT
<213> ORGANISM: Artificial sequence
<220> FEATURE:
<223> OTHER INFORMATION: muFR1-21 LC

<400> SEQUENCE: 39

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Ser Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
            195                 200                 205

Phe Asn Arg Asn Glu Cys
        210

<210> SEQ ID NO 40
<211> LENGTH: 456
<212> TYPE: PRT
<213> ORGANISM: Artificial sequence
<220> FEATURE:
<223> OTHER INFORMATION: muFR1-21 HC

<400> SEQUENCE: 40

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Cys Val
        35                  40                  45

Ala Thr Ile Ser Ser Gly Gly Ser Tyr Thr Tyr Tyr Pro Asp Gly Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Gly Glu Gly Gly Leu Tyr Ala Met Asp Tyr Trp Gly Gln
            100                 105                 110

Gly Thr Ser Val Thr Val Ser Ser Ala Lys Thr Thr Pro Pro Ser Val
            115                 120                 125

Tyr Pro Leu Ala Pro Gly Cys Gly Asp Thr Thr Gly Ser Ser Val Thr
        130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Ser Val His Thr Phe Pro Ala Leu
                165                 170                 175

Leu Gln Ser Gly Leu Tyr Thr Met Ser Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

```
Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
            245                 250                 255

Lys Asp Val Leu Met Ile Ser Leu Thr Pro Lys Val Thr Cys Val Val
        260                 265                 270

Val Asp Val Ser Glu Asp Asp Pro Asp Val Gln Ile Ser Trp Phe Val
    275                 280                 285

Asn Asn Val Glu Val His Thr Ala Gln Thr Gln Thr His Arg Glu Asp
    290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
                325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Pro Ala Glu Gln Leu Ser
        355                 360                 365

Arg Lys Asp Val Ser Leu Thr Cys Leu Val Val Gly Phe Asn Pro Gly
    370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
                405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
        435                 440                 445

Thr Ile Ser Arg Ser Pro Gly Lys
450                 455

<210> SEQ ID NO 41
<211> LENGTH: 108
<212> TYPE: PRT
<213> ORGANISM: Artificial sequence
<220> FEATURE:
<223> OTHER INFORMATION: huFR1-21 vLC

<400> SEQUENCE: 41

Asp Ile Gln Met Thr Gln Ser Ser Ser Leu Ser Val Ser Val Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Ser Ser Leu Gln Pro
65                  70                  75                  80

Glu Asp Val Ala Thr Tyr Tyr Cys Gln Gln Tyr Trp Ser Thr Pro Phe
                85                  90                  95

Thr Phe Gly Gln Gly Thr Lys Leu Glu Ile Lys Arg
            100                 105

<210> SEQ ID NO 42
<211> LENGTH: 120
```

<212> TYPE: PRT
<213> ORGANISM: Artificial sequence
<220> FEATURE:
<223> OTHER INFORMATION: huFR1-21 vHC

<400> SEQUENCE: 42

Glu Val Gln Leu Val Glu Ser Gly Gly Asp Val Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Gly Lys Gly Leu Glu Cys Val
        35                  40                  45

Ala Thr Ile Ser Ser Gly Gly Ser Tyr Thr Tyr Tyr Ser Pro Gly Phe
    50                  55                  60

Gln Gly Arg Phe Thr Ile Ser Arg Asp Lys Ser Lys Asn Thr Leu Tyr
65                  70                  75                  80

Leu Gln Met Ser Ser Leu Lys Ala Glu Asp Thr Ala Met Tyr Tyr Cys
                85                  90                  95

Ala Arg Asp Gly Glu Gly Gly Leu Tyr Ala Met Asp Tyr Trp Gly Gln
            100                 105                 110

Gly Thr Ser Val Thr Val Ser Ser
        115                 120

<210> SEQ ID NO 43
<211> LENGTH: 446
<212> TYPE: DNA
<213> ORGANISM: Artificial sequence
<220> FEATURE:
<223> OTHER INFORMATION: huFR1-21VH_co

<400> SEQUENCE: 43
aagcttgcca ccatgggatg gtcatgcatc attcttttc tcgtcgccac tgccacaggt      60
gtgcattccg aggtgcaact tgtagaatct ggcggggatg ttgtgaagcc tggaggtagt     120
ctcaagttgt cctgtgctgc atctgggttt accttctctt cctacggaat gagctgggtg    180
agacagactc ctggcaaggg gctggagtgc gttgccacca ttagtagtgg aggttcttac    240
acctactatt cacctggttt tcagggacgc tttacaatct cccgcgataa gtctaagaac    300
accctttacc tccagatgag tagccttaag gctgaggaca cagccatgta ttattgcgct    360
cgcgatgggg agggagggct ttacgctatg gactactggg gccagggtac cagcgtgacc    420
gtttcctctg ctagtaccaa gggccc                                         446

<210> SEQ ID NO 44
<211> LENGTH: 396
<212> TYPE: DNA
<213> ORGANISM: Artificial sequence
<220> FEATURE:
<223> OTHER INFORMATION: huFR21VL_co

<400> SEQUENCE: 44
gaattcgcca ccatgggatg gtcatgtatc attctgttct tggtagcaac agcaactggc      60
gtccattctg acatccagat gacccaatcc tccagcagct tgtcagtatc cgttgggggc     120
cgcgttacta ttacctgtaa ggcctccgac catataaata ctggcttgc atggtatcaa     180 cagaagcctg ggaaggcacc taaactgctt atctctgggg ccacaagcct ggagaccggc     240
gtgccttcca ggttctctgg aagtggatct ggcaaggact ataccttgag cattagtagc    300
cttcaacctg aggacgtcgc cacctactat tgtcagcagt attggtctac acccttacc     360 tttggacagg gcactaaatt ggagataaaa cgtacg                                      396

<210> SEQ ID NO 45
<211> LENGTH: 214
<212> TYPE: PRT
<213> ORGANISM: Artificial sequence
<220> FEATURE:
<223> OTHER INFORMATION: huFR1-21 LC

<400> SEQUENCE: 45

Asp Ile Gln Met Thr Gln Ser Ser Ser Leu Ser Val Ser Val Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Ser Ser Leu Gln Pro
65                  70                  75                  80

Glu Asp Val Ala Thr Tyr Tyr Cys Gln Gln Tyr Trp Ser Thr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 449
<212> TYPE: PRT
<213> ORGANISM: Artificial sequence
<220> FEATURE:
<223> OTHER INFORMATION: huFR1-21 HC

<400> SEQUENCE: 46

Glu Val Gln Leu Val Glu Ser Gly Gly Asp Val Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Gly Lys Gly Leu Glu Cys Val
        35                  40                  45

Ala Thr Ile Ser Ser Gly Gly Ser Tyr Thr Tyr Tyr Ser Pro Gly Phe
    50                  55                  60

Gln Gly Arg Phe Thr Ile Ser Arg Asp Lys Ser Lys Asn Thr Leu Tyr
65                  70                  75                  80

-continued

```
Leu Gln Met Ser Ser Leu Lys Ala Glu Asp Thr Ala Met Tyr Tyr Cys
             85                  90                  95
Ala Arg Asp Gly Glu Gly Gly Leu Tyr Ala Met Asp Tyr Trp Gly Gln
            100                 105                 110
Gly Thr Ser Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly
```

<210> SEQ ID NO 47
<211> LENGTH: 642
<212> TYPE: DNA
<213> ORGANISM: Artificial sequence
<220> FEATURE:
<223> OTHER INFORMATION: huFR1-21LC DNA sequence

<400> SEQUENCE: 47

```
gacatccaga tgacccaatc ctccagcagc ttgtcagtat ccgttggggg ccgcgttact    60
attacctgta aggcctccga ccatataaat aactggcttg catggtatca acagaagcct   120
gggaaggcac ctaaactgct tatctctggg gccacaagcc tggagaccgg cgtgccttcc   180
aggttctctg gaagtggatc tggcaaggac tataccttga gcattagtag ccttcaacct   240
gaggacgtcg ccacctacta ttgtcagcag tattggtcta cacccttttac ctttggacag   300
ggcactaaat tggagataaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                     642
```

<210> SEQ ID NO 48
<211> LENGTH: 1347
<212> TYPE: DNA
<213> ORGANISM: Artificial sequence
<220> FEATURE:
<223> OTHER INFORMATION: huFR1-21HC DNA sequence

<400> SEQUENCE: 48

```
gaggtgcaac ttgtagaatc tggcggggat gttgtgaagc ctggaggtag tctcaagttg    60
tcctgtgctg catctgggtt taccttctct cctacggaa tgagctgggt gagacagact   120
cctggcaagg ggctggagtg cgttgccacc attagtagtg gaggttctta cacctactat   180
tcacctggtt ttcagggacg ctttacaatc tcccgcgata gtctaagaa cacccttttac   240
ctccagatga gtagccttaa ggctgaggac acagccatgt attattgcgc tcgcgatggg   300
gagggagggc tttacgctat ggactactgg ggccagggta ccagcgtgac cgtttcctct   360
gctagtacca aggggcccat cagttttccc cttggctcca agttctaaatc cacaagcggt   420
ggaacagctg cactgggatg cctcgttaaa gattatttcc ctgagcctgt gacagtgagc   480
tggaatagcg gagcattgac ttcaggtgtg cacactttc ccgctgtgtt gcagtcctcc   540
ggtctgtact cactgtccag tgtcgtaacc gtcccttcta gcagcttggg aacccagacc   600
tacatctgta acgtcaacca taaaccatcc aacacaaagg tggataagaa ggttgaacca   660
aagagctgtg ataagacaca tacatgcccc ccttgtcctg caccagagct cctcggaggt   720
ccatctgtgt tcctgttttcc ccccaaaccc aaggacactc ttatgatctc tcgtactcca   780
gaggtcacct gtgttgttgt cgacgtgagc catgaagatc ccgaggttaa attcaactgg   840
tacgtggatg gagtcgaggt tcacaatgcc aagaccaagc ccaggagga gcaatataat   900
tctacatatc gggtagtgag cgttctgacc gtgctccacc aagattggct caatggaaaa   960
gagtacaagt gcaaggtgtc caacaaggct cttcccgctc ccattgagaa aactatctcc  1020
aaagccaagg ggcagccacg ggaaccccag gtgtatacat gccccccatc tagagacgag  1080
ctgaccaaga accaggtgag tctcacttgt ctggtcaagg gttttaccc ttctgacatt  1140
gctgtagagt gggagtctaa cggacagcca gaaacaact acaagacaac tcccccagtg  1200
ctggacagcg acgggagctt cttcctctac tccaagttga ctgtagacaa gtctagatgg  1260
cagcaaggaa acgttttctc ctgctcagta atgcatgagc tctgcacaa tcactatacc  1320
cagaaatcac tgtcccttag cccaggg                                     1347
```

<210> SEQ ID NO 49
<211> LENGTH: 792
<212> TYPE: DNA
<213> ORGANISM: Artificial sequence
<220> FEATURE:
<223> OTHER INFORMATION: huFolR1 DNA sequence EcoRI to Xba1

<400> SEQUENCE: 49

| | | | | | |
|---|---|---|---|---|---|
| gaattcgcca | ccatggcaca | gcgcatgacc | actcagctcc | tgcttctgtt | ggtttgggtg | 60 |
| gcagtcgtgg | gagaggccca | gaccaggatt | gcttgggcac | gcacagagct | gcttaatgtt | 120 |
| tgcatgaacg | caaagcacca | taaagagaaa | cccggtcccg | aggataagtt | gcacgaacag | 180 |
| tgccgcccctt | ggagaaagaa | tgcatgctgt | agcacgaaca | cctctcagga | ggcgcataaa | 240 |
| gacgtaagct | atttgtatag | atttaactgg | aaccattgcg | gtgaaatggc | acctgcctgt | 300 |
| aaacggcact | ttatccagga | tacttgcttg | tacgagtgta | gcccgaatct | cgggccctgg | 360 |
| attcagcaag | ttgatcagag | ttggcgcaaa | gagagggtgc | tgaacgttcc | gctttgcaag | 420 |
| gaggactgcg | agcaatggtg | ggaagactgt | agaaccagct | acacctgtaa | gtctaactgg | 480 |
| cacaaaggat | ggaactggac | atccgggttt | aacaaatgcg | ctgtcggcgc | tgcctgccag | 540 |
| ccatttcatt | tctactttcc | aactcccact | gtcctgtgta | acgagatttg | gacgcattca | 600 |
| tataaagtca | gcaactacag | ccggggctcc | ggccgctgca | ttcagatgtg | gttcgaccct | 660 |
| gcacagggca | accctaacga | ggaggtcgca | cgcttctacg | ctgcagcaat | gtctggagcc | 720 |
| ggtccttggg | ctgcttggcc | atttctcctt | agcctcgccc | tcatgcttct | ctggctgttg | 780 |
| tcataatcta | ga | | | | | 792 |

<210> SEQ ID NO 50
<211> LENGTH: 32
<212> TYPE: DNA
<213> ORGANISM: Artificial sequence
<220> FEATURE:
<223> OTHER INFORMATION: Primer EcoMH1
<220> FEATURE:
<221> NAME/KEY: misc_feature
<222> LOCATION: (13)..(13)
<223> OTHER INFORMATION: s is g or c
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (18)..(18)
<223> OTHER INFORMATION: n is g, a, t or c
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (25)..(25)
<223> OTHER INFORMATION: s is g or c
<220> FEATURE:
<221> NAME/KEY: misc_feature
<222> LOCATION: (28)..(28)
<223> OTHER INFORMATION: s is g or c

<400> SEQUENCE: 50
cttccggaat tcsargtnma gctgsagsag tc                                32

<210> SEQ ID NO 51
<211> LENGTH: 35
<212> TYPE: DNA

```
<213> ORGANISM: Artificial sequence
<220> FEATURE:
<223> OTHER INFORMATION: Primer EcoMH2
<220> FEATURE:
<221> NAME/KEY: misc_feature
<222> LOCATION: (13)..(13)
<223> OTHER INFORMATION: s is g or c
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (18)..(18)
<223> OTHER INFORMATION: n is g, a, t or c
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (25)..(25)
<223> OTHER INFORMATION: s is g or c
<220> FEATURE:
<221> NAME/KEY: misc_feature
<222> LOCATION: (28)..(28)
<223> OTHER INFORMATION: s is g or c
<220> FEATURE:
<221> NAME/KEY: misc_feature
<222> LOCATION: (33)..(33)
<223> OTHER INFORMATION: w is a or t

<400> SEQUENCE: 51
cttccggaat tcsargtnma gctgsagsag tcwgg                                 35

<210> SEQ ID NO 52
<211> LENGTH: 36
<212> TYPE: DNA
<213> ORGANISM: Artificial sequence
<220> FEATURE:
<223> OTHER INFORMATION: Primer BamIgG1

<400> SEQUENCE: 52
ggaggatcca tagacagatg ggggtgtcgt tttggc                                36

<210> SEQ ID NO 53
<211> LENGTH: 31
<212> TYPE: DNA
<213> ORGANISM: Artificial sequence
<220> FEATURE:
<223> OTHER INFORMATION: SacIMK
<220> FEATURE:
<221> NAME/KEY: misc_feature
<222> LOCATION: (10)..(10)
<223> OTHER INFORMATION: y is c or t
<220> FEATURE:
<221> NAME/KEY: misc_feature
<222> LOCATION: (17)..(17)
<223> OTHER INFORMATION: m is a or c
<220> FEATURE:
<221> NAME/KEY: misc_feature
<222> LOCATION: (19)..(19)
<223> OTHER INFORMATION: s is g or c
<220> FEATURE:
<221> NAME/KEY: misc_feature
<222> LOCATION: (22)..(22)
<223> OTHER INFORMATION: m is a or c
<220> FEATURE:
<221> NAME/KEY: misc_feature
<222> LOCATION: (25)..(25)
<223> OTHER INFORMATION: r is a or g
<220> FEATURE:
<221> NAME/KEY: misc_feature
<222> LOCATION: (26)..(26)
<223> OTHER INFORMATION: w is a or t
```

```
<220> FEATURE:
<221> NAME/KEY: misc_feature
<222> LOCATION: (29)..(29)
<223> OTHER INFORMATION: m is a or c

<400> SEQUENCE: 53
ggagctcgay attgtgmtsa cmcarwctmc a                                   31

<210> SEQ ID NO 54
<211> LENGTH: 46
<212> TYPE: DNA
<213> ORGANISM: Artificial sequence
<220> FEATURE:
<223> OTHER INFORMATION: HindKL

<400> SEQUENCE: 54
tatagagctc aagcttggat ggtgggaaga tggatacagt tggtgc                   46

<210> SEQ ID NO 55
<211> LENGTH: 39
<212> TYPE: DNA
<213> ORGANISM: Artificial sequence
<220> FEATURE:
<223> OTHER INFORMATION: cd37-1LClead

<400> SEQUENCE: 55
ttttgaattc gccaccatga agtttccttc tcaacttct                           39

<210> SEQ ID NO 56
<211> LENGTH: 17
<212> TYPE: PRT
<213> ORGANISM: Artificial sequence
<220> FEATURE:
<223> OTHER INFORMATION: human and chimeric Mov19 vHC CDR2 composite
<220> FEATURE:
<221> NAME/KEY: MISC_FEATURE
<222> LOCATION: (14)..(14)
<223> OTHER INFORMATION: Xaa can be Gln, His, Lys, or Arg
<220> FEATURE:
<221> NAME/KEY: MISC_FEATURE
<222> LOCATION: (16)..(16)
<223> OTHER INFORMATION: Xaa can be Arg, Gln, His, or Asn
<220> FEATURE:
<221> NAME/KEY: MISC_FEATURE
<222> LOCATION: (17)..(17)
<223> OTHER INFORMATION: Xaa can be Glu, Thr, Ser, Gly, Ala, or Val

<400> SEQUENCE: 56

Arg Ile His Pro Tyr Asp Gly Asp Thr Phe Tyr Asn Gln Xaa Phe Xaa
1               5                   10                  15

Xaa

<210> SEQ ID NO 57
<211> LENGTH: 11
<212> TYPE: PRT
<213> ORGANISM: Artificial sequence
<220> FEATURE:
<223> OTHER INFORMATION: FR1-48vL CDR1

<400> SEQUENCE: 57

Arg Ala Ser Glu Asn Ile Tyr Ser Asn Leu Ala
1               5                   10

<210> SEQ ID NO 58
<211> LENGTH: 7
<212> TYPE: PRT
<213> ORGANISM: Artificial sequence
<220> FEATURE:
```

<223> OTHER INFORMATION: FR1-48vL CDR2

<400> SEQUENCE: 58

Ala Ala Thr Asn Leu Ala Asp
1               5

<210> SEQ ID NO 59
<211> LENGTH: 9
<212> TYPE: PRT
<213> ORGANISM: Artificial sequence
<220> FEATURE:
<223> OTHER INFORMATION: FR1-48vL CDR3

<400> SEQUENCE: 59

Gln His Phe Trp Ala Ser Pro Tyr Thr
1               5

<210> SEQ ID NO 60
<211> LENGTH: 6
<212> TYPE: PRT
<213> ORGANISM: Artificial sequence
<220> FEATURE:
<223> OTHER INFORMATION: FR1-48vH CDR1

<400> SEQUENCE: 60

Thr Asn Tyr Trp Met Gln
1               5

<210> SEQ ID NO 61
<211> LENGTH: 10
<212> TYPE: PRT
<213> ORGANISM: Artificial sequence
<220> FEATURE:
<223> OTHER INFORMATION: FR1-48vH CDR2

<400> SEQUENCE: 61

Ala Ile Tyr Pro Gly Asn Gly Asp Ser Arg
1               5                   10

<210> SEQ ID NO 62
<211> LENGTH: 8
<212> TYPE: PRT
<213> ORGANISM: Artificial sequence
<220> FEATURE:
<223> OTHER INFORMATION: FR1-48vH CDR3

<400> SEQUENCE: 62

Arg Asp Gly Asn Tyr Ala Ala Tyr
1               5

<210> SEQ ID NO 63
<211> LENGTH: 11
<212> TYPE: PRT
<213> ORGANISM: Artificial sequence
<220> FEATURE:
<223> OTHER INFORMATION: FR1-49vL CDR1

<400> SEQUENCE: 63

Arg Ala Ser Glu Asn Ile Tyr Thr Asn Leu Ala
1               5                   10

<210> SEQ ID NO 64
<211> LENGTH: 7
<212> TYPE: PRT
<213> ORGANISM: Artificial sequence
<220> FEATURE:
<223> OTHER INFORMATION: FR1-49vL CDR2

<400> SEQUENCE: 64

Thr Ala Ser Asn Leu Ala Asp
1               5

<210> SEQ ID NO 65
<211> LENGTH: 9
<212> TYPE: PRT
<213> ORGANISM: Artificial sequence
<220> FEATURE:
<223> OTHER INFORMATION: FR1-49vL CDR3

<400> SEQUENCE: 65

Gln His Phe Trp Val Ser Pro Tyr Thr
1               5

<210> SEQ ID NO 66
<211> LENGTH: 6
<212> TYPE: PRT
<213> ORGANISM: Artificial sequence
<220> FEATURE:
<223> OTHER INFORMATION: FR1-49vH CDR1

<400> SEQUENCE: 66

Thr Asn Tyr Trp Met Tyr
1               5

<210> SEQ ID NO 67
<211> LENGTH: 10
<212> TYPE: PRT
<213> ORGANISM: Artificial sequence
<220> FEATURE:
<223> OTHER INFORMATION: FR1-49vH CDR2

<400> SEQUENCE: 67

Ala Ile Tyr Pro Gly Asn Ser Asp Thr Thr
1               5                   10

<210> SEQ ID NO 68
<211> LENGTH: 9
<212> TYPE: PRT
<213> ORGANISM: Artificial sequence
<220> FEATURE:
<223> OTHER INFORMATION: FR1-49vH CDR3

<400> SEQUENCE: 68

Arg His Asp Tyr Gly Ala Met Asp Tyr
1               5

<210> SEQ ID NO 69
<211> LENGTH: 11
<212> TYPE: PRT
<213> ORGANISM: Artificial sequence
<220> FEATURE:
<223> OTHER INFORMATION: FR1-57vL CDR1

<400> SEQUENCE: 69

Arg Ala Ser Gln Asn Ile Asn Asn Asn Leu His
1               5                   10

<210> SEQ ID NO 70
<211> LENGTH: 7
<212> TYPE: PRT
<213> ORGANISM: Artificial sequence
<220> FEATURE:
<223> OTHER INFORMATION: FR1-57vL CDR2

```
<400> SEQUENCE: 70

Tyr Val Ser Gln Ser Val Ser
1               5

<210> SEQ ID NO 71
<211> LENGTH: 10
<212> TYPE: PRT
<213> ORGANISM: Artificial sequence
<220> FEATURE:
<223> OTHER INFORMATION: FR1-57vL CDR3

<400> SEQUENCE: 71

Gln Gln Ser Asn Ser Trp Pro His Tyr Thr
1               5                   10

<210> SEQ ID NO 72
<211> LENGTH: 6
<212> TYPE: PRT
<213> ORGANISM: Artificial sequence
<220> FEATURE:
<223> OTHER INFORMATION: FR1-57vH CDR1

<400> SEQUENCE: 72

Ser Ser Phe Gly Met His
1               5

<210> SEQ ID NO 73
<211> LENGTH: 10
<212> TYPE: PRT
<213> ORGANISM: Artificial sequence
<220> FEATURE:
<223> OTHER INFORMATION: FR1-57vH CDR2

<400> SEQUENCE: 73

Tyr Ile Ser Ser Gly Ser Ser Thr Ile Ser
1               5                   10

<210> SEQ ID NO 74
<211> LENGTH: 9
<212> TYPE: PRT
<213> ORGANISM: Artificial sequence
<220> FEATURE:
<223> OTHER INFORMATION: FR1-57vH CDR3

<400> SEQUENCE: 74

Glu Ala Tyr Gly Ser Ser Met Glu Tyr
1               5

<210> SEQ ID NO 75
<211> LENGTH: 11
<212> TYPE: PRT
<213> ORGANISM: Artificial sequence
<220> FEATURE:
<223> OTHER INFORMATION: FR1-65vL CDR1

<400> SEQUENCE: 75

Lys Ala Ser Gln Asn Val Gly Pro Asn Val Ala
1               5                   10

<210> SEQ ID NO 76
<211> LENGTH: 7
<212> TYPE: PRT
<213> ORGANISM: Artificial sequence
<220> FEATURE:
<223> OTHER INFORMATION: FR1-65vL CDR2

<400> SEQUENCE: 76
```

```
Ser Ala Ser Tyr Arg Tyr Ser
1               5

<210> SEQ ID NO 77
<211> LENGTH: 9
<212> TYPE: PRT
<213> ORGANISM: Artificial sequence
<220> FEATURE:
<223> OTHER INFORMATION: FR1-65vL CDR3

<400> SEQUENCE: 77

Gln Gln Tyr Asn Ser Tyr Pro Tyr Thr
1               5

<210> SEQ ID NO 78
<211> LENGTH: 6
<212> TYPE: PRT
<213> ORGANISM: Artificial sequence
<220> FEATURE:
<223> OTHER INFORMATION: FR1-65vH CDR1

<400> SEQUENCE: 78

Thr Ser Tyr Thr Met His
1               5

<210> SEQ ID NO 79
<211> LENGTH: 10
<212> TYPE: PRT
<213> ORGANISM: Artificial sequence
<220> FEATURE:
<223> OTHER INFORMATION: FR1-65vH CDR2

<400> SEQUENCE: 79

Tyr Ile Asn Pro Ile Ser Gly Tyr Thr Asn
1               5                   10

<210> SEQ ID NO 80
<211> LENGTH: 11
<212> TYPE: PRT
<213> ORGANISM: Artificial sequence
<220> FEATURE:
<223> OTHER INFORMATION: FR1-65vH CDR3

<400> SEQUENCE: 80

Gly Gly Ala Tyr Gly Arg Lys Pro Met Asp Tyr
1               5                   10

<210> SEQ ID NO 81
<211> LENGTH: 17
<212> TYPE: PRT
<213> ORGANISM: Artificial sequence
<220> FEATURE:
<223> OTHER INFORMATION: muFR1-48 Kabat defined HC CDR2

<400> SEQUENCE: 81

Ala Ile Tyr Pro Gly Asn Gly Asp Ser Arg Tyr Thr Gln Lys Phe Lys
1               5                   10                  15

Gly

<210> SEQ ID NO 82
<211> LENGTH: 17
<212> TYPE: PRT
<213> ORGANISM: Artificial sequence
<220> FEATURE:
<223> OTHER INFORMATION: huFR1-48 Kabat defined HC CDR2
```

```
<400> SEQUENCE: 82

Ala Ile Tyr Pro Gly Asn Gly Asp Ser Arg Tyr Thr Gln Lys Phe Gln
1               5                   10                  15

Gly

<210> SEQ ID NO 83
<211> LENGTH: 17
<212> TYPE: PRT
<213> ORGANISM: Artificial sequence
<220> FEATURE:
<223> OTHER INFORMATION: huFR1-49 Kabat defined HC CDR2

<400> SEQUENCE: 83

Ala Ile Tyr Pro Gly Asn Ser Asp Thr Thr Tyr Asn Gln Lys Phe Gln
1               5                   10                  15

Gly

<210> SEQ ID NO 84
<211> LENGTH: 17
<212> TYPE: PRT
<213> ORGANISM: Artificial sequence
<220> FEATURE:
<223> OTHER INFORMATION: muFR1-57 Kabat defined HC CDR2

<400> SEQUENCE: 84

Tyr Ile Ser Ser Gly Ser Ser Thr Ile Ser Tyr Ala Asp Thr Val Lys
1               5                   10                  15

Gly

<210> SEQ ID NO 85
<211> LENGTH: 17
<212> TYPE: PRT
<213> ORGANISM: Artificial sequence
<220> FEATURE:
<223> OTHER INFORMATION: huFR1-57 Kabat defined HC CDR2

<400> SEQUENCE: 85

Tyr Ile Ser Ser Gly Ser Ser Thr Ile Ser Tyr Ala Asp Ser Val Lys
1               5                   10                  15

Gly

<210> SEQ ID NO 86
<211> LENGTH: 17
<212> TYPE: PRT
<213> ORGANISM: Artificial sequence
<220> FEATURE:
<223> OTHER INFORMATION: muFR1-65 Kabat defined HC CDR2

<400> SEQUENCE: 86

Tyr Ile Asn Pro Ile Ser Gly Tyr Thr Asn Tyr Asn Gln Lys Phe Lys
1               5                   10                  15

Asp

<210> SEQ ID NO 87
<211> LENGTH: 17
<212> TYPE: PRT
<213> ORGANISM: Artificial sequence
<220> FEATURE:
<223> OTHER INFORMATION: huFR1-65 Kabat defined HC CDR2

<400> SEQUENCE: 87

Tyr Ile Asn Pro Ile Ser Gly Tyr Thr Asn Tyr Asn Gln Lys Phe Gln
1               5                   10                  15
```

Gly

<210> SEQ ID NO 88
<211> LENGTH: 108
<212> TYPE: PRT
<213> ORGANISM: Artificial sequence
<220> FEATURE:
<223> OTHER INFORMATION: muFR1-48vL

<400> SEQUENCE: 88

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Glu Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Ala Ser Pro Tyr
                85                  90                  95

Thr Phe Gly Gly Gly Thr Lys Leu Glu Ile Lys Arg
            100                 105

<210> SEQ ID NO 89
<211> LENGTH: 117
<212> TYPE: PRT
<213> ORGANISM: Artificial sequence
<220> FEATURE:
<223> OTHER INFORMATION: muFR1-48vH

<400> SEQUENCE: 89

Gln Val Gln Leu Gln Gln Ser Gly Ala Glu Leu Ala Arg Pro Gly Ala
1               5                   10                  15

Ser Val Lys Leu Ser Cys Arg Ala Ser Gly Tyr Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asn Gly Asp Ser Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Val Ser Ser Leu Thr Ser Glu Asp Ser Ala Val Tyr Tyr Cys
                85                  90                  95

Ala Arg Arg Asp Gly Asn Tyr Ala Ala Tyr Trp Gly Gln Gly Thr Leu
            100                 105                 110

Val Thr Val Ser Ala
        115

<210> SEQ ID NO 90
<211> LENGTH: 108
<212> TYPE: PRT
<213> ORGANISM: Artificial sequence
<220> FEATURE:
<223> OTHER INFORMATION: muFR1-49vL

<400> SEQUENCE: 90

Asp Ile Gln Met Thr Gln Ser Pro Ala Ser Leu Ser Val Ser Val Gly

```
                1               5                   10                  15
            Glu Thr Val Thr Ile Thr Cys Arg Ala Ser Glu Asn Ile Tyr Thr Asn
                                20                  25                  30

Leu Ala Trp Tyr Gln Gln Lys Gln Gly Lys Ser Pro Gln Leu Leu Val
                        35                  40                  45

Tyr Thr Ala Ser Asn Leu Ala Asp Gly Val Pro Ser Arg Phe Ser Gly
                50                  55                  60

Ser Gly Ser Gly Thr Gln Tyr Ser Leu Lys Ile Asn Ser Leu Gln Ser
            65                  70                  75                  80

Glu Asp Phe Gly Thr Tyr Tyr Cys Gln His Phe Trp Val Ser Pro Tyr
                            85                  90                  95

Thr Phe Gly Gly Gly Thr Lys Leu Glu Ile Lys Arg
                            100                 105
```

<210> SEQ ID NO 91
<211> LENGTH: 118
<212> TYPE: PRT
<213> ORGANISM: Artificial sequence
<220> FEATURE:
<223> OTHER INFORMATION: muFR1-49vH

<400> SEQUENCE: 91

```
            Glu Val Gln Leu Gln Gln Ser Gly Thr Val Leu Ala Arg Pro Gly Ala
            1               5                   10                  15

Ser Val Lys Met Ser Cys Lys Ala Ser Gly Tyr Lys Phe Thr Asn Tyr
                            20                  25                  30

Trp Met Tyr Trp Ile Lys Gln Arg Pro Gly Gln Gly Leu Glu Leu Ile
                        35                  40                  45

Gly Ala Ile Tyr Pro Gly Asn Ser Asp Thr Thr Tyr Asn Leu Lys Phe
                50                  55                  60

Lys Gly Lys Ala Lys Leu Thr Ala Val Thr Ser Ala Asn Thr Val Tyr
            65                  70                  75                  80

Met Glu Val Ser Ser Leu Thr Asn Glu Asp Ser Ala Val Tyr Tyr Cys
                            85                  90                  95

Thr Lys Arg His Asp Tyr Gly Ala Met Asp Tyr Trp Gly Gln Gly Thr
                            100                 105                 110

Ser Val Thr Val Ser Ser
                    115
```

<210> SEQ ID NO 92
<211> LENGTH: 109
<212> TYPE: PRT
<213> ORGANISM: Artificial sequence
<220> FEATURE:
<223> OTHER INFORMATION: muFR1-57vL

<400> SEQUENCE: 92

```
            Asp Ile Val Leu Thr Gln Ser Pro Ala Thr Leu Ser Val Thr Pro Gly
            1               5                   10                  15

Asp Ser Val Ser Leu Ser Cys Arg Ala Ser Gln Asn Ile Asn Asn Asn
                            20                  25                  30

Leu His Trp Tyr Gln Gln Lys Ser His Glu Ser Pro Arg Leu Leu Ile
                        35                  40                  45

Lys Tyr Val Ser Gln Ser Val Ser Gly Ile Pro Ser Arg Phe Ser Gly
                50                  55                  60

Ser Gly Ser Gly Thr Asp Phe Thr Leu Ser Ile Asn Ser Val Glu Thr
            65                  70                  75                  80
```

```
Glu Asp Phe Gly Met Tyr Phe Cys Gln Gln Ser Asn Ser Trp Pro His
            85                  90                  95

Tyr Thr Phe Gly Gly Gly Thr Lys Leu Glu Ile Lys Arg
            100                 105

<210> SEQ ID NO 93
<211> LENGTH: 118
<212> TYPE: PRT
<213> ORGANISM: Artificial sequence
<220> FEATURE:
<223> OTHER INFORMATION: muFR1-57vH

<400> SEQUENCE: 93

Asp Val Gln Leu Val Glu Ser Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Ser Tyr Ala Asp Thr Val
        50                  55                  60

Lys Gly Arg Phe Thr Ile Ser Arg Asp Asn Ser Lys Lys Thr Leu Leu
65                  70                  75                  80

Leu Gln Met Thr Ser Leu Arg Ser Glu Asp Thr Ala Met Tyr Tyr Cys
                85                  90                  95

Ala Arg Glu Ala Tyr Gly Ser Ser Met Glu Tyr Trp Gly Gln Gly Thr
                100                 105                 110

Ser Val Thr Val Ser Ser
            115

<210> SEQ ID NO 94
<211> LENGTH: 108
<212> TYPE: PRT
<213> ORGANISM: Artificial sequence
<220> FEATURE:
<223> OTHER INFORMATION: muFR1-65vL

<400> SEQUENCE: 94

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Pro Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Glu Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Ala Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys Arg
            100                 105

<210> SEQ ID NO 95
<211> LENGTH: 120
<212> TYPE: PRT
<213> ORGANISM: Artificial sequence
<220> FEATURE:
<223> OTHER INFORMATION: muFR1-65vH
```

```
<400> SEQUENCE: 95

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Ala Trp Ile
        35                  40                  45

Gly Tyr Ile Asn Pro Ile Ser Gly Tyr Thr Asn Tyr Asn Gln Lys Phe
50                  55                  60

Lys Asp Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Gly Gly Ala Tyr Gly Arg Lys Pro Met Asp Tyr Trp Gly Gln
            100                 105                 110

Gly Thr Ser Val Thr Val Ser Ser
        115                 120

<210> SEQ ID NO 96
<211> LENGTH: 108
<212> TYPE: PRT
<213> ORGANISM: Artificial sequence
<220> FEATURE:
<223> OTHER INFORMATION: huFR1-48vL

<400> SEQUENCE: 96

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Ala Ala Thr Asn Leu Ala Asp Gly Val Pro Ser Arg Phe Ser Gly
50                  55                  60

Ser Glu Ser Gly Thr Asp Tyr Ser Leu Lys Ile Asn Ser Leu Gln Pro
65                  70                  75                  80

Glu Asp Phe Gly Ser Tyr Tyr Cys Gln His Phe Trp Ala Ser Pro Tyr
                85                  90                  95

Thr Phe Gly Gln Gly Thr Lys Leu Glu Ile Lys Arg
            100                 105

<210> SEQ ID NO 97
<211> LENGTH: 117
<212> TYPE: PRT
<213> ORGANISM: Artificial sequence
<220> FEATURE:
<223> OTHER INFORMATION: huFR1-48vH

<400> SEQUENCE: 97

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asn Gly Asp Ser Arg Tyr Thr Gln Lys Phe
50                  55                  60
```

-continued

Gln Gly Lys Ala Thr Leu Thr Ala Asp Lys Ser Ser Thr Ala Tyr
65                  70                  75                  80

Met Gln Val Ser Ser Leu Thr Ser Glu Asp Ser Ala Val Tyr Tyr Cys
                85                  90                  95

Ala Arg Arg Asp Gly Asn Tyr Ala Ala Tyr Trp Gly Gln Gly Thr Leu
            100                 105                 110

Val Thr Val Ser Ala
        115

<210> SEQ ID NO 98
<211> LENGTH: 108
<212> TYPE: PRT
<213> ORGANISM: Artificial sequence
<220> FEATURE:
<223> OTHER INFORMATION: huFR1-49vL

<400> SEQUENCE: 98

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Tyr Thr Asn
            20                  25                  30

Leu Ala Trp Tyr Gln Gln Lys Pro Gly Lys Ser Pro Lys Leu Leu Val
        35                  40                  45

Tyr Thr Ala Ser Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Phe Trp Val Ser Pro Tyr
                85                  90                  95

Thr Phe Gly Gln Gly Thr Lys Leu Glu Ile Lys Arg
            100                 105

<210> SEQ ID NO 99
<211> LENGTH: 118
<212> TYPE: PRT
<213> ORGANISM: Artificial sequence
<220> FEATURE:
<223> OTHER INFORMATION: huFR1-49vH

<400> SEQUENCE: 99

Gln Val Gln Leu Gln Gln Ser Gly Ala Val Ala Lys Pro Gly Ala
1               5                   10                  15

Ser Val Lys Met Ser Cys Lys Ala Ser Gly Tyr Thr Phe Thr Asn Tyr
            20                  25                  30

Trp Met Tyr Trp Ile Lys Gln Arg Pro Gly Gln Gly Leu Glu Leu Ile
        35                  40                  45

Gly Ala Ile Tyr Pro Gly Asn Ser Asp Thr Thr Tyr Asn Gln Lys Phe
    50                  55                  60

Gln Gly Lys Ala Thr Leu Thr Ala Val Thr Ser Ala Asn Thr Val Tyr
65                  70                  75                  80

Met Glu Val Ser Ser Leu Thr Ser Glu Asp Ser Ala Val Tyr Tyr Cys
                85                  90                  95

Thr Lys Arg His Asp Tyr Gly Ala Met Asp Tyr Trp Gly Gln Gly Thr
            100                 105                 110

Ser Val Thr Val Ser Ser
        115

<210> SEQ ID NO 100

<211> LENGTH: 109
<212> TYPE: PRT
<213> ORGANISM: Artificial sequence
<220> FEATURE:
<223> OTHER INFORMATION: huFR1-57vL

<400> SEQUENCE: 100

```
Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
            20                  25                  30

Leu His Trp Tyr Gln Gln Lys Pro Gly Gln Ser Pro Arg Leu Leu Ile
        35                  40                  45

Lys Tyr Val Ser Gln Ser Val Ser Gly Ile Pro Asp Arg Phe Ser Gly
50                  55                  60

Ser Gly Ser Gly Thr Asp Phe Thr Leu Ser Ile Ser Val Glu Pro
65                  70                  75                  80

Glu Asp Phe Gly Met Tyr Phe Cys Gln Gln Ser Asn Ser Trp Pro His
                85                  90                  95

Tyr Thr Phe Gly Gln Gly Thr Lys Leu Glu Ile Lys Arg
            100                 105
```

<210> SEQ ID NO 101
<211> LENGTH: 118
<212> TYPE: PRT
<213> ORGANISM: Artificial sequence
<220> FEATURE:
<223> OTHER INFORMATION: huFR1-57vH

<400> SEQUENCE: 101

```
Glu Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Ser Tyr Ala Asp Ser Val
50                  55                  60

Lys Gly Arg Phe Thr Ile Ser Arg Asp Asn Ser Lys Lys Thr Leu Leu
65                  70                  75                  80

Leu Gln Met Thr Ser Leu Arg Ala Glu Asp Thr Ala Met Tyr Tyr Cys
                85                  90                  95

Ala Arg Glu Ala Tyr Gly Ser Ser Met Glu Tyr Trp Gly Gln Gly Thr
            100                 105                 110

Leu Val Thr Val Ser Ser
        115
```

<210> SEQ ID NO 102
<211> LENGTH: 108
<212> TYPE: PRT
<213> ORGANISM: Artificial sequence
<220> FEATURE:
<223> OTHER INFORMATION: huFR1-65vL

<400> SEQUENCE: 102

```
Glu Ile Val Met Thr Gln Ser Pro Ala Thr Met Ser Thr Ser Pro Gly
1               5                   10                  15

Asp Arg Val Ser Val Thr Cys Lys Ala Ser Gln Asn Val Gly Pro Asn
            20                  25                  30
```

```
Val Ala Trp Tyr Gln Gln Lys Pro Gly Gln Ser Pro Arg Ala Leu Ile
            35                  40                  45

Tyr Ser Ala Ser Tyr Arg Tyr Ser Gly Val Pro Ala Arg Phe Thr Gly
 50                  55                  60

Ser Gly Ser Gly Thr Asp Phe Thr Leu Thr Ile Ser Asn Met Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Gln Gly Thr Lys Leu Glu Ile Lys Arg
                100                 105
```

<210> SEQ ID NO 103
<211> LENGTH: 120
<212> TYPE: PRT
<213> ORGANISM: Artificial sequence
<220> FEATURE:
<223> OTHER INFORMATION: huFR1-65vH

<400> SEQUENCE: 103

```
Gln Val Gln Leu Val Gln Ser Gly Ala Glu Val Ala Lys Pro Gly Ala
 1               5                  10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Ala Trp Ile
            35                  40                  45

Gly Tyr Ile Asn Pro Ile Ser Gly Tyr Thr Asn Tyr Asn Gln Lys Phe
 50                  55                  60

Gln Gly Lys Ala Thr Leu Thr Ala Asp Lys Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Ser Gly Gly Ala Tyr Gly Arg Lys Pro Met Asp Tyr Trp Gly Gln
                100                 105                 110

Gly Thr Ser Val Thr Val Ser Ser
            115                 120
```

<210> SEQ ID NO 104
<211> LENGTH: 214
<212> TYPE: PRT
<213> ORGANISM: Artificial sequence
<220> FEATURE:
<223> OTHER INFORMATION: muFR1-48LC

<400> SEQUENCE: 104

```
Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
 50                  55                  60

Ser Glu Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Ala Ser Pro Tyr
                 85                  90                  95

Thr Phe Gly Gly Gly Thr Lys Leu Glu Ile Lys Arg Ala Asp Ala Ala
                100                 105                 110
```

```
Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 105
<211> LENGTH: 441
<212> TYPE: PRT
<213> ORGANISM: Artificial sequence
<220> FEATURE:
<223> OTHER INFORMATION: muFR1-48HC

<400> SEQUENCE: 105

```
Gln Val Gln Leu Gln Gln Ser Gly Ala Glu Leu Ala Arg Pro Gly Ala
1               5                   10                  15

Ser Val Lys Leu Ser Cys Arg Ala Ser Gly Tyr Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asn Gly Asp Ser Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Val Ser Ser Leu Thr Ser Glu Asp Ser Ala Val Tyr Tyr Cys
                85                  90                  95

Ala Arg Arg Asp Gly Asn Tyr Ala Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Ser Val Thr Val Pro Ser Ser Met Arg
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255
```

```
Val Val Asp Ile Ser Lys Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
            355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asn Thr Asn Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
            435                 440

<210> SEQ ID NO 106
<211> LENGTH: 214
<212> TYPE: PRT
<213> ORGANISM: Artificial sequence
<220> FEATURE:
<223> OTHER INFORMATION: muFR1-49LC

<400> SEQUENCE: 106

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Thr Asn
            20                  25                  30

Leu Ala Trp Tyr Gln Gln Lys Gln Gly Lys Ser Pro Gln Leu Leu Val
        35                  40                  45

Tyr Thr Ala Ser Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Val Ser Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175
```

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 107
<211> LENGTH: 448
<212> TYPE: PRT
<213> ORGANISM: Artificial sequence
<220> FEATURE:
<223> OTHER INFORMATION: muFR1-49HC

<400> SEQUENCE: 107

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Lys Phe Thr Asn Tyr
            20                  25                  30

Trp Met Tyr Trp Ile Lys Gln Arg Pro Gly Gln Gly Leu Glu Leu Ile
        35                  40                  45

Gly Ala Ile Tyr Pro Gly Asn Ser Asp Thr Thr Tyr Asn Leu Lys Phe
    50                  55                  60

Lys Gly Lys Ala Lys Leu Thr Ala Val Thr Ser Ala Asn Thr Val Tyr
65                  70                  75                  80

Met Glu Val Ser Ser Leu Thr Asn Glu Asp Ser Ala Val Tyr Tyr Cys
                85                  90                  95

Thr Lys Arg His Asp Tyr Gly Ala Met Asp Tyr Trp Gly Gln Gly Thr
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

```
Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445
```

<210> SEQ ID NO 108
<211> LENGTH: 215
<212> TYPE: PRT
<213> ORGANISM: Artificial sequence
<220> FEATURE:
<223> OTHER INFORMATION: muFR1-57LC

<400> SEQUENCE: 108

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Asn Ile Asn Asn Asn
                20                  25                  30

Leu His Trp Tyr Gln Gln Lys Ser His Glu Ser Pro Arg Leu Leu Ile
            35                  40                  45

Lys Tyr Val Ser Gln Ser Val Ser Gly Ile Pro Ser Arg Phe Ser Gly
        50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro His
                85                  90                  95

Tyr Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
        210                 215
```

<210> SEQ ID NO 109

<211> LENGTH: 448
<212> TYPE: PRT
<213> ORGANISM: Artificial sequence
<220> FEATURE:
<223> OTHER INFORMATION: muFR1-57HC

<400> SEQUENCE: 109

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Ser Tyr Ala Asp Thr Val
    50                  55                  60

Lys Gly Arg Phe Thr Ile Ser Arg Asp Asn Ser Lys Lys Thr Leu Leu
65                  70                  75                  80

Leu Gln Met Thr Ser Leu Arg Ser Glu Asp Thr Ala Met Tyr Tyr Cys
                85                  90                  95

Ala Arg Glu Ala Tyr Gly Ser Ser Met Glu Tyr Trp Gly Gln Gly Thr
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380
```

```
Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445
```

<210> SEQ ID NO 110
<211> LENGTH: 214
<212> TYPE: PRT
<213> ORGANISM: Artificial sequence
<220> FEATURE:
<223> OTHER INFORMATION: muFR1-65LC

<400> SEQUENCE: 110

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Pro Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Glu Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Ala Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 111
<211> LENGTH: 444
<212> TYPE: PRT
<213> ORGANISM: Artificial sequence
<220> FEATURE:
<223> OTHER INFORMATION: muFR1-65HC

<400> SEQUENCE: 111

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
```

-continued

```
                20                  25                  30
Thr Met His Trp Val Lys Gln Arg Pro Gly Gln Gly Leu Ala Trp Ile
         35                  40                  45
Gly Tyr Ile Asn Pro Ile Ser Gly Tyr Thr Asn Tyr Asn Gln Lys Phe
     50                  55                  60
Lys Asp Lys Ala Thr Leu Thr Ala Asp Lys Ser Ser Thr Ala Tyr
 65                  70                  75                  80
Met Gln Leu Asn Ser Leu Thr Ser Glu Asp Ser Ala Val Tyr Tyr Cys
                 85                  90                  95
Ala Ser Gly Gly Ala Tyr Gly Arg Lys Pro Met Asp Tyr Trp Gly Gln
                100                 105                 110
Gly Thr Ser Val Thr Val Ser Ser Ala Lys Thr Thr Pro Pro Ser Val
             115                 120                 125
Tyr Pro Leu Ala Pro Gly Ser Ala Ala Gln Thr Asn Ser Met Val Thr
             130                 135                 140
Leu Gly Cys Leu Val Lys Gly Tyr Phe Pro Glu Pro Val Thr Val Thr
145                 150                 155                 160
Trp Asn Ser Gly Ser Leu Ser Ser Gly Val His Thr Phe Pro Ala Val
                 165                 170                 175
Leu Glu Ser Asp Leu Tyr Thr Leu Ser Ser Ser Val Thr Val Pro Ser
             180                 185                 190
Ser Met Arg Pro Ser Glu Thr Val Thr Cys Asn Val Ala His Pro Ala
             195                 200                 205
Ser Ser Thr Lys Val Asp Lys Lys Ile Val Pro Arg Asp Cys Gly Cys
         210                 215                 220
Lys Pro Cys Ile Cys Thr Val Pro Glu Val Ser Ser Val Phe Ile Phe
225                 230                 235                 240
Pro Pro Lys Pro Lys Asp Val Leu Thr Ile Thr Leu Thr Pro Lys Val
                 245                 250                 255
Thr Cys Val Val Val Asp Ile Ser Lys Asp Asp Pro Glu Val Gln Phe
             260                 265                 270
Ser Trp Phe Val Asp Asp Val Glu Val His Thr Ala Gln Thr Gln Pro
         275                 280                 285
Arg Glu Glu Gln Phe Asn Ser Thr Phe Arg Ser Val Ser Glu Leu Pro
    290                 295                 300
Ile Met His Gln Asp Trp Leu Asn Gly Lys Glu Phe Lys Cys Arg Val
305                 310                 315                 320
Asn Ser Ala Ala Phe Pro Ala Pro Ile Glu Lys Thr Ile Ser Lys Thr
                 325                 330                 335
Lys Gly Arg Pro Lys Ala Pro Gln Val Tyr Thr Ile Pro Pro Pro Lys
             340                 345                 350
Glu Gln Met Ala Lys Asp Lys Val Ser Leu Thr Cys Met Ile Thr Asp
             355                 360                 365
Phe Phe Pro Glu Asp Ile Thr Val Glu Trp Gln Trp Asn Gly Gln Pro
         370                 375                 380
Ala Glu Asn Tyr Lys Asn Thr Gln Pro Ile Met Asn Thr Asn Gly Ser
385                 390                 395                 400
Tyr Phe Val Tyr Ser Lys Leu Asn Val Gln Lys Ser Asn Trp Glu Ala
                 405                 410                 415
Gly Asn Thr Phe Thr Cys Ser Val Leu His Glu Gly Leu His Asn His
             420                 425                 430
His Thr Glu Lys Ser Leu Ser His Ser Pro Gly Lys
         435                 440
```

```
<210> SEQ ID NO 112
<211> LENGTH: 214
<212> TYPE: PRT
<213> ORGANISM: Artificial sequence
<220> FEATURE:
<223> OTHER INFORMATION: huFR1-48LC

<400> SEQUENCE: 112

Asp Ile Gln Met Thr Gln Ser Pro Ser Ser Leu Ser Val Ser Val Gly
 1               5                  10                  15

Glu Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Ala Ala Thr Asn Leu Ala Asp Gly Val Pro Ser Arg Phe Ser Gly
    50                  55                  60

Ser Glu Ser Gly Thr Asp Tyr Ser Leu Lys Ile Asn Ser Leu Gln Pro
65                  70                  75                  80

Glu Asp Phe Gly Ser Tyr Tyr Cys Gln His Phe Trp Ala Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 113
<211> LENGTH: 446
<212> TYPE: PRT
<213> ORGANISM: Artificial sequence
<220> FEATURE:
<223> OTHER INFORMATION: huFR1-48HC

<400> SEQUENCE: 113

Gln Val Gln Leu Val Gln Ser Gly Ala Glu Val Ala Lys Pro Gly Ala
 1               5                  10                  15

Ser Val Lys Leu Ser Cys Lys Ala Ser Gly Tyr Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asn Gly Asp Ser Arg Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Val Ser Ser Leu Thr Ser Glu Asp Ser Ala Val Tyr Tyr Cys
```

```
            85                  90                  95
Ala Arg Arg Asp Gly Asn Tyr Ala Ala Tyr Trp Gly Gln Gly Thr Leu
            100                 105                 110

Val Thr Val Ser Ala Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 114
<211> LENGTH: 214
<212> TYPE: PRT
<213> ORGANISM: Artificial sequence
<220> FEATURE:
<223> OTHER INFORMATION: huFR1-49LC

<400> SEQUENCE: 114

Asp Ile Gln Met Thr Gln Ser Pro Ser Ser Leu Ser Val Ser Val Gly
```

```
  1               5                  10                 15
Glu Arg Val Thr Ile Thr Cys Arg Ala Ser Glu Asn Ile Tyr Thr Asn
                20                 25                 30
Leu Ala Trp Tyr Gln Gln Lys Pro Gly Lys Ser Pro Lys Leu Leu Val
                35                 40                 45
Tyr Thr Ala Ser Asn Leu Ala Asp Gly Val Pro Ser Arg Phe Ser Gly
                50                 55                 60
Ser Gly Ser Gly Thr Asp Tyr Ser Leu Lys Ile Asn Ser Leu Gln Pro
 65                 70                 75                 80
Glu Asp Phe Gly Thr Tyr Tyr Cys Gln His Phe Trp Val Ser Pro Tyr
                85                 90                 95
Thr Phe Gly Gln Gly Thr Lys Leu Glu Ile Lys Arg Thr Val Ala Ala
               100                105                110
Pro Ser Val Phe Ile Phe Pro Pro Ser Asp Glu Gln Leu Lys Ser Gly
               115                120                125
Thr Ala Ser Val Val Cys Leu Leu Asn Asn Phe Tyr Pro Arg Glu Ala
               130                135                140
Lys Val Gln Trp Lys Val Asp Asn Ala Leu Gln Ser Gly Asn Ser Gln
145                150                155                160
Glu Ser Val Thr Glu Gln Asp Ser Lys Asp Ser Thr Tyr Ser Leu Ser
               165                170                175
Ser Thr Leu Thr Leu Ser Lys Ala Asp Tyr Glu Lys His Lys Val Tyr
               180                185                190
Ala Cys Glu Val Thr His Gln Gly Leu Ser Ser Pro Val Thr Lys Ser
               195                200                205
Phe Asn Arg Gly Glu Cys
210

<210> SEQ ID NO 115
<211> LENGTH: 447
<212> TYPE: PRT
<213> ORGANISM: Artificial sequence
<220> FEATURE:
<223> OTHER INFORMATION: huFR1-49HC

<400> SEQUENCE: 115

Gln Val Gln Leu Gln Gln Ser Gly Ala Val Ala Lys Pro Gly Ala
 1               5                  10                 15
Ser Val Lys Met Ser Cys Lys Ala Ser Gly Tyr Thr Phe Thr Asn Tyr
                20                 25                 30
Trp Met Tyr Trp Ile Lys Gln Arg Pro Gly Gln Gly Leu Glu Leu Ile
                35                 40                 45
Gly Ala Ile Tyr Pro Gly Asn Ser Asp Thr Thr Tyr Asn Gln Lys Phe
                50                 55                 60
Gln Gly Lys Ala Thr Leu Thr Ala Val Thr Ser Ala Asn Thr Val Tyr
 65                 70                 75                 80
Met Glu Val Ser Ser Leu Thr Ser Glu Asp Ser Ala Val Tyr Tyr Cys
                85                 90                 95
Thr Lys Arg His Asp Tyr Gly Ala Met Asp Tyr Trp Gly Gln Gly Thr
               100                105                110
Ser Val Thr Val Ser Ser Ala Ser Thr Lys Gly Pro Ser Val Phe Pro
               115                120                125
Leu Ala Pro Ser Ser Lys Ser Thr Ser Gly Gly Thr Ala Ala Leu Gly
               130                135                140
Cys Leu Val Lys Asp Tyr Phe Pro Glu Pro Val Thr Val Ser Trp Asn
```

```
                145                 150                 155                 160
        Ser Gly Ala Leu Thr Ser Gly Val His Thr Phe Pro Ala Val Leu Gln
                        165                 170                 175

Ser Ser Gly Leu Tyr Ser Leu Ser Ser Val Val Thr Val Pro Ser Ser
                        180                 185                 190

Ser Leu Gly Thr Gln Thr Tyr Ile Cys Asn Val Asn His Lys Pro Ser
                        195                 200                 205

Asn Thr Lys Val Asp Lys Lys Val Glu Pro Lys Ser Cys Asp Lys Thr
                        210                 215                 220

His Thr Cys Pro Pro Cys Pro Ala Pro Glu Leu Leu Gly Gly Pro Ser
        225                 230                 235                 240

Val Phe Leu Phe Pro Pro Lys Pro Lys Asp Thr Leu Met Ile Ser Arg
                        245                 250                 255

Thr Pro Glu Val Thr Cys Val Val Val Asp Val Ser His Glu Asp Pro
                        260                 265                 270

Glu Val Lys Phe Asn Trp Tyr Val Asp Gly Val Glu Val His Asn Ala
                        275                 280                 285

Lys Thr Lys Pro Arg Glu Glu Gln Tyr Asn Ser Thr Tyr Arg Val Val
                        290                 295                 300

Ser Val Leu Thr Val Leu His Gln Asp Trp Leu Asn Gly Lys Glu Tyr
        305                 310                 315                 320

Lys Cys Lys Val Ser Asn Lys Ala Leu Pro Ala Pro Ile Glu Lys Thr
                        325                 330                 335

Ile Ser Lys Ala Lys Gly Gln Pro Arg Glu Pro Gln Val Tyr Thr Leu
                        340                 345                 350

Pro Pro Ser Arg Asp Glu Leu Thr Lys Asn Gln Val Ser Leu Thr Cys
                        355                 360                 365

Leu Val Lys Gly Phe Tyr Pro Ser Asp Ile Ala Val Glu Trp Glu Ser
                        370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Lys Leu Thr Val Asp Lys Ser
                        405                 410                 415

Arg Trp Gln Gln Gly Asn Val Phe Ser Cys Ser Val Met His Glu Ala
                        420                 425                 430

Leu His Asn His Tyr Thr Gln Lys Ser Leu Ser Leu Ser Pro Gly
                        435                 440                 445

<210> SEQ ID NO 116
<211> LENGTH: 215
<212> TYPE: PRT
<213> ORGANISM: Artificial sequence
<220> FEATURE:
<223> OTHER INFORMATION: huFR1-57LC

<400> SEQUENCE: 116

Glu Ile Val Leu Thr Gln Ser Pro Ala Thr Leu Ser Val Thr Pro Gly
        1               5                   10                  15

Asp Arg Val Ser Leu Ser Cys Arg Ala Ser Gln Asn Ile Asn Asn Asn
                        20                  25                  30

Leu His Trp Tyr Gln Gln Lys Pro Gly Gln Ser Pro Arg Leu Leu Ile
                        35                  40                  45

Lys Tyr Val Ser Gln Ser Val Ser Gly Ile Pro Asp Arg Phe Ser Gly
                        50                  55                  60

Ser Gly Ser Gly Thr Asp Phe Thr Leu Ser Ile Ser Ser Val Glu Pro
```

```
                65                  70                  75                  80
Glu Asp Phe Gly Met Tyr Phe Cys Gln Gln Ser Asn Ser Trp Pro His
                    85                  90                  95

Tyr Thr Phe Gly Gln Gly Thr Lys Leu Glu Ile Lys Arg Thr Val Ala
                100                 105                 110

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 117
<211> LENGTH: 447
<212> TYPE: PRT
<213> ORGANISM: Artificial sequence
<220> FEATURE:
<223> OTHER INFORMATION: huFR1-57HC

<400> SEQUENCE: 117

Glu Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Tyr Ile Ser Ser Gly Ser Ser Thr Ile Ser Tyr Ala Asp Ser Val
        50                  55                  60

Lys Gly Arg Phe Thr Ile Ser Arg Asp Asn Ser Lys Lys Thr Leu Leu
65                  70                  75                  80

Leu Gln Met Thr Ser Leu Arg Ala Glu Asp Thr Ala Met Tyr Tyr Cys
                85                  90                  95

Ala Arg Glu Ala Tyr Gly Ser Ser Met Glu Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

```
                    210                 215                 220
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                    245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445
```

<210> SEQ ID NO 118
<211> LENGTH: 214
<212> TYPE: PRT
<213> ORGANISM: Artificial sequence
<220> FEATURE:
<223> OTHER INFORMATION: huFR1-65LC

<400> SEQUENCE: 118

```
Glu Ile Val Met Thr Gln Ser Pro Ala Thr Met Ser Thr Ser Pro Gly
1               5                   10                  15

Asp Arg Val Ser Val Thr Cys Lys Ala Ser Gln Asn Val Gly Pro Asn
                20                  25                  30

Val Ala Trp Tyr Gln Gln Lys Pro Gly Gln Ser Pro Arg Ala Leu Ile
                35                  40                  45

Tyr Ser Ala Ser Tyr Arg Tyr Ser Gly Val Pro Ala Arg Phe Thr Gly
                50                  55                  60

Ser Gly Ser Gly Thr Asp Phe Thr Leu Thr Ile Ser Asn Met Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
```

130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 119
<211> LENGTH: 449
<212> TYPE: PRT
<213> ORGANISM: Artificial sequence
<220> FEATURE:
<223> OTHER INFORMATION: huFR1-65HC

<400> SEQUENCE: 119

Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Ala Trp Ile
            35                  40                  45

Gly Tyr Ile Asn Pro Ile Ser Gly Tyr Thr Asn Tyr Asn Gln Lys Phe
    50                  55                  60

Gln Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Gly Gly Ala Tyr Gly Arg Lys Pro Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His

|   | 275 |   |   |   | 280 |   |   |   | 285 |   |   |   |
|---|---|---|---|---|---|---|---|---|---|---|---|---|

Asn Ala Lys Thr Lys Pro Arg Glu Glu Gln Tyr Asn Ser Thr Tyr Arg
   290                       295                       300

Val Val Ser Val Leu Thr Val Leu His Gln Asp Trp Leu Asn Gly Lys
305                       310                       315                    320

Glu Tyr Lys Cys Lys Val Ser Asn Lys Ala Leu Pro Ala Pro Ile Glu
                 325                       330                       335

Lys Thr Ile Ser Lys Ala Lys Gly Gln Pro Arg Glu Pro Gln Val Tyr
          340                       345                     350

Thr Leu Pro Pro Ser Arg Asp Glu Leu Thr Lys Asn Gln Val Ser Leu
               355                       360                     365

Thr Cys Leu Val Lys Gly Phe Tyr Pro Ser Asp Ile Ala Val Glu Trp
   370                     375                       380

Glu Ser Asn Gly Gln Pro Glu Asn Asn Tyr Lys Thr Thr Pro Pro Val
385                       390                       395                    400

Leu Asp Ser Asp Gly Ser Phe Phe Leu Tyr Ser Lys Leu Thr Val Asp
                 405                       410                     415

Lys Ser Arg Trp Gln Gln Gly Asn Val Phe Ser Cys Ser Val Met His
          420                       425                     430

Glu Ala Leu His Asn His Tyr Thr Gln Lys Ser Leu Ser Leu Ser Pro
               435                       440                     445

Gly

<210> SEQ ID NO 120
<211> LENGTH: 396
<212> TYPE: DNA
<213> ORGANISM: Artificial sequence
<220> FEATURE:
<223> OTHER INFORMATION: huFR1-48_VL

<400> SEQUENCE: 120

```
gaattcgcca ccatgggatg gagttgtatc atcctgtttc ttgtggctac agccacaggg    60
gtacactccg atattcaaat gacacagtcc ccttcatccc tgtccgtcag tgtgggggaa   120
agggttacca tcacctgccg tgcatcagag aacatctatt ccaacctcgc ctggtaccaa   180
cagaaacctg gcaagtcccc taagctgttg gtctacgccg ctacaaacct cgccgatggg   240
gtgccttccc gtttcagtgg gtcagagtca ggcaccgact attctctgaa gatcaactcc   300
ctccagcctg aggatttcgg ctcctattac tgtcagcact ctgggctag  tccatatact   360
ttcggccagg gaaccaaact tgaaattaaa cgtacg                             396
```

<210> SEQ ID NO 121
<211> LENGTH: 437
<212> TYPE: DNA
<213> ORGANISM: Artificial sequence
<220> FEATURE:
<223> OTHER INFORMATION: huFR1-48_VH

<400> SEQUENCE: 121

```
aagcttgcca ccatggggtg gagctgcatc atcctttttc tggtggccac tgccaccggc    60
gtgcactctc aggtccaact tgtgcagagc ggagccgagg tggccaaacc cggagctagt   120
gttaagctct catgtaaagc atctggctac acctttacta actactggat gcagtggatc   180
aagcaacggc aggccaggg cctggagtgg attggtgcta tttatcccgg aaacggggat   240
agcaggtaca ctcagaaatt tcagggaaag gctaccctta ccgccgataa gagttcttcc   300
acagcatata tgcaagtctc ctctctgacc tcagaggata tgctgtctcta ttactgcgct   360
```

```
cgccgggatg caactatgc agcctattgg ggtcaaggca cccttgtgac tgtatccgca    420
gcaagcacca agggccc                                                  437

<210> SEQ ID NO 122
<211> LENGTH: 396
<212> TYPE: DNA
<213> ORGANISM: Artificial sequence
<220> FEATURE:
<223> OTHER INFORMATION: huFR1-49_VL

<400> SEQUENCE: 122
gaattcgcca ccatgggttg gtcatgcatt atcctgtttc tggtcgcaac agcaacaggt    60
gtgcacagtg acattcagat gacccaaagc ccctccagtc tgagcgtttc cgtggggaa    120 cgtgtcacta tcacatgcag agcttccgag aatatttaca ctaacctcgc atggtaccag   180
cagaaacccg ggaagtctcc aaaacttctc gtatatacag ccagcaactt ggcagatggg   240
gtgcccagcc ggtttagcgg atctggttca ggcaccgact attctttgaa aattaattcc   300
ctgcagcctg aggattttgg tacctactat tgccagcatt tttgggtatc accatacact   360
tttggacagg gaacaaagct ggagatcaag cgtacg                             396

<210> SEQ ID NO 123
<211> LENGTH: 440
<212> TYPE: DNA
<213> ORGANISM: Artificial sequence
<220> FEATURE:
<223> OTHER INFORMATION: huFR1-49_VH

<400> SEQUENCE: 123
aagcttgcca ccatgggctg gtcttgtatt attcttttc ttgtggccac agccacagga    60
gtccattcac aggtacagct ccaacagtct ggcgcagttg tcgccaagcc cggcgcctct   120
gtgaagatga gttgcaaggc ctctggctac accttcacta attattggat gtactggatc   180
aaacaacgcc ccggccaggg tctggaactc attggagcca tctacccagg caactccgac   240
acaacataca atcagaagtt tcagggcaaa gcaaccctga ccgctgtaac ctcagctaat   300
accgtgtaca tggaggtaag tagcttgact agtgaagatt ccgcagtata ctattgcacc   360
aagcgccatg attacggcgc catggattac tggggccaag gtaccagtgt gaccgtgtct   420
tccgcttcca ccaagggccc                                               440

<210> SEQ ID NO 124
<211> LENGTH: 399
<212> TYPE: DNA
<213> ORGANISM: Artificial sequence
<220> FEATURE:
<223> OTHER INFORMATION: huFR1-57_VL

<400> SEQUENCE: 124
gaattcgcca ccatgggctg gtcatgcatt attttgttcc tggtcgccac cgcaaccggc    60
gttcattccg aaattgttct tactcagagc cctgcaacct gagtgtgac acccggcgat   120 cgggtctcac tgagttgcag agcttcccag aatatcaaca ataatctgca ctggtatcag   180
cagaagcctg gccagtctcc tcgcttgctg attaagtatg tctcacagag cgtgtcaggt   240
atccctgacc gtttctccgg gtcaggttca ggcaccgact tcacactgtc catttctagc   300
gtggagcctg aggatttcgg aatgtacttt tgccagcaga gcaatagctg gcctcactac   360 accttttggcc aagggaccaa gctggagatc aagcgtacg                         399
```

<210> SEQ ID NO 125
<211> LENGTH: 440
<212> TYPE: DNA
<213> ORGANISM: Artificial sequence
<220> FEATURE:
<223> OTHER INFORMATION: huFR1-57_VH

<400> SEQUENCE: 125

```
aagcttgcca ccatgggctg gagctgtatc atcttgttcc ttgtggccac agctactggc    60
gtgcactccg aggtgcagct ggtcgaatcc ggcggaggcc tggtgcagcc tggggggagt   120
agacggctgt cctgcgctgc ctctgggttt actttctcaa gtttcggtat gcactgggtg   180
cgtcaggccc ccgggaaggg cctggaatgg gttgcttata tatcatctgg cagctccacc   240
atttcttatg ctgattccgt taagggacgc ttcaccattt ccagagacaa cagtaagaaa   300
acccttctgc tgcagatgac ctctctccgc gccgaagaca ccgcaatgta ttattgtgct   360
agagaggcct acggcagtag tatgaatac tggggcagg ggaccctggt gaccgtgtct    420
tccgcatcta ctaagggccc                                               440
```

<210> SEQ ID NO 126
<211> LENGTH: 396
<212> TYPE: DNA
<213> ORGANISM: Artificial sequence
<220> FEATURE:
<223> OTHER INFORMATION: huFR1-65_VL

<400> SEQUENCE: 126

```
gaattcgcca ccatgggctg gtcttgcatt attctgttcc tggttgcaac agccactggc    60
gtccattccg aaatcgtgat gacccaatct cccgccacca tgtctacctc tccggggac   120
cgggtgtctg tgacctgcaa ggcctctcag aatgttggcc aaacgtggc atggtatcaa   180
cagaaaccag gcagtcacc cagagccctg atttactccg cttcttacag atattcagga   240
gttcccgccc ggttcacagg tagtgggtcc ggcactgact ttaccttgac catttccaac   300
atgcaatccg aggacctggc cgaatacttc tgtcagcagt acaattcata tccctataca   360
ttcggccagg ggaccaagct ggaaataaag cgtacg                             396
```

<210> SEQ ID NO 127
<211> LENGTH: 446
<212> TYPE: DNA
<213> ORGANISM: Artificial sequence
<220> FEATURE:
<223> OTHER INFORMATION: huFR1-65_VH

<400> SEQUENCE: 127

```
aagcttgcca ccatgggctg gtcatgcata atcctgttcc tggtcgcaac cgctacaggt    60
gtacactccc aggtgcagtt ggtgcagagc ggggccgaag ttgctaagcc cggtgcaagt   120
gtaaaaatgt cctgcaaagc tagcgggtac acattcacat cctatactat gcattgggta   180
aaacagcgcc caggacaggg gctcgcctgg ataggctata ttaacccaat atcaggatac   240
acaaactaca atcagaaatt tcagggaaag gcaaccctga ccgccgacaa gtcctcttct   300
accgcatata tgcagctcaa ctccctgacc agtgaagata cgcagtgta ttactgtgcc    360
tccggcggtg cttatggccg gaaacccatg gattactggg gacaaggcac ctccgtcaca   420
gtgagtagcg cctcaaccaa gggccc                                         446
```

<210> SEQ ID NO 128
<211> LENGTH: 17

```
<212> TYPE: PRT
<213> ORGANISM: Artificial sequence
<220> FEATURE:
<223> OTHER INFORMATION: Kabat Defined Mov19 HC CDR2 Murine

<400> SEQUENCE: 128

Arg Ile His Pro Tyr Asp Gly Asp Thr Phe Tyr Asn Gln Asn Phe Lys
1               5                   10                  15
Asp

<210> SEQ ID NO 129
<211> LENGTH: 17
<212> TYPE: PRT
<213> ORGANISM: Artificial sequence
<220> FEATURE:
<223> OTHER INFORMATION: Kabat Defined Mov19 HC CDR2 Human

<400> SEQUENCE: 129

Arg Ile His Pro Tyr Asp Gly Asp Thr Phe Tyr Asn Gln Lys Phe Gln
1               5                   10                  15
Gly

<210> SEQ ID NO 130
<211> LENGTH: 17
<212> TYPE: PRT
<213> ORGANISM: Artificial sequence
<220> FEATURE:
<223> OTHER INFORMATION: muFR1-49 Kabat defined HC CDR2

<400> SEQUENCE: 130

Ala Ile Tyr Pro Gly Asn Ser Asp Thr Thr Tyr Asn Leu Lys Phe Lys
1               5                   10                  15
Gly

<210> SEQ ID NO 131
<211> LENGTH: 10
<212> TYPE: PRT
<213> ORGANISM: Artificial Sequence
<220> FEATURE:
<223> OTHER INFORMATION: huMov19 vHC CDR2

<400> SEQUENCE: 131

Arg Ile His Pro Tyr Asp Gly Asp Thr Phe
1               5                   10
```

US 9,133,275 B2

FOLATE RECEPTOR 1 ANTIBODIES AND IMMUNOCONJUGATES AND USES THEREOF

CROSS REFERENCE TO RELATED APPLICATIONS

This application is a divisional application of U.S. application Ser. No. 13/033,723, filed Feb. 24, 2011, which claims the priority benefit of U.S. Provisional Application No. 61/307,797, filed Feb. 24, 2010, U.S. Provisional Application No. 61/346,595, filed May 20, 2010, and U.S. Provisional Application No. 61/413,172, filed Nov. 12, 2010, each of which is hereby incorporated by reference herein in its entirety.

FIELD OF THE INVENTION

The field of this invention generally relates to antibodies and immunoconjugates that bind to human folate receptor 1, as well as to methods of using the antibodies and immunoconjugates for the treatment of diseases, such as cancer.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, Cancer J. Clin. 53:5-26).

Folate Receptor 1 (FOLR1), also known as Folate Receptor-alpha, or Folate Binding Protein, is an N-glycosylated protein expressed on plasma membrane of cells. FOLR1 has a high affinity for folic acid and for several reduced folic acid derivatives. FOLR1 mediates delivery of the physiological folate, 5-methyltetrahydrofolate, to the interior of cells.

FOLR1 is overexpressed in vast majority of ovarian cancers, as well as in many uterine, endometrial, pancreatic, renal, lung, and breast cancers, while the expression of FOLR1 on normal tissues is restricted to the apical membrane of epithelial cells in the kidney proximal tubules, alveolar pneumocytes of the lung, bladder, testes, choroid plexus, and thyroid (Weitman S D, et al., Cancer Res 52: 3396-3401 (1992); Antony A C, Annu Rev Nutr 16: 501-521 (1996); Kalli K R, et al. Gynecol Oncol 108: 619-626 (2008)). This expression pattern of FOLR1 makes it a desirable target for FOLR1-directed cancer therapy.

Because ovarian cancer is typically asymptomatic until advanced stage, it is often diagnosed at a late stage and has poor prognosis when treated with currently available procedures, typically chemotherapeutic drugs after surgical debulking (von Gruenigen V et al., Cancer 112: 2221-2227 (2008); Ayhan A et al., Am J Obstet Gynecol 196: 81 e81-86 (2007); Harry V N et al., Obstet Gynecol Surv 64: 548-560 (2009)). Thus there is a clear unmet medical need for more effective therapeutics for ovarian cancers.

Three anti-FOLR1 antibodies have been examined as potential anti-cancer drugs. Murine monoclonal antibodies Mov18 and Mov19 were isolated in the late 1980s (Miotti S et al., Int J Cancer 39: 297-303 (1987)), confirmed to target FOLR1 (Coney L R et al., Cancer Res 51: 6125-6132 (1991)), and tested in pre-clinical studies for their ability to eradicate antigen-expressing cancer cells as conjugates with a cytotoxic ribosome-inactivating protein (Conde F P et al., Eur J Biochem 178: 795-802 (1989)).

Mov19 was tested as a bi-specific antibody targeting cytotoxic T cells and natural killer cells (Mezzanzanica D et al., Int J Cancer 41: 609-615 (1988); Ferrini S et al., Int J Cancer Suppl 4: 53-55 (1989); Ferrini S et al., Int J Cancer 48: 227-233 (1991)), and as a fusion protein of the single-chain Fv (scFv) of Mov19 with interleukin-2 in vivo (Melani C et al., Cancer Res 58: 4146-4154 (1998)). Chimeric (murine variable/human constant) anti-FOLR1 antibodies Mov18 and Mov19 have been examined pre-clinically on their ability to mediate cytotoxic immune cell-dependent killing of FOLR1-expressing tumor cells in vitro (Coney L R et al., Cancer Res 54: 2448-2455 (1994)), and a chimeric Mov18-IgE was tested in IgE-dependent immunotherapeutic preclinical models (Karagiannis S N et al., J Immunol 179: 2832-2843 (2007); Gould H J et al., Eur J Immunol 29: 3527-3537 (1999)).

Mov18 was studied in the form of conjugates with various radionuclides in preclinical studies and then, in early 1990s, in clinical trials (Zacchetti A et al., Nucl Med Biol 36: 759-770 (2009)), which ended without any drug being approved for clinical use.

MORAb003, a humanized form of the murine monoclonal anti-FOLR1 antibody LK26 was evaluated pre-clinically as a non-modified antibody (Ebel W et al., Cancer Immun 7:6 (2007)) and as a conjugate with the $^{111}$In radionuclide (Smith-Jones P M et al., Nucl Med Biol 35: 343-351 (2008)), and is currently undergoing clinical trials as a non-modified antibody (D. K. Armstrong et al. J. Clin. Oncol. 26: 2008, May 20 suppl; abstract 5500).

SUMMARY OF THE INVENTION

The present invention provides novel antibodies that bind to human folate receptor 1, immunoconjugates comprising these antibodies, and methods of their use. The present invention further provides novel polypeptides, such as antibodies that bind human folate receptor 1, fragments of such antibodies, and other polypeptides related to such antibodies. Polynucleotides comprising nucleic acid sequences encoding the polypeptides are also provided, as are vectors comprising the polynucleotides. Cells comprising the polypeptides and/or polynucleotides of the invention are further provided. Compositions (e.g., pharmaceutical compositions) comprising the novel folate receptor 1 antibodies or immunoconjugates are also provided. In addition, methods of making and using the novel folate receptor 1 antibodies or immunoconjugates are also provided, such as methods of using the novel folate receptor 1 antibodies or immunoconjugates to inhibit tumor growth and/or treat cancer.

Thus, in one aspect, the invention provides a humanized antibody or antigen binding fragment thereof that specifically binds a human folate receptor 1, wherein the antibody comprises (a) a heavy chain CDR1 comprising GYFMN (SEQ ID NO:1); a heavy chain CDR2 comprising RIHPYDGDTFYNQXaa$_1$FXaa$_2$Xaa$_3$ (SEQ ID NO:56); and a heavy chain CDR3 comprising YDGSRAMDY (SEQ ID NO:3); and (b) a light chain CDR1 comprising KASQSVS-FAGTSLMH (SEQ ID NO:7); a light chain CDR2 comprising RASNLEA (SEQ ID NO:8); and a light chain CDR3 comprising QQSREYPYT (SEQ ID NO:9); wherein Xaa$_1$ is selected from K, Q, H, and R; Xaa$_2$ is selected from Q, H, N, and R; and Xaa$_3$ is selected from G, E, T, S, A, and V. In a certain embodiment, the humanized antibody or antigen binding fragment thereof binds a human folate receptor 1 with substantially the same affinity as the antibody chimeric Mov19. In a certain embodiment, the humanized antibody or antigen binding fragment thereof comprises the heavy chain CDR2 sequence RIHPYDGDTFYNQKFQG (SEQ ID NO:2).

In a certain embodiment, the binding affinity is measured by flow cytometry, Biacore, or radioimmunoassay.

In another embodiment, the invention provides a humanized antibody or antigen binding fragment thereof that specifically binds a human folate receptor 1, wherein the antibody comprises: (a) a heavy chain CDR1 comprising GYFMN (SEQ ID NO:1), or a variant thereof comprising 1, 2, 3, or 4 conservative amino acid substitutions; a heavy chain CDR2 comprising RIHPYDGDTFYNQKFQG (SEQ ID NO:2), or a variant thereof comprising 1, 2, 3, or 4 amino conservative acid substitutions; and a heavy chain CDR3 comprising YDGSRAMDY (SEQ ID NO:3), or a variant thereof comprising 1, 2, 3, or 4 conservative amino acid substitutions; and/or (b) a light chain CDR1 comprising KASQSVSFAGTSLMH (SEQ ID NO:7), or a variant thereof comprising 1, 2, 3, or 4 conservative amino acid substitutions; a light chain CDR2 comprising RASNLEA (SEQ ID NO:8), or a variant thereof comprising 1, 2, 3, or 4 conservative amino acid substitutions; and a light chain CDR3 comprising QQSREYPYT (SEQ ID NO:9), or a variant thereof comprising 1, 2, 3, or 4 conservative amino acid substitutions.

In a certain embodiment, the invention provides a humanized antibody or antigen binding fragment thereof that specifically binds the human folate receptor 1 comprising the heavy chain of SEQ ID NO:6. In another embodiment, the humanized antibody or antigen binding fragment thereof is encoded by the plasmid DNA deposited with the ATCC on Apr. 7, 2010 and having ATCC deposit nos. PTA-10772 and PTA-10773 or 10774.

In a certain embodiment, the invention provides a humanized antibody or antigen binding fragment thereof that competes for binding to FOLR1 with an antibody comprising (a) a heavy chain CDR1 comprising GYFMN (SEQ ID NO:1); a heavy chain CDR2 comprising RIHPYDGDTFYNQXaa$_1$FXaa$_2$Xaa$_3$ (SEQ ID NO:56); and a heavy chain CDR3 comprising YDGSRAMDY (SEQ ID NO:3); and (b) a light chain CDR1 comprising KASQSVSFAGTSLMH (SEQ ID NO:7); a light chain CDR2 comprising RASNLEA (SEQ ID NO:8); and a light chain CDR3 comprising QQSREYPYT (SEQ ID NO:9); wherein Xaa$_1$ is selected from K, Q, H, and R; Xaa$_2$ is selected from Q, H, N, and R; and Xaa$_3$ is selected from G, E, T, S, A, and V. In a certain embodiment, the humanized antibody comprises the heavy chain CDR2 sequence RIHPYDGDTFYNQKFQG (SEQ ID NO:2).

In a certain embodiment, the invention provides a polypeptide, humanized antibody or antigen binding fragment thereof comprising a heavy chain variable domain at least about 90% identical to SEQ ID NO:4, and a light chain variable domain at least about 90% identical to SEQ ID NO:10 or SEQ ID NO:11. In another embodiment, the humanized antibody or antigen binding fragment comprises a heavy chain variable domain at least about 95% identical to SEQ ID NO:4, and a light chain variable domain at least about 95% identical to SEQ ID NO:10 or SEQ ID NO:11. In a further embodiment, the humanized antibody comprises a heavy chain variable domain at least about 99% identical to SEQ ID NO:4, and a light chain variable domain at least about 99% identical to SEQ ID NO:10 or SEQ ID NO:11. In a certain embodiment, the humanized antibody comprises the heavy chain variable domain of SEQ ID NO:4, and the light chain variable domain of SEQ ID NO:10 or SEQ ID NO:11. In certain embodiments, the invention provides a polypeptide, antibody, or antigen binding fragment at least about 90% identical to SEQ ID NOs: 88-119. In certain embodiments, the invention provides a polypeptide, antibody, or antigen binding fragment at least about 95% identical to SEQ ID NOs: 88-119. In certain embodiments, the invention provides a polypeptide, antibody, or antigen binding fragment at least about 99% identical to SEQ ID NOs: 88-119.

In a certain embodiment, the invention provides a humanized antibody or antigen binding fragment thereof that is expressed at least ten-fold higher than chMov19 in eukaryotic cells. In a certain embodiment, the eukaryotic cells are HEK-293T cells.

In certain embodiments, the invention provides an antibody or antigen binding fragment thereof that specifically binds a human folate receptor 1, wherein the antibody comprises: (a) a heavy chain CDR1 comprising SSYGMS (SEQ ID NO:30); a heavy chain CDR2 comprising TISSGGSYTY (SEQ ID NO:31); and/or a heavy chain CDR3 comprising DGEGGLYAMDY (SEQ ID NO:32); and/or (b) a light chain CDR1 comprising KASDHINNWLA (SEQ ID NO:27); a light chain CDR2 comprising GATSLET (SEQ ID NO:28); and a light chain CDR3 comprising QQYWSTPFT (SEQ ID NO:29). In another embodiment, the invention provides an antibody or antigen binding fragment thereof that specifically binds a human folate receptor 1, wherein the antibody comprises: (a) a heavy chain CDR1 comprising TNYWMQ (SEQ ID NO:60); a heavy chain CDR2 comprising AIYPGNGDSR (SEQ ID NO:61); and/or a heavy chain CDR3 comprising RDGNYAAY (SEQ ID NO:62); and/or (b) a light chain CDR1 comprising RASENIYSNLA (SEQ ID NO:57); a light chain CDR2 comprising AATNLAD (SEQ ID NO:58); and a light chain CDR3 comprising QHFWASPYT (SEQ ID NO:59). In another embodiment, the invention provides an antibody or antigen binding fragment thereof that specifically binds a human folate receptor 1, wherein the antibody comprises: (a) a heavy chain CDR1 comprising TNYWMY (SEQ ID NO:66); a heavy chain CDR2 comprising AIYPGNSDTT (SEQ ID NO:67); and/or a heavy chain CDR3 comprising RHDYGAMDY (SEQ ID NO:68); and/or (b) a light chain CDR1 comprising RASENIYTNLA (SEQ ID NO:63); a light chain CDR2 comprising TASNLAD (SEQ ID NO:64); and a light chain CDR3 comprising QHFWVSPYT (SEQ ID NO:65). In another embodiment, the invention provides an antibody or antigen binding fragment thereof that specifically binds a human folate receptor 1, wherein the antibody comprises: (a) a heavy chain CDR1 comprising SSFGMH (SEQ ID NO:72); a heavy chain CDR2 comprising YISSGSSTIS (SEQ ID NO:73); and/or a heavy chain CDR3 comprising EAYGSSMEY (SEQ ID NO:74); and/or (b) a light chain CDR1 comprising RASQNINNNLH (SEQ ID NO:69); a light chain CDR2 comprising YVSQSVS (SEQ ID NO:70); and a light chain CDR3 comprising QQSNSWPHYT (SEQ ID NO:71). In another embodiment, the invention provides an antibody or antigen binding fragment thereof that specifically binds a human folate receptor 1, wherein the antibody comprises: (a) a heavy chain CDR1 comprising TSYTMH (SEQ ID NO:78); a heavy chain CDR2 comprising YINPISGYTN (SEQ ID NO:79); and/or a heavy chain CDR3 comprising GGAYGRKPMDY (SEQ ID NO:80); and/or (b) a light chain CDR1 comprising KASQNVGPNVA (SEQ ID NO:75); a light chain CDR2 comprising SASYRYS (SEQ ID NO:76); and a light chain CDR3 comprising QQYNSYPYT (SEQ ID NO:77).

In certain embodiments, the polypeptides of the invention are full-length antibodies or antigen binding fragments. In certain embodiments, the antibodies or antigen binding fragments are a Fab, a Fab', a F(ab')2, a Fd, a single chain Fv or scFv, a disulfide linked Fv, a V NAR domain, a IgNar, an intrabody, an IgG-CH2, a minibody, a F(ab')3, a tetrabody, a triabody, a diabody, a single-domain antibody, DVD-Ig, Fcab, mAb2, a (scFv)2, or a scFv-Fc.

In certain embodiments, an antibody or polypeptide of the invention binds to a human folate receptor 1 with a Kd of about 1.0 to about 10 nM. In one embodiment, the antibody or polypeptide binds to a human folate receptor 1 with a Kd of about 1.0 nM or better. In a certain embodiment, binding affinity is measured by flow cytometry, Biacore, or radioimmunoassay.

The invention also provides a method of making an antibody of the invention comprising culturing a cell expressing said antibody; and (b) isolating the antibody from said cultured cell. In a certain embodiment, the cell is a eukaryotic cell.

The invention also provides an immunoconjugate having the formula (A)-(L)-(C), wherein: (A) is an antibody or antigen binding fragment or polypeptide of the invention; (L) is a linker; and (C) is a cytotoxic agent, wherein said linker (L) links (A) to (C).

In one embodiment, the linker is selected from the group of a cleavable linker, a non-cleavable linker, a hydrophilic linker, and a dicarboxylic acid based linker. In a further embodiment, the linker is selected from the group consisting of: N-succinimidyl 4-(2-pyridyldithio)pentanoate (SPP) or N-succinimidyl 4-(2-pyridyldithio)-2-sulfopentanoate (sulfo-SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl) cyclohexanecarboxylate (SMCC); N-sulfosuccinimidyl 4-(maleimidomethyl)cyclohexanecarboxylate (sulfoS-MCC); N-succinimidyl-4-(iodoacetyl)-aminobenzoate (SIAB); and N-succinimidyl-[(N-maleimidopropionamido)-tetraethyleneglycol]ester (NHS-PEG4-maleimide). In a certain embodiment, the linker is N-succinimidyl-[(N-maleimidopropionamido)-tetraethyleneglycol]ester (NHS-PEG4-maleimide).

In one embodiment, the immunoconjugates comprise a cytotoxic agent selected from the group of a maytansinoid, maytansinoid analog, benzodiazepine, taxoid, CC-1065, CC-1065 analog, duocarmycin, duocarmycin analog, calicheamicin, dolastatin, dolastatin analog, auristatin, tomaymycin derivative, and leptomycin derivative or a prodrug of the agent. In a further embodiment, the cytotoxic agent is a maytansinoid. In another embodiment, the cytotoxic agent is N(2')-deacetyl-N(2')-(3-mercapto-1-oxopropyl)-maytansine or N(2')-deacetyl-N2-(4-mercapto-4-methyl-1-oxopentyl)-maytansine.

In one embodiment the invention provides an immunoconjugate comprising: (A) a humanized antibody comprising the heavy chain variable domain of SEQ ID NO:4, and the light chain variable domain of SEQ ID NO:10 or SEQ ID NO:11; (L) N-succinimidyl-[(N-maleimidopropionamido)-tetraethyleneglycol]ester (NHS-PEG4-maleimide); and (C) N(2')-deacetyl-N2-(4-mercapto-4-methyl-1-oxopentyl)-maytansine; wherein (L) links (A) to (C).

In one embodiment the invention provides an immunoconjugate comprising: (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)butanoate (SPDB); and (C) N(2')-deacetyl-N2-(4-mercapto-4-methyl-1-oxopentyl)-maytansine; wherein (L) links (A) to (C).

In one embodiment the invention provides an immunoconjugate comprising: (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)2-sulfobutanoate (sulfo-SPDB); and (C) N(2')-deacetyl-N2-(4-mercapto-4-methyl-1-oxopentyl)-maytansine; wherein (L) links (A) to (C).

In one embodiment the invention provides an immunoconjugate comprising: (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)-2-sulfopentanoate (sulfo-SPP); and (C) N(2')-deacetyl-N(2')-(3-mercapto-1-oxopropyl)-maytansine; wherein (L) links (A) to (C).

In one embodiment the invention provides an immunoconjugate comprising: (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)pentanoate (SPP); and (C) N(2')-deacetyl-N(2')-(3-mercapto-1-oxopropyl)-maytansine; wherein (L) links (A) to (C).

The invention also provides a pharmaceutical composition comprising an antibody, antigen binding fragment, polypeptide, or immunoconjugate of the invention and a pharmaceutically acceptable carrier. In a certain embodiment, the pharmaceutical composition further comprises a second anti-cancer agent.

The invention also provides a diagnostic reagent comprising an antibody, antigen binding fragment, polypeptide, or immunoconjugate of the invention which is labeled. In one embodiment, the label is selected from the group of a radiolabel, a fluorophore, a chromophore, an imaging agent and a metal ion.

The invention also provides a kit comprising the antibody, antigen binding fragment, polypeptide, or immunoconjugate of the invention.

The invention also provides a method of inhibiting tumor growth in a subject, comprising administering a therapeutically effective amount of the antibody, antigen binding fragment, polypeptide, immunoconjugate, or pharmaceutical composition of the invention to the subject. In a certain embodiment, the invention provides a method of inhibiting tumor growth in a subject comprising administering a therapeutically effective amount of an immunoconjugate having the formula (A)-(L)-(C), wherein: (A) is an antibody or antigen binding fragment thereof that specifically binds a human folate receptor 1; (L) is a linker; and (C) is a cytotoxin selected from the group consisting of a maytansinoid and a maytansinoid analog; wherein (L) links (A) to (C) and wherein the immunoconjugate reduces mean tumor volume at least two-fold in a KB xenograft model. In a certain embodiment, the method comprises administering an antibody or antigen binding fragment thereof that comprises (a) a heavy chain CDR1 comprising GYFMN (SEQ ID NO:1); a heavy chain CDR2 comprising RIHPYDGDTFYNQX$aa_1$FX$aa_2$X$aa_3$ (SEQ ID NO:56); and a heavy chain CDR3 comprising YDGSRAMDY (SEQ ID NO:3); and (b) a light chain CDR1 comprising KASQSVSFAGTSLMH (SEQ ID NO:7); a light chain CDR2 comprising RASNLEA (SEQ ID NO:8); and a light chain CDR3 comprising QQSREYPYT (SEQ ID NO:9); wherein $Xaa_1$ is selected from K, Q, H, and R; $Xaa_2$ is selected from Q, H, N, and R; and $Xaa_3$ is selected from G, E, T, S, A, and V. In a further embodiment, the antibody comprises a heavy chain CDR2 comprising RIHPYDGDTFYNQKFQG (SEQ ID NO:2).

In a certain embodiment, the invention provides a method for inhibiting tumor growth comprising administering an antibody or antigen binding fragment thereof encoded by the plasmid DNA deposited with the ATCC on Apr. 7, 2010 and having ATCC deposit nos. PTA-10772 and PTA-10773 or 10774.

In another embodiment, the method provides administering an immunoconjugate comprising a humanized antibody comprising the heavy chain variable domain of SEQ ID NO:4, and the light chain variable domain of SEQ ID NO:10 or SEQ ID NO:11; (L) N-succinimidyl-[(N-maleimidopropionamido)-tetraethyleneglycol]ester (NHS-PEG4-maleimide); and (C) N(2')-deacetyl-N2-(4-mercapto-4-methyl-1-oxopentyl)-maytansine.

In another embodiment, the method comprises administering an immunoconjugate which comprises (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)butanoate (SPDB); and (C) N(2')-deacetyl-N2-(4-mercapto-4-methyl-1-oxopentyl)-maytansine; wherein (L) links (A) to (C).

In another embodiment, the method comprises administering an immunoconjugate which comprises (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)2-sulfobutanoate (sulfo-SPDB); and (C) N(2')-deacetyl-N2-(4-mercapto-4-methyl-1-oxopentyl)-maytansine; wherein (L) links (A) to (C).

In another embodiment, the method comprises administering an immunoconjugate which comprises (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)-2-sulfopentanoate (sulfo-SPP); and (C) N(2')-deacetyl-N(2')-(3-mercapto-1-oxopropyl)-maytansine; wherein (L) links (A) to (C).

In another embodiment, the method comprises administering an immunoconjugate which comprises (A) a humanized antibody comprising the heavy chain variable domain of SEQ ID NO:4, and the light chain variable domain of SEQ ID NO:10 or SEQ ID NO:11; (L) N-succinimidyl 4-(2-pyridyldithio)pentanoate (SPP); and (C) N(2')-deacetyl-N(2')-(3-mercapto-1-oxopropyl)-maytansine; wherein (L) links (A) to (C).

In another embodiment, the method comprises administering an immunoconjugate which comprises the antibody huFR-1-21 deposited with ATCC on Apr. 7, 2010 and having ATCC deposit nos. PTA-10775 and PTA-10776. In a certain embodiment, the huFR1-21 antibody comprises (a) a heavy chain CDR1 comprising SSYGMS (SEQ ID NO:30); a heavy chain CDR2 comprising TISSGGSYTY (SEQ ID NO:31); and a heavy chain CDR3 comprising DGEGGLYAMDY (SEQ ID NO:32); and (b) a light chain CDR1 comprising KASDHINNWLA (SEQ ID NO:27); a light chain CDR2 comprising GATSLET (SEQ ID NO:28); and a light chain CDR3 comprising QQYWSTPFT (SEQ ID NO:29). In certain embodiments the method comprises administering an immunoconjugate which comprises the antibody is the huFR1-48 antibody which comprises: (a) a heavy chain CDR1 comprising TNYWMQ (SEQ ID NO:60); a heavy chain CDR2 comprising AIYPGNGDSR (SEQ ID NO:61); and a heavy chain CDR3 comprising RDGNYAAY (SEQ ID NO:62); and (b) a light chain CDR1 comprising RASENIYSNLA (SEQ ID NO:57); a light chain CDR2 comprising AATNLAD (SEQ ID NO:58); and a light chain CDR3 comprising QHFWASPYT (SEQ ID NO:59). In certain embodiments the method comprises administering an immunoconjugate which comprises the antibody is the huFR1-49 antibody which comprises: (a) a heavy chain CDR1 comprising TNYWMY (SEQ ID NO:66); a heavy chain CDR2 comprising AIYPGNSDTT (SEQ ID NO:67); and a heavy chain CDR3 comprising RHDYGAMDY (SEQ ID NO:68); and (b) a light chain CDR1 comprising RASENIYTNLA (SEQ ID NO:63); a light chain CDR2 comprising TASNLAD (SEQ ID NO:64); and a light chain CDR3 comprising QHFWVSPYT (SEQ ID NO:65). In certain embodiments the method comprises administering an immunoconjugate which comprises the antibody is the huFR1-57 antibody which comprises: (a) a heavy chain CDR1 comprising SSFGMH (SEQ ID NO:72); a heavy chain CDR2 comprising YISSGSSTIS (SEQ ID NO:73); and a heavy chain CDR3 comprising EAYGSSMEY (SEQ ID NO:74); and (b) a light chain CDR1 comprising RASQNINNNLH (SEQ ID NO:69); a light chain CDR2 comprising YVSQSVS (SEQ ID NO:70); and a light chain CDR3 comprising QQSNSWPHYT (SEQ ID NO:71). In certain embodiments the method comprises administering an immunoconjugate which comprises the antibody is the huFR1-65 antibody which comprises: (a) a heavy chain CDR1 comprising TSYTMH (SEQ ID NO:78); a heavy chain CDR2 comprising YINPISGYTN (SEQ ID NO:79); and a heavy chain CDR3 comprising GGAYGRKPMDY (SEQ ID NO:80); and (b) a light chain CDR1 comprising KASQNVGPNVA (SEQ ID NO:75); a light chain CDR2 comprising SASYRYS (SEQ ID NO:76); and a light chain CDR3 comprising QQYNSYPYT (SEQ ID NO:77).

In one embodiment, the method inhibits ovarian tumor, brain tumor, breast tumor, uterine tumor, endometrial tumor, pancreatic tumor, renal tumor, or lung tumor growth. In a certain embodiment, the method inhibits ovarian tumor growth. In another embodiment, the invention inhibits lung tumor growth. In a certain embodiment, tumor growth inhibition is used to treat cancer. In a further embodiment, the method comprises administering a second anti-cancer agent to the subject. In a certain embodiment, the second anti-cancer agent is a chemotherapeutic agent.

The invention also provides an isolated cell producing the antibody, antigen binding fragment, or polypeptide of the invention.

The invention also provides an isolated polynucleotide comprising a sequence at least 90% identical to a sequence selected from the group consisting of SEQ ID NOs: 5, 14, 15, 37, 38, 43, 44, 47, 48, and 120-127. In a certain embodiment, the isolated polynucleotide is at least 95% identical a sequence selected from the group consisting of SEQ ID NOs: 5, 14, 15, 37, 38, 43, 44, 47, 48, and 120-127. In another embodiment, isolated polynucleotide is at least 99% identical to a sequence selected from the group consisting of SEQ ID NOs: 5, 14, 15, 37, 38, 43, 44, 47, 48, and 120-127. The invention also provides a vector comprising any of the polynucleotides of SEQ ID NOs: 5, 14, 15, 37, 38, 43, 44, 47, 48, and 120-127. In another embodiment, the invention provides a host cell comprising a vector which contains a polynucleotide of SEQ ID NOs: 5, 14, 15, 37, 38, 43, 44, 47, 48, and 120-127.

BRIEF DESCRIPTIONS OF THE DRAWINGS

FIG. 1. Surface residues for murine (muMov19) and humanized (huMov19) Mov19. (A) Murine and humanized Mov19 light chain surface residues. The murine and humanized Mov19 light chain variable region frame surface residues and position number (Kabat system) are given. The human residues that are different from the original murine sequences are underlined. *Position 74 is not a surface position, but to remove a consensus N-linked glycosylation site in version 1.00, this position was changed to a Threonine (the most common human residue in this position), resulting in version 1.60. (B) Murine and Human Mov19 Heavy Chain Surface Residues. The murine and humanized Mov19 heavy chain variable region frame surface residues and position number (Kabat system) are given. The human residues that are different from the original murine sequences are underlined. Similar surface residues are provided for FR1-21 (C) and (D).

FIG. 2. Alignments of chimeric Mov19 and huMov19 heavy and light chain variable domains and muFR1-21 and huFR1-21 heavy and light chain variable domains. Alignment of resurfaced sequences for the Mov19 and Fr1-21 variable regions with their murine counterparts. A) and C) light chain variable domains; B) and D) heavy chain variable domain. Dashes "-" denote identity with the murine sequence. The CDRs (Kabat definition) are underlined.

FIG. 3. Expression of chimeric Mov19 and huMov19 in HEK cells. The chimeric and human Mov19 expression plasmids were transiently transfected into suspension HEK293-T cells, harvested 7 days later, and the expressed antibody was determined by quantitative ELISA. The light chain and heavy chain plasmids were transfected at either 3:1 or 6:1 respective molar ratios.

Figure 4:
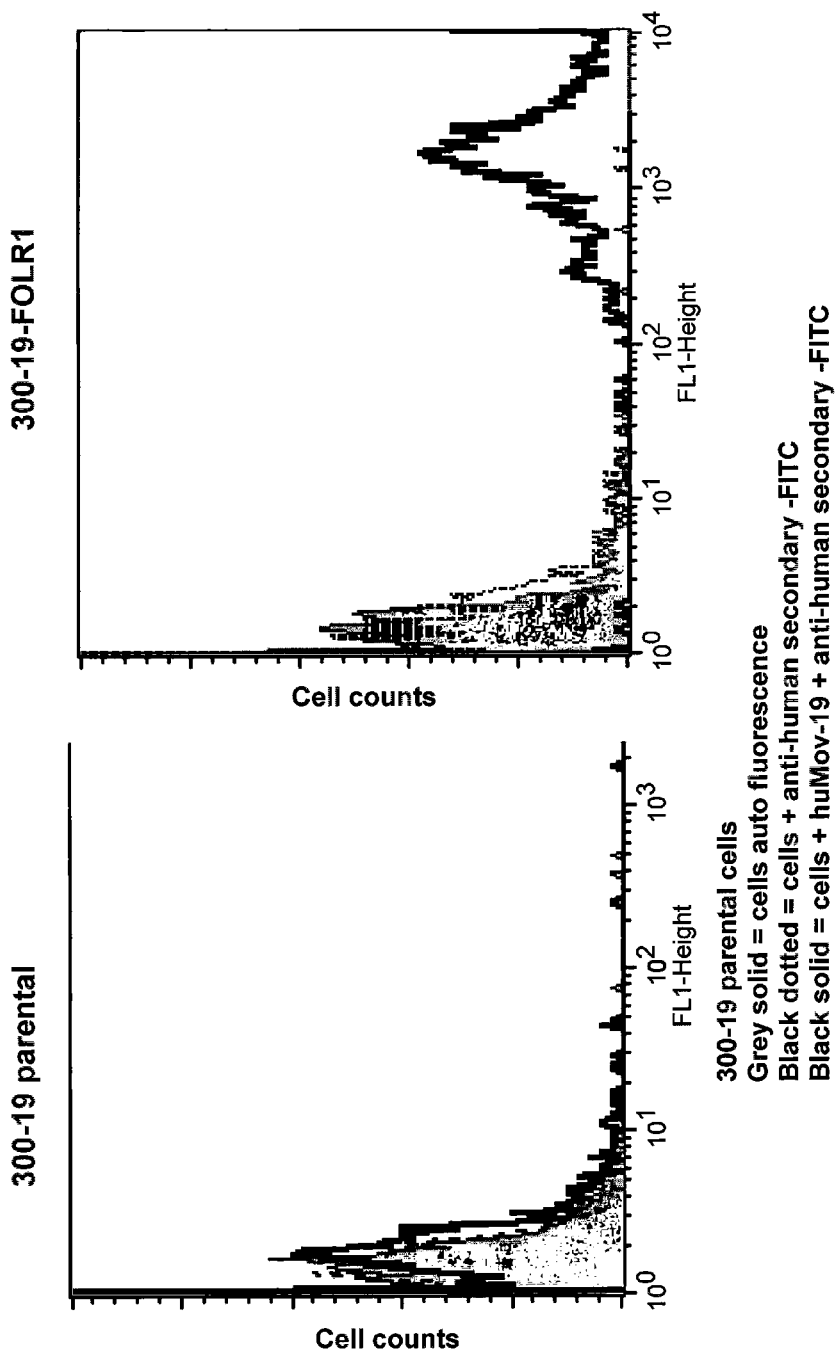

FIG. 4. Binding specificity of anti-FOLR1 antibodies, as detected by their binding to FOLR1-expressing 300-19 cells. The binding of huMov19 to 300-19-FOLR1 cells by flow cytometry. 300-19 parental cells expressing FOLR-1. The grey solid shading represents cellular auto fluorescence; the black dotted lines represent cells incubated with anti-human secondary antibody conjugated with FITC, the black solid lines represent cells incubated with the huMov-19 antibody and anti-human secondary antibody conjugated to FITC.

FIG. 5. Binding affinities and in vitro cytotoxic activity of anti-FOLR1 antibodies and immunoconjugates. Binding affinity of huMov19 and various murine and humanized FR-1 antibodies was measured on SKOV3 cells. In vitro cytotoxic activity of PEG4-Mal-DM4 conjugates of the listed antibodies was also assayed.

Figure 6:
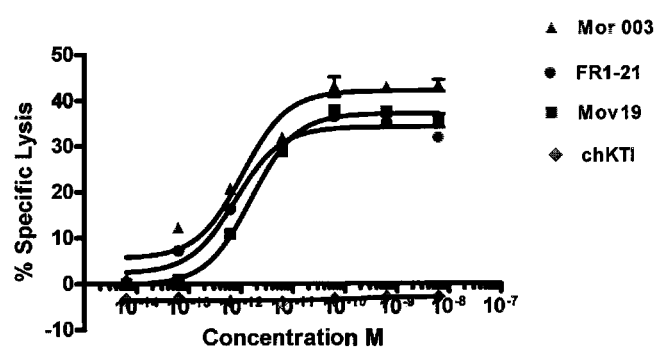

FIG. 6. Antibody-dependent cellular cytotoxicity of immunoconjugates. ADCC activity of huMov19, huFR1-21, and Mor003 was assayed against Igrov1 cells. Igrov1 were incubated at 15000 cells/well Target:NK cell ratio of 1:4.

Figure 7:
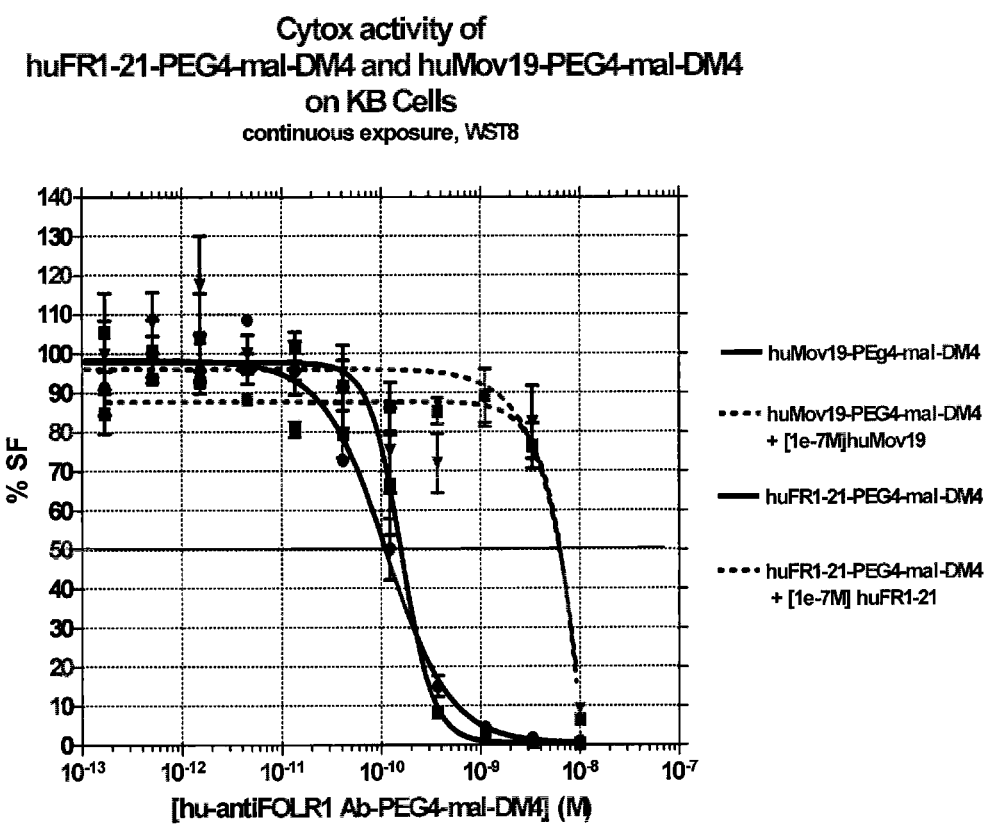

FIG. 7. Cytoxic activity of continuous exposure of huFR1-21-PEG4-mal-DM4 and huMov19-PEG4-mal-DM4 on KB cells. An excess of non-conjugated antibodies suppressed the activity of immunoconjugates when they were co-incubated in the presence of KB cells, indicating cytotoxic activity is antigen-dependent.

Figure 8:
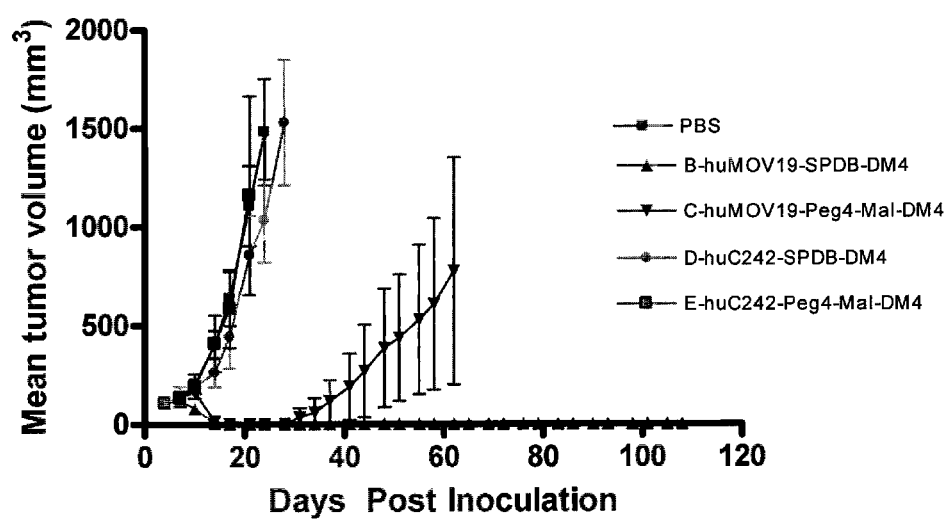

FIG. 8. In vivo efficacy of huMov19-targeted conjugates in a KB xenograft model. FOLR1-targeting cleavable conjugate huMov19-SPDB-DM4 (B) in comparison with non-FOLR1-targeting huC242-SPDB-DM4 (D), and non-cleavable conjugate huMov19-PEG4-Mal-DM4 (C) in comparison with non-targeting huC242-PEG4Mal-DM4 (E) were tested using an established xenograft model of KB cells implanted subcutaneous into SCID mice. Targeting of FOLR1 by huMov19 resulted in significant reduction in mean tumor volume.

Figure 9:
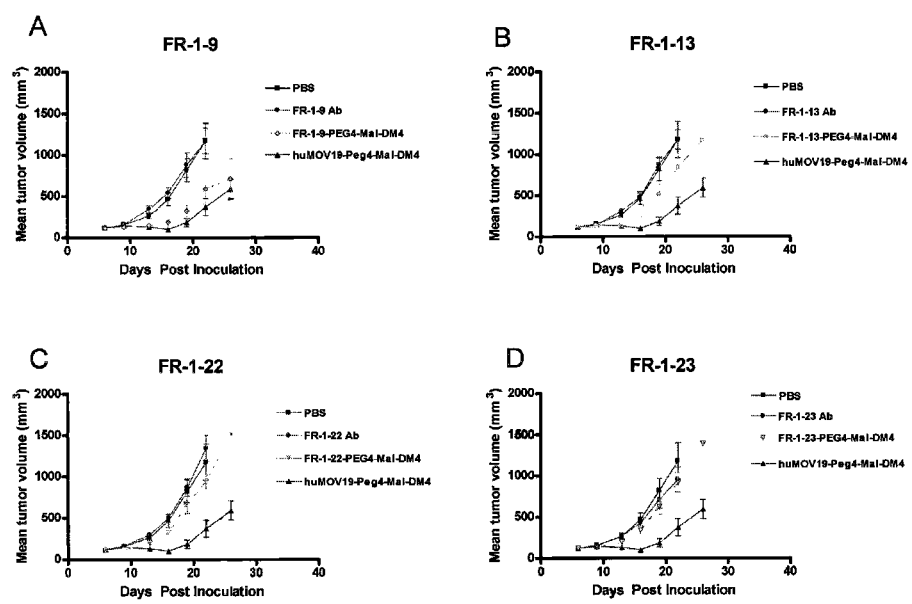

FIG. 9. In vivo efficacy of huMov19-PEG4-Mal-DM4 compared to murine FR-1 anti-FOLR1 antibodies in a KB xenograft model. FR-1 series antibodies, either unconjugated, or conjugated with PEG4-Mal-DM4 were tested for their ability to reduce mean tumor volume compared to huMov19-PEG4-Mal-DM4 in a KB xenograft tumor model. (A) FR-1-9, (B) FR-1-13, (C) FR-1-22, and (D) FR-1-23.

Figure 10:
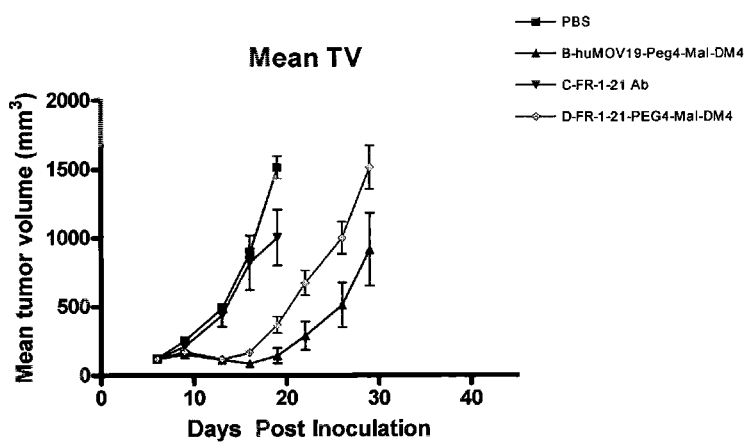

FIG. 10. In vivo efficacy of huMov19-PEG4-Mal-DM4 and huFR1-21-PEG4-Mal-DM4 in a KB xenograft model. 10 mg/kg single injections of huMov19-PEG4-Mal-DM4 and huFR1-21-PEG4-Mal-DM4 on day 6 post inoculation was performed. Both huMov19-PEG4-Mal-DM12 4 and huFR1-21-PEG4-Mal-DM4 showed a significant reduction in mean tumor volume. "Mean TV" refers to mean tumor volume.

Figure 11:
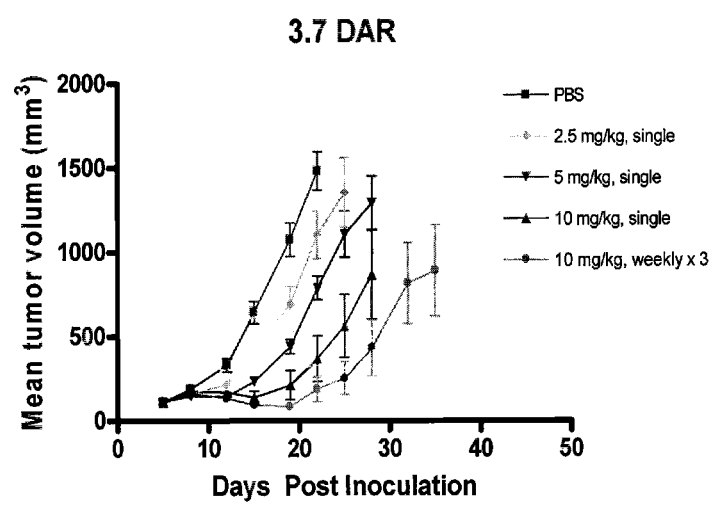

FIG. 11. HuMov19-PEG4-mal-DM4 shows dose dependent activity in the KB xenograft model. Dose dependent activity of the immunoconjugate was assayed across the range of doses tested. Weekly dosing resulted in improvement of anti-tumor activity. High drug loads only marginally improved activity in the 10 mg/kg dose groups, with reduced activity in the lower dose groups. 3.7 DAR refers to 3.7 drug molecules per antibody.

FIG. 12. In vivo efficacy of huMov19 conjugated with DM1 and DM4 with various linkers. huMov19 was conjugated to SMCC-DM1 at 3.9 drug molecules per antibody (A), sulfo-mal-DM4 at 3.7 drug molecules per antibody (B), and sulfo-mal-DM4 at 8.23 drug molecules per antibody (C) and assayed for their ability to reduce mean tumor volume at various concentrations compared to huMov19-PEG4-mal-DM4.

FIG. 13. In vivo efficacy of huMov19 conjugated with DM1 and DM4 with various linkers. huMov19 was conjugated to SPP-DM1 at 4.3 drug molecules per antibody; sulfo-SPDB-DM4 at 3.8 drug molecules per antibody, SPDB-DM4 at 3.8 drug molecules per antibody, and sulfo-SPDB-DM4 at 6.8 drug molecules per antibody and assayed for their ability to reduce mean tumor volume. Mice were treated with 5 mg/kg (A) and 2.5 mg/kg (B) of one of the conjugates listed above or with PBS only.

Figure 14:
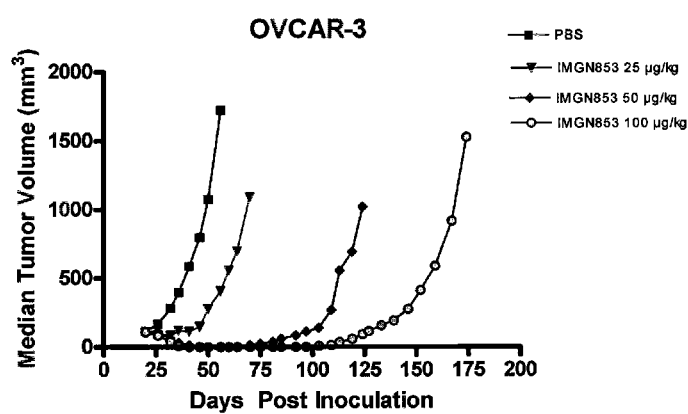

FIG. 14. In vivo efficacy of huMov19-sulfo-SPDB-DM4 in OVCAR-3 xenograft tumor model. Mice were treated with 25, 50, or 100 µg/kg of huMov19-sulfo-SPDB-DM4 or with PBS only.

Figure 15:
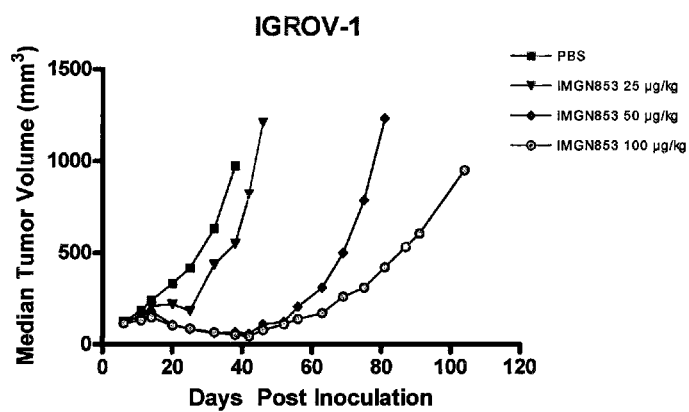

FIG. 15. In vivo efficacy of huMov19-sulfo-SPDB-DM4 in IGROV-1 xenograft tumor model. Mice were treated with 25, 50, or 100 µg/kg of huMov19-sulfo-SPDB-DM4 or with PBS only FIG. 16. In vivo efficacy of huMov19-sulfo-SPDB-DM4 in OV-90 xenograft tumor model. Mice were treated with 25, 50, or 100 µg/kg of huMov19-sulfo-SPDB-DM4 or with PBS only.

Figure 17:
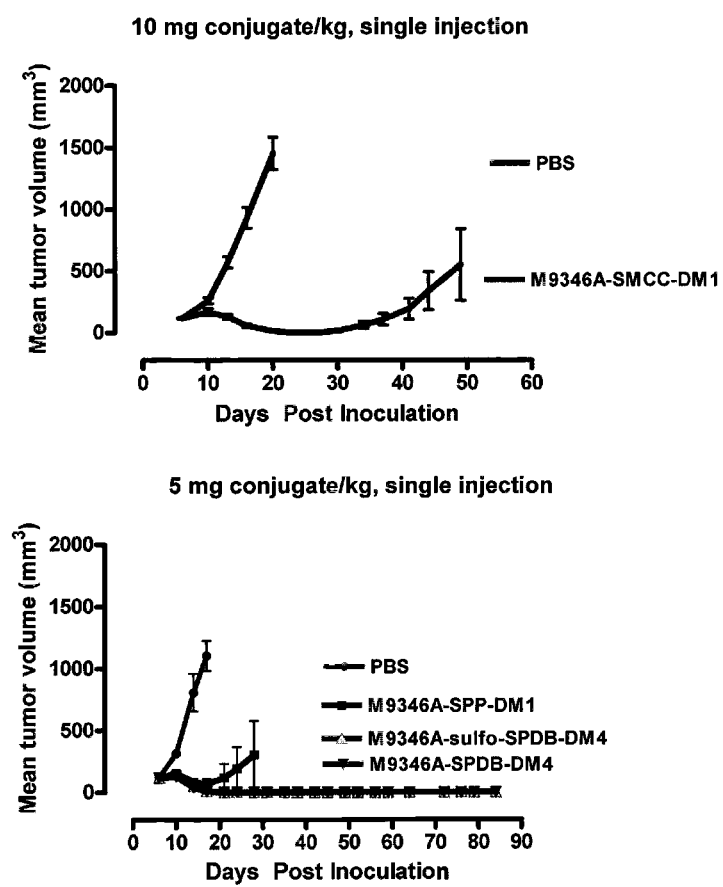

FIG. 17. Effect of cleavable and non-cleavable linkers on efficacy of immunoconjugates in KB xenograft models.

FIG. 18. Effect of cleavable linkers on efficacy of immunoconjugates in (A) KB xenograft model (B) OVCAR-3 xenograft model.

Figure 19:
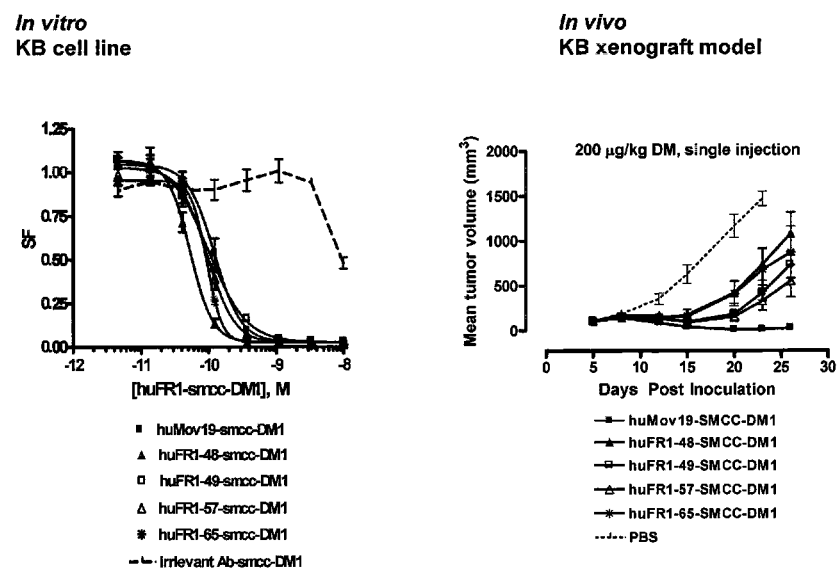

FIG. 19. In vitro and in vivo efficacy of huFR1-48, huFR1-49, huFR1-57, and huFR1-65-SMCC-DM1 in KB and xenograft tumor models. Mice were treated with 200 µg/kg single doses.

DETAILED DESCRIPTION OF THE INVENTION

The present invention provides novel agents, including, but not limited to polypeptides such as antibodies, and immunoconjugates that bind to human folate receptor 1 (FOLR1). Related polypeptides and polynucleotides, compositions comprising the FOLR1-binding agents, and methods of making the FOLR1-binding agents are also provided. Methods of using the novel FOLR1-binding agents, such as methods of inhibiting tumor growth and/or treating cancer, are further provided.

I. Definitions

To facilitate an understanding of the present invention, a number of terms and phrases are defined below.

The terms "human folate receptor 1" or "FOLR1", as used herein, refers to any native human FOLR1, unless otherwise indicated. The term "FOLR1" encompasses "full-length," unprocessed FOLR1 as well as any form of FOLR1 that results from processing within the cell. The term also encompasses naturally occurring variants of FOLR1, e.g., splice variants, allelic variants and isoforms. The FOLR1 polypeptides described herein can be isolated from a variety of sources, such as from human tissue types or from another source, or prepared by recombinant or synthetic methods. Examples of FOLR1 sequences include, but are not limited to NCBI reference numbers P15328, NP_001092242.1, AAX29268.1, AAX37119.1,NP_057937.1, and NP_057936.1.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as FOLR1. In a certain embodiment blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-FOLR1 antibody" or "an antibody that binds to FOLR1" refers to an antibody that is capable of binding FOLR1 with sufficient affinity such that the antibody is useful as a diagnostic and/or therapeutic agent in targeting FOLR1. The extent of binding of an anti-FOLR1 antibody to an unrelated, non-FOLR1 protein is less than about 10% of the binding of the antibody to FOLR1 as measured, e.g., by a radioimmunoassay (RIA). In certain embodiments, an antibody that binds to FOLR1 has a dissociation constant (Kd) of ≤1 μM, ≤100 nM, ≤10 nM, ≤1 nM, or ≤0.1 nM.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 ... 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., Kd values). The difference between said two values is less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-FOLR1 antibody or fragment thereof) and is defined by a generic formula: C-L-A, wherein C=cytotoxin, L=linker, and A=cell binding agent or anti-FOLR1 antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti FOLR1 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

"Tumor" and "neoplasm" refer to any mass of tissue that result from excessive cell growth or proliferation, either benign (noncancerous) or malignant (cancerous) including pre-cancerous lesions.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. Such formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48): 444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the FOLR1 to which the polypeptide or antibody binds. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:.412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. FOLR1-binding Agents

The present invention provides agents that specifically bind human FOLR1. These agents are referred to herein as "FOLR1-binding agents." The full-length amino acid (aa) and nucleotide (nt) sequences for FOLR1 are known in the art and also provided herein as represented by SEQ ID NOs:25 and 26, respectively.

In certain embodiments, the FOLR1 binding agents are antibodies, immunoconjugates or polypeptides. In some embodiments, the FOLR1 binding agents are humanized antibodies. In certain embodiments, the FOLR-1 binding agents are humanized versions of the murine Mov19 antibody (variable heavy and light chain shown as SEQ ID NOs: 17 and 18 respectively).

In certain embodiments, the FOLR1-binding agents have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In certain embodiments, immunoconjugates or other agents that specifically bind human FOLR1 trigger cell death via a cytotoxic agent. For example, in certain embodiments, an antibody to a human FOLR1 antibody is conjugated to a maytansinoid that is activated in tumor cells expressing the FOLR1 by protein internalization. In certain alternative embodiments, the agent or antibody is not conjugated.

In certain embodiments, the FOLR1-binding agents are capable of inhibiting tumor growth. In certain embodiments, the FOLR1-binding agents are capable of inhibiting tumor growth in vivo (e.g., in a xenograft mouse model and/or in a human having cancer). In certain embodiments, the FOLR1-binding agents are capable of inhibiting tumor growth in a human.

Thus, the invention provides a humanized antibody or antigen binding fragment thereof that specifically binds a human folate receptor 1, wherein the antibody comprises: (a) a heavy chain CDR1 comprising GYFMN (SEQ ID NO:1); a heavy chain CDR2 comprising RIHPYDGDTFYNQXaa$_1$FXaa$_2$Xaa$_3$ (SEQ ID NO:56); and a heavy chain CDR3 comprising YDGSRAMDY (SEQ ID NO:3); and (b) a light chain CDR1 comprising KASQSVSFAGTSLMH (SEQ ID NO:7); a light chain CDR2 comprising RASNLEA (SEQ ID NO:8); and a light chain CDR3 comprising QQSREYPYT (SEQ ID NO:9); wherein Xaa$_1$ is selected from K, Q, H, and R; Xaa$_2$ is selected from Q, H, N, and R; and Xaa$_3$ is selected from G, E, T, S, A, and V. In certain embodiments, the antibody is the huMov19 antibody, which is the above-described antibody comprising the heavy chain CDR2 RIHPYDGDTFYNQKFQG (SEQ ID NO:2).

In certain embodiments, the invention provides humanized antibodies or antigen binding fragments that specifically bind to FOLR1 that comprise the CDRs of huMov19 with up to four (i.e. 0, 1, 2, 3, or 4) conservative amino acid substitutions per CDR. Thus, in certain embodiments the invention provides humanized antibodies or antigen binding fragments that specifically binds a human folate receptor 1, wherein the antibody comprises: (a) a heavy chain CDR1 comprising GYFMN (SEQ ID NO:1), or a variant thereof comprising 1, 2, 3, or 4 conservative amino acid substitutions; a heavy chain CDR2 comprising RIHPYDGDTFYNQKFQG (SEQ ID NO:2), or a variant thereof comprising 1, 2, 3, or 4 amino conservative acid substitutions; and a heavy chain CDR3 comprising YDGSRAMDY (SEQ ID NO:3), or a variant thereof comprising 1, 2, 3, or 4 conservative amino acid substitutions; and/or (b) a light chain CDR1 comprising KASQSVSFAGTSLMH (SEQ ID NO:7), or a variant thereof comprising 1, 2, 3, or 4 conservative amino acid substitutions; a light chain CDR2 comprising RASNLEA (SEQ ID NO:8), or a variant thereof comprising 1, 2, 3, or 4 conservative amino acid substitutions; and a light chain CDR3 comprising QQSREYPYT (SEQ ID NO:9), or a variant thereof comprising 1, 2, 3, or 4 conservative amino acid substitutions.

The invention also provides a humanized antibody (huFR1-21) or antigen binding fragment thereof that specifically binds a human folate receptor 1, wherein the antibody comprises: (a) a heavy chain CDR1 comprising SSYGMS (SEQ ID NO:30); a heavy chain CDR2 comprising TISSGGSYTY (SEQ ID NO:31); and a heavy chain CDR3 comprising DGEGGLYAMDY (SEQ ID NO:32); and/or (b) a light chain CDR1 comprising KASDHINNWLA (SEQ ID NO:27); a light chain CDR2 comprising GATSLET (SEQ ID NO:28); and a light chain CDR3 comprising QQYWSTPFT (SEQ ID NO:29).

In certain embodiments, the invention provides humanized antibodies or antigen binding fragments that specifically bind to FOLR1 that comprise the CDRs of huFR1-21 with up to four (i.e. 0, 1, 2, 3, or 4) conservative amino acid substitutions per CDR. Thus, in certain embodiments the invention provides humanized antibodies or antigen binding fragments that specifically binds a human folate receptor 1, wherein the antibody comprises: (a) a heavy chain CDR1 comprising SSYGMS (SEQ ID NO:30) or a variant thereof comprising 1, 2, 3, or 4 conservative amino acid substitutions; and/or a heavy chain CDR2 comprising TISSGGSYTY (SEQ ID NO:31) or a variant thereof comprising 1, 2, 3, or 4 conservative amino acid substitutions; and/or and a heavy chain CDR3 comprising DGEGGLYAMDY (SEQ ID NO:32) or a variant thereof comprising 1, 2, 3, or 4 conservative amino acid substitutions; and/or (b) a light chain CDR1 comprising KASDHINNWLA (SEQ ID NO:27) or a variant thereof comprising 1, 2, 3, or 4 conservative amino acid substitutions; and/or a light chain CDR2 comprising GATSLET (SEQ ID NO:28) or a variant thereof comprising 1, 2, 3, or 4 conservative amino acid substitutions; and/or a light chain CDR3 comprising QQYWSTPFT (SEQ ID NO:29) or a variant thereof comprising 1, 2, 3, or 4 conservative amino acid substitutions.

In certain embodiments, the invention provides humanized antibodies or antigen binding fragments that specifically bind to FOLR1 that comprise the CDRs of huFR1-48 with up to four (i.e. 0, 1, 2, 3, or 4) conservative amino acid substitutions per CDR. Thus, in certain embodiments the invention provides humanized antibodies or antigen binding fragments that specifically binds a human folate receptor 1, wherein the antibody comprises: (a) a heavy chain CDR1 comprising TNYWMQ (SEQ ID NO:60) or a variant thereof comprising 1, 2, 3, or 4 conservative amino acid substitutions; and/or a heavy chain CDR2 comprising IYPGNGDSR (SEQ ID NO:61) or a variant thereof comprising 1, 2, 3, or 4 conservative amino acid substitutions; and/or and a heavy chain CDR3 comprising RDGNYAAY (SEQ ID NO:62) or a variant thereof comprising 1, 2, 3, or 4 conservative amino acid substitutions; and/or (b) a light chain CDR1 comprising RASENIYSNLA (SEQ ID NO:57) or a variant thereof comprising 1, 2, 3, or 4 conservative amino acid substitutions; and/or a light chain CDR2 comprising AATNLAD (SEQ ID NO:58) or a variant thereof comprising 1, 2, 3, or 4 conservative amino acid substitutions; and/or a light chain CDR3 comprising QHFWASPYT (SEQ ID NO:59) or a variant thereof comprising 1, 2, 3, or 4 conservative amino acid substitutions.

In certain embodiments, the invention provides humanized antibodies or antigen binding fragments that specifically bind to FOLR1 that comprise the CDRs of huFR1-49 with up to four (i.e. 0, 1, 2, 3, or 4) conservative amino acid substitutions per CDR. Thus, in certain embodiments the invention provides humanized antibodies or antigen binding fragments that specifically binds a human folate receptor 1, wherein the antibody comprises: (a) a heavy chain CDR1 comprising TNYWMY (SEQ ID NO:66) or a variant thereof comprising 1, 2, 3, or 4 conservative amino acid substitutions; and/or a heavy chain CDR2 comprising AIYPGNSDTT (SEQ ID NO:67) or a variant thereof comprising 1, 2, 3, or 4 conservative amino acid substitutions; and/or and a heavy chain CDR3 comprising RHDYGAMDY (SEQ ID NO:68) or a variant thereof comprising 1, 2, 3, or 4 conservative amino acid substitutions; and/or (b) a light chain CDR1 comprising RASENIYTNLA (SEQ ID NO:63) or a variant thereof comprising 1, 2, 3, or 4 conservative amino acid substitutions; and/or a light chain CDR2 comprising TASNLAD (SEQ ID NO:64) or a variant thereof comprising 1, 2, 3, or 4 conservative amino acid substitutions; and/or a light chain CDR3 comprising QHFWVSPYT (SEQ ID NO:65) or a variant thereof comprising 1, 2, 3, or 4 conservative amino acid substitutions.

In certain embodiments, the invention provides humanized antibodies or antigen binding fragments that specifically bind to FOLR1 that comprise the CDRs of huFR1-57 with up to four (i.e. 0, 1, 2, 3, or 4) conservative amino acid substitutions per CDR. Thus, in certain embodiments the invention provides humanized antibodies or antigen binding fragments that specifically binds a human folate receptor 1, wherein the antibody comprises: (a) a heavy chain CDR1 comprising SSFGMH (SEQ ID NO:72) or a variant thereof comprising 1, 2, 3, or 4 conservative amino acid substitutions; and/or a heavy chain CDR2 comprising YISSGSSTIS (SEQ ID NO:73) or a variant thereof comprising 1, 2, 3, or 4 conservative amino acid substitutions; and/or and a heavy chain CDR3 comprising EAYGSSMEY (SEQ ID NO:74) or a variant thereof comprising 1, 2, 3, or 4 conservative amino acid substitutions; and/or (b) a light chain CDR1 comprising RASQNINNNLH (SEQ ID NO:69) or a variant thereof comprising 1, 2, 3, or 4 conservative amino acid substitutions; and/or a light chain CDR2 comprising YVSQSVS (SEQ ID NO:70) or a variant thereof comprising 1, 2, 3, or 4 conservative amino acid substitutions; and/or a light chain CDR3 comprising QQSNSWPHYT (SEQ ID NO:71) or a variant thereof comprising 1, 2, 3, or 4 conservative amino acid substitutions.

In certain embodiments, the invention provides humanized antibodies or antigen binding fragments that specifically bind to FOLR1 that comprise the CDRs of huFR1-65 with up to four (i.e. 0, 1, 2, 3, or 4) conservative amino acid substitutions per CDR. Thus, in certain embodiments the invention provides humanized antibodies or antigen binding fragments that specifically binds a human folate receptor 1, wherein the antibody comprises: (a) a heavy chain CDR1 comprising TSYTMH (SEQ ID NO:78) or a variant thereof comprising 1, 2, 3, or 4 conservative amino acid substitutions; and/or a heavy chain CDR2 comprising YINPISGYTN (SEQ ID NO:79) or a variant thereof comprising 1, 2, 3, or 4 conservative amino acid substitutions; and/or and a heavy chain CDR3 comprising GGAYGRKPMDY (SEQ ID NO:80) or a variant thereof comprising 1, 2, 3, or 4 conservative amino acid substitutions; and/or (b) a light chain CDR1 comprising KASQNVGPNVA (SEQ ID NO:75) or a variant thereof comprising 1, 2, 3, or 4 conservative amino acid substitutions; and/or a light chain CDR2 comprising SASYRYS (SEQ ID NO:76) or a variant thereof comprising 1, 2, 3, or 4 conservative amino acid substitutions; and/or a light chain CDR3 comprising QQYNSYPYT (SEQ ID NO:77) or a variant thereof comprising 1, 2, 3, or 4 conservative amino acid substitutions.

Polypeptides comprising one of the individual light chains or heavy chains described herein, as well as polypeptides (e.g., antibodies) comprising both a light chain and a heavy chain are also provided. The polypeptides of SEQ ID NOs: 4 and 6 comprise the variable domain of the heavy chain of huMov19, and the heavy chain of huMov19, respectively. The polypeptides of SEQ ID NOs:10-13 comprise the variable domain light chain version 1.00, the variable domain light chain version 1.60, the light chain version 1.00, and the light chain version 1.60 of huMov19, respectively. The polypeptides of SEQ ID NOs: 42 and 46 comprise the variable domain of the heavy chain of huFR1-21, and the heavy chain of huFR1-21, respectively. The polypeptides of SEQ ID NOs:41 and 45 comprise the variable domain light chain and light chain of huFR1-21, respectively. The polypeptides of SEQ ID NOs: 97 and 113 comprise the variable domain of the heavy chain of huFR1-48, and the heavy chain of huFR1-48, respectively. The polypeptides of SEQ ID NOs:96 and 112 comprise the variable domain light chain and light chain of huFR1-48, respectively. The polypeptides of SEQ ID NOs: 99 and 115 comprise the variable domain of the heavy chain of huFR1-49, and the heavy chain of huFR1-49, respectively. The polypeptides of SEQ ID NOs:98 and 114 comprise the variable domain light chain and light chain of huFR1-49, respectively. The polypeptides of SEQ ID NOs: 101 and 117 comprise the variable domain of the heavy chain of huFR1-57, and the heavy chain of huFR1-57, respectively. The polypeptides of SEQ ID NOs:100 and 116 comprise the variable domain light chain and light chain of huFR1-57, respectively. The polypeptides of SEQ ID NOs:103 and 119 comprise the variable domain of the heavy chain of huFR1-65, and the heavy chain of huFR1-65, respectively. The polypeptides of SEQ ID NOs:102 and 118 comprise the variable domain light chain and light chain of huFR1-65, respectively.

Also provided are polypeptides that comprise: (a) a polypeptide having at least about 90% sequence identity to SEQ ID NO:4 or 6; and/or (b) a polypeptide having at least about 90% sequence identity to SEQ ID NOs:10-13. Also provided are polypeptides that comprise: (a) a polypeptide having about 90% sequence identity to SEQ ID NO: 42 or 46; and/or (b) a polypeptide having at least about 90% sequence identity to SEQ ID NOs: 41 and 45. Also provided are polypeptides that comprise: (a) a polypeptide having at least about 90% sequence identity to SEQ ID NO:97 or 113; and/or (b) a polypeptide having at least about 90% sequence identity to SEQ ID NOs:96 or 112. Also provided are polypeptides that comprise: (a) a polypeptide having at least about 90% sequence identity to SEQ ID NO:99 or 115; and/or (b) a polypeptide having at least about 90% sequence identity to SEQ ID NOs:98 or 114. Also provided are polypeptides that comprise: (a) a polypeptide having at least about 90% sequence identity to SEQ ID NO:101 or 117; and/or (b) a polypeptide having at least about 90% sequence identity to SEQ ID NOs:100 or 116. Also provided are polypeptides that comprise: (a) a polypeptide having at least about 90% sequence identity to SEQ ID NO:103 or 119; and/or (b) a polypeptide having at least about 90% sequence identity to SEQ ID NOs:102 or 118. In certain embodiments, the polypeptide comprises a polypeptide having at least about 95%, at least about 96%, at least about 97%, at least about 98%, or at least about 99% sequence identity to SEQ ID NOs:4, 6, 10-13, 41, 42, 45 or 46. Thus, in certain embodiments, the polypeptide comprises (a) a polypeptide having at least about 95% sequence identity to SEQ ID NO:4 or 6, and/or (b) a polypeptide having at least about 95% sequence identity to SEQ ID NOs:10-13. In certain embodiments, the polypeptide comprises (a) a polypeptide having at least about 95% sequence identity to SEQ ID NO:42 or 46, and/or (b) a polypeptide having at least about 95% sequence identity to SEQ ID NOs:41 or 45. Also provided are polypeptides that comprise: (a) a polypeptide having at least about 95% sequence identity to SEQ ID NO:97 or 113; and/or (b) a polypeptide having at least about 95% sequence identity to SEQ ID NOs:96 or 112. Also provided are polypeptides that comprise: (a) a polypeptide having at least about 95% sequence identity to SEQ ID NO:99 or 115; and/or (b) a polypeptide having at least about 95% sequence identity to SEQ ID NOs:98 or 114. Also provided are polypeptides that comprise: (a) a polypeptide having at least about 95% sequence identity to SEQ ID NO:101 or 117; and/or (b) a polypeptide having at least about 95% sequence identity to SEQ ID NOs:100 or 116. Also provided are polypeptides that comprise: (a) a polypeptide having at least about 95% sequence identity to SEQ ID NO:103 or 119; and/or (b) a polypeptide having at least about 95% sequence identity to SEQ ID NOs:102 or 118. In certain embodiments, the polypeptide comprises (a) a polypeptide having the amino acid sequence of SEQ ID NO: 4; and/or (b) a polypeptide having the amino acid sequence of SEQ ID NO:10 or SEQ ID NO:11. In certain embodiments, the polypeptide comprises (a) a polypeptide having the amino acid sequence of SEQ ID NO:45; and/or (b) a polypeptide having the amino acid sequence of SEQ ID NO:46. In certain embodiments, the polypeptide comprises (a) a polypeptide having the amino acid sequence of SEQ ID NO: 6; and/or (b) a polypeptide having the amino acid sequence of SEQ ID NO:12 or SEQ ID NO:13. In certain embodiments, the polypeptide is an antibody and/or the polypeptide specifically binds human folate receptor 1. In certain embodiments, the polypeptide is a humanized antibody that specifically binds human folate receptor 1. For example, the invention provides an antibody or humanized antibody that specifically binds a human FOLR1 that comprises (a) a polypeptide having the amino acid sequence of SEQ ID NO: 4; and (b) a polypeptide having the amino acid sequence of SEQ ID NO:10 or SEQ ID NO:11. In certain embodiments the polypeptide comprising SEQ ID NO:4 is a heavy chain variable region. In certain embodiments, the polypeptide comprising SEQ ID NO:10 or 11 is a light chain variable region. The invention also provides an antibody or humanized antibody that specifically binds a human FOLR1 that comprises (a) a polypeptide having the amino acid sequence of SEQ ID NO: 6; and (b) a polypeptide having the amino acid sequence of SEQ ID NO:12 or SEQ ID NO:13. The invention also provides and antibody or humanized antibody that specifically binds a human FOLR1 that comprises (a) a polypeptide having the amino acid sequence of SEQ ID NO:45; and (b) a polypeptide having the amino acid sequence of SEQ ID NO:46. The invention also provides and antibody or humanized antibody that specifically binds a human FOLR1 that comprises (a) a polypeptide having the amino acid sequence of SEQ ID NO:112; and (b) a polypeptide having the amino acid sequence of SEQ ID NO:113. The invention also provides and antibody or humanized antibody that specifically binds a human FOLR1 that comprises (a) a polypeptide having the amino acid sequence of SEQ ID NO:114; and (b) a polypeptide having the amino acid sequence of SEQ ID NO:115. The invention also provides and antibody or humanized antibody that specifically binds a human FOLR1 that comprises (a) a polypeptide having the amino acid sequence of SEQ ID NO:116; and (b) a polypeptide having the amino acid sequence of SEQ ID NO:117. The invention also provides and antibody or humanized antibody that specifically binds a human FOLR1 that comprises (a) a polypeptide having the amino acid sequence of SEQ ID NO:118; and (b) a polypeptide having the amino acid sequence of SEQ ID NO:119. In certain embodiments, the polypeptide having a certain percentage of sequence identity to SEQ ID NOs: 4, 6, 10-13, 41, 42, 45, 46, 96-103 and 112-119 differs from SEQ ID NO: 4, 6, 10-13, 41, 42, 45, 46, 96-103 and 112-119 by conservative amino acid substitutions only.

In certain embodiments, the FOLR1-binding agent comprises, consists essentially of, or consists of an anti-FOLR1 antibody selected from the group consisting of huMov19, FR-1-21, FR1-48, FR1-49, FR1-57, and FR1-65 antibodies.

In certain embodiments, the huMov19 antibody is encoded by the plasmids deposited with the American Type Culture Collection (ATCC) on Apr. 7, 2010 and having ATCC deposit nos. PTA-10772 and PTA-10773 or 10774.

In certain embodiments, the FR-1-21 antibody is encoded by the plasmids deposited with the ATCC on Apr. 7, 2010, and assigned deposit designation numbers PTA-10775 and 10776.

In certain embodiments, the humanized antibodies bind FOLR1 with substantially the same affinity as the antibody chimeric Mov19. The affinity or avidity of an antibody for an antigen can be determined experimentally using any suitable method well known in the art, e.g. flow cytometry, enzyme-linked immunoabsorbent assay (ELISA), or radioimmunoassay (RIA), or kinetics (e.g., BIACORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., KD or Kd, $K_{on}$, $K_{off}$) are made with standardized solutions of antibody and antigen, and a standardized buffer, as known in the art and such as the buffer described herein.

In one aspect, binding assays can be performed using flow cytometry on cells expressing the FOLR1 antigen on the surface. For example, FOLR1-positive cells such as SKOV3 were incubated with varying concentrations of anti-FOLR1 antibodies using 1×105 cells per sample in 100 µL FACS buffer (RPMI-1640 medium supplemented with 2% normal goat serum). Then, the cells were pelleted, washed, and incubated for 1 h with 100 µL of FITC-conjugated goat-anti-mouse or goat-anti-human IgG-antibody (such as is obtainable from, for example Jackson Laboratory, 6 µg/mL in FACS buffer). The cells were pelleted again, washed with FACS buffer and resuspended in 200 µL of PBS containing 1% formaldehyde. Samples were acquired, for example, using a FACSCalibur flow cytometer with the HTS multiwell sampler and analyzed using CellQuest Pro (all from BD Biosciences, San Diego, US). For each sample the mean fluorescence intensity for FL1 (MFI) was exported and plotted against the antibody concentration in a semi-log plot to generate a binding curve. A sigmoidal dose-response curve is fitted for binding curves and EC50 values are calculated using programs such as GraphPad Prism v4 with default parameters (GraphPad software, San Diego, Calif.). EC50 values can be used as a measure for the apparent dissociation constant "Kd" or "KD" for each antibody.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human FOLR1 is a humanized antibody. In certain embodiments, such antibodies are used therapeutically to reduce antigenicity and HAMA (human anti-mouse antibody) responses when administered to a human subject.

Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing FOLR1 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen FOLR1 and other favorable biological properties. To achieve this goal, humanized (or human) or engineered anti-FOLR1 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as FOLR1. In this way, framework (FR) residues can be selected and combined from the consensus and import sequences so that the desired antibody characteristic, such as increased affinity for the target antigen(s), is achieved.

Humanization, resurfacing or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/: US98/16280; US96/18978; US91/09630; US91/05939; US94/01234; GB89/01334; GB91/01134; GB92/01755; WO90/14443; WO90/14424; WO90/14430; EP 229246; U.S. Pat. Nos. 7,557,189; 7,538,195; and 7,342,110, each of which is entirely incorporated herein by reference, including the references cited therein.

In certain alternative embodiments, the antibody to FOLR1 is a human antibody. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a human folate receptor 1. Bispecific antibodies are antibodies that are capable of specifically recognizing and binding at least two different epitopes. The different epitopes can either be within the same molecule (e.g. the same human folate receptor 1) or on different molecules such that both, for example, the antibodies can specifically recognize and bind a human folate receptor 1 as well as, for example, 1) an effector molecule on a leukocyte such as a T-cell receptor (e.g. CD3) or Fc receptor (e.g. CD64, CD32, or CD16) or 2) a cytotoxic agent as described in detail below.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148: 1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to FOLR1 are multispecific.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to human folate receptor 1 (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for a folate 1 receptor, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human FOLR1. In this regard, the variable region can comprise or be derived from any type of mammal that can be induced to mount a humoral response and generate immunoglobulins against the desired tumor associated antigen. As such, the variable region of the modified antibodies can be, for example, of human, marine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the FOLR1-binding antibodies provide for altered effector functions that, in turn, affect the biological profile of the administered antibody. For example, the deletion or inactivation (through point mutations or other means) of a constant region domain can reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

In certain embodiments, a FOLR1-binding agent that is an antibody does not have one or more effector functions. For instance, in some embodiments, the antibody has no antibody-dependent cellular cytotoxicity (ADCC) activity and/or no complement-dependent cytotoxicity (CDC) activity. In certain embodiments, the antibody does not bind to an Fc receptor and/or complement factors. In certain embodiments, the antibody has no effector function.

It will be noted that in certain embodiments, the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human FOLR1. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a human folate receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human FOLR1. Recombinant expression vectors are replicable DNA constructs which have synthetic or cDNA-derived DNA fragments encoding a polypeptide chain of an anti-FOLR1 antibody, or fragment thereof, operatively linked to suitable transcriptional or translational regulatory elements derived from mammalian, microbial, viral or insect genes. A transcriptional unit generally comprises an assembly of of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a FOLR1-binding polypeptide or antibody (or a FOLR1 protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a FOLR1-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

In certain embodiments, the FOLR1-binding agent is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety. In certain embodiments, phage display technology has been used to identify/produce the FOLR1-binding polypeptide. In certain embodiments, the polypeptide comprises a protein scaffold of a type selected from the group consisting of protein A, a lipocalin, a fribronectin domain, an ankyrin consensus repeat domain, and thioredoxin.

In some embodiments, the agent is a non-protein molecule. In certain embodiments, the agent is a small molecule. Combinatorial chemistry libraries and techniques useful in the identification of non-protein FOLR1-binding agents are known to those skilled in the art. See, e.g., Kennedy et al., J. Comb. Chem, 10:345-354 (2008), Dolle et al, J. Comb. Chem., 9:855-902 (2007), and Bhattacharyya, Curr. Med. Chem., 8:1383-404 (2001), each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. Nos. 5,270,163, 5,683,867, 5,763,595, 6,344,321, 7,368, 236, 5,582,981, 5,756,291, 5,840,867, 7,312,325, 7,329,742, International Patent Publication No. WO 02/077262, International Patent Publication No. WO 03/070984, U.S. Patent Application Publication No. 2005/0239134, U.S. Patent Application Publication No. 2005/0124565, and U.S. Patent Application Publication No. 2008/0227735, each of which is incorporated by reference herein in its entirety.

III. Immunoconjugates

The present invention is also directed to conjugates (also referred to herein as immunoconjugates), comprising the anti-FOLR1 antibodies, antibody fragments, functional equivalents, improved antibodies and their aspects as disclosed herein, linked or conjugated to a cytotoxin (drug) or prodrug. Thus, in a certain embodiment, the invention provides an immunoconjugate comprising a humanized antibody or antigen binding fragment thereof that specifically binds a human folate receptor 1, wherein the antibody comprises: (a) a heavy chain CDR1 comprising GYFMN (SEQ ID NO:1); a heavy chain CDR2 comprising RIHPYDGDTFYNQXaa$_1$FXaa$_2$Xaa$_3$ (SEQ ID NO:56); and a heavy chain CDR3 comprising YDGSRAMDY (SEQ ID NO:3); and (b) a light chain CDR1 comprising KASQSVS-FAGTSLMH (SEQ ID NO:7); a light chain CDR2 comprising RASNLEA (SEQ ID NO:8); and a light chain CDR3 comprising QQSREYPYT (SEQ ID NO:9); wherein Xaa$_1$ is selected from K, Q, H, and R; Xaa$_2$ is selected from Q, H, N, and R; and Xaa$_3$ is selected from G, E, T, S, A, and V. In certain embodiments, the antibody is the huMov19 antibody, which is the above-described antibody comprising the heavy chain CDR2 RIHPYDGDTFYNQKFQG (SEQ ID NO:2). In other embodiments, the antibody is FR1-21 and comprises (a) a heavy chain CDR1 comprising SSYGMS (SEQ ID NO:30); a heavy chain CDR2 comprising TISSGGSYTY (SEQ ID NO:31); and/or a heavy chain CDR3 comprising DGEG-GLYAMDY (SEQ ID NO:32); and (b) a light chain CDR1 comprising KASDHINNWLA (SEQ ID NO:27); a light chain CDR2 comprising GATSLET (SEQ ID NO:28); and a light chain CDR3 comprising QQYWSTPFT (SEQ ID NO:29). In other embodiments, the antibody is FR1-48 and comprises: (a) a heavy chain CDR1 comprising TNYWMQ (SEQ ID NO:60); a heavy chain CDR2 comprising AIYPGNGDSR (SEQ ID NO:61); and/or a heavy chain CDR3 comprising RDGNYAAY (SEQ ID NO:62); and/or (b) a light chain CDR1 comprising RASENIYSNLA (SEQ ID NO:57); a light chain CDR2 comprising AATNLAD (SEQ ID NO:58); and a light chain CDR3 comprising QHFWASPYT (SEQ ID NO:59). In other embodiments, the antibody is FR1-49 and comprises: (a) a heavy chain CDR1 comprising TNYWMY (SEQ ID NO:66); a heavy chain CDR2 comprising AIYPGNSDTT (SEQ ID NO:67); and/or a heavy chain CDR3 comprising RHDYGAMDY (SEQ ID NO:68); and/or (b) a light chain CDR1 comprising RASENIYTNLA (SEQ ID NO:63); a light chain CDR2 comprising TASNLAD (SEQ ID NO:64); and a light chain CDR3 comprising QHF-WVSPYT (SEQ ID NO:65). In other embodiments, the antibody is FR1-57 and comprises: (a) a heavy chain CDR1 comprising SSFGMH (SEQ ID NO:72); a heavy chain CDR2 comprising YISSGSSTIS (SEQ ID NO:73); and/or a heavy chain CDR3 comprising EAYGSSMEY (SEQ ID NO:74); and/or (b) a light chain CDR1 comprising RASQNINNNLH (SEQ ID NO:69); a light chain CDR2 comprising YVSQSVS (SEQ ID NO:70); and a light chain CDR3 comprising QQSN-SWPHYT (SEQ ID NO:71). In yet another embodiment, the antibody is FR1-65 and comprises: (a) a heavy chain CDRI comprising TSYTMH (SEQ ID NO:78); a heavy chain CDR2 comprising YINPISGYTN (SEQ ID NO:79); and/or a heavy chain CDR3 comprising GGAYGRKPMDY (SEQ ID NO:80); and/or (b) a light chain CDR1 comprising KASQN-VGPNVA (SEQ ID NO:75); a light chain CDR2 comprising SASYRYS (SEQ ID NO:76); and a light chain CDR3 comprising QQYNSYPYT (SEQ ID NO:77).

Suitable drugs or prodrugs are known in the art. In certain embodiments, drugs or prodrugs are cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs, benzodiazepines, taxoids, CC-1065 and CC-1065 analogs, duocarmycins and duocarmycin analogs, enediynes, such as calicheamicins, dolastatin and dolastatin analogs including auristatins, tomaymycin derivaties, leptomycin derivaties, methotrexate, cisplatin, carboplatin, daunorubicin, doxorubicin, vincristine, vinblastine, melphalan, mitomycin C, chlorambucil and morpholino doxorubicin. In certain embodiments, the cytotoxic agents are maytansinoids and maytansinoids analogs.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-FOLR1 antibody or fragment thereof through a disulfide bond. The linker molecule or crosslinking agent comprises a reactive chemical group that can react with the anti-FOLR1 antibody or fragment thereof. In certain embodiments, reactive chemical groups for reaction with the cell-binding agent are N-succinimidyl esters and N-sulfosuccinimidyl esters. Additionally the linker molecule comprises a reactive chemical group, in certain embodiments a dithiopyridyl group that can react with the drug to form a disulfide bond. In certain embodiments, linker molecules include, for example, N-succinimidyl 3-(2-pyridyldithio)propionate (SPDP) (see, e.g., Carlsson et al., *Biochem. J.,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio)pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration. In certain embodiments, the anti-FOLR1 antibody is linked to the cytoxin via a SPDB or sulfo-SPDB linker. In a certain embodiment, the huMov19 antibody is linked to a cytotoxin via a SPDB or sulfo-SPDB linker.

In another aspect of the present invention, the anti-FOLR1 antibody is linked to cytotoxic drugs via disulfide bonds and a polyethylene glycol spacer in enhancing the potency, solubility or the efficacy of the immunoconjugate. Such cleavable hydrophilic linkers are described in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ((CH$_2$CH$_2$O)$_{n=1-14}$) with a narrow range of drug load of 2-8 are described that show relatively high potent biological activity toward cancer cells and have the desired biochemical properties of high conjugation yield and high monomer ratio with minimal protein aggregation.

Specifically contemplated in this aspect is an anti-FOLR1 antibody drug conjugate of formula (I) or a conjugate of formula (I'):

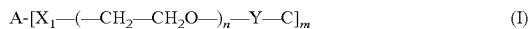
$$A\text{-}[X_1\text{—}(\text{—}CH_2\text{—}CH_2O\text{—})_n\text{—}Y\text{—}C]_m \quad (I)$$

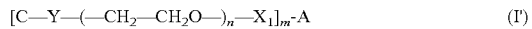
$$[C\text{—}Y\text{—}(\text{—}CH_2\text{—}CH_2O\text{—})_n\text{—}X_1]_m\text{-}A \quad (I')$$

wherein:
A represents an anti-FOLR1 antibody or fragment;
C represents a cytotoxin or drug;
X represents an aliphatic, an aromatic or a heterocyclic unit attached to the cell-binding agent via a thioether bond, an amide bond, a carbamate bond, or an ether bond;
Y represents an aliphatic, an aromatic or a heterocyclic unit attached to the drug via a disulfide bond;
l is 0 or 1;
m is an integer from 2 to 8; and
n is an integer from 1 to 24.
In certain embodiments, m is an integer from 2 to 6.
In certain embodiments, m is an integer from 3 to 5.
Also, In certain embodiments, n is an integer form 2 to 8.

Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids can also be linked to anti-FOLR1 antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-maytansinoid conjugates with non-cleavable links can also be prepared. Such crosslinkers are described in the art (see ThermoScientific Pierce Crosslinking Technical Handbook and US Patent Application Publication No. 2005/0169933) and include but are not limited to, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), β-maleimidopropanoic acid N-succinimidyl ester (BMPS), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI), N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP). In certain embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, protein hormones, protein growth factors and other proteins are made in the same way.

In another aspect of the invention, the FOLR1 antibody (e.g. huMov19, FR1-21, FR1-48, FR1-49, FR1-57, or FR1-65) is linked to the drug via a non-cleavable bond through the intermediacy of a PEG spacer. Suitable crosslinking reagents comprising hydrophilic PEG chains that form linkers between a drug and the anti-FOLR1 antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, $Z-X_1-(-CH_2-CH_2-O-)_n-Y_p-D$, by methods described in detail in US Patent Publication 20090274713 and in WO2009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-FOLR1 antibody drug conjugate of formula (II) or of formula (II'):

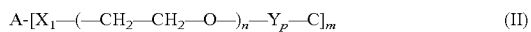

$$A-[X_1-(-CH_2-CH_2-O-)_n-Y_p-C]_m \quad (II)$$

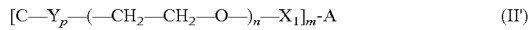

$$[C-Y_p-(-CH_2-CH_2-O-)_n-X_1]_m-A \quad (II')$$

wherein, A represents an anti-FOLR1 antibody or fragment;

C represents a cytotoxin or drug;

X represents an aliphatic, an aromatic or a heterocyclic unit bonded to the cell-binding agent via a thioether bond, an amide bond, a carbamate bond, or an ether bond;

Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;

l is 0 or 1;

p is 0 or 1;

m is an integer from 2 to 15; and n is an integer from 1 to 2000.

In a certain embodiment, m is an integer from 2 to 8; and n is an integer from 1 to 24.

In a certain embodiment, m is an integer from 2 to 6.

In a certain embodiment, n is an integer from 2 to 8.

In a certain embodiment, m is an integer from 3 to 5. In a certain embodiment, the antibody is huMov19. In another embodiment, the antibody is FR-1-21. In another embodiment, the antibody is FR-1-48. In another embodiment, the antibody is FR-1-49. In another embodiment, the antibody is FR-1-57. In another embodiment, the antibody is FR-1-65. Examples of suitable PEG-containing linkers include linkers having an N-succinimidyl ester or N-sulfosuccinimidyl ester moiety for reaction with the anti-FOLR1 antibody or fragment thereof, as well as a maleimido- or haloacetyl-based moiety for reaction with the compound. A PEG spacer can be incorporated into any crosslinker known in the art by the methods described herein.

Many of the linkers disclosed herein are described in detail in U.S. Patent Publication Nos. 20050169933 and 20090274713, and in WO2009/0134976; the contents of which are entirely incorporated herein by reference.

The present invention includes aspects wherein about 2 to about 8 drug molecules ("drug load"), for example, maytansinoid, are linked to an anti-FOLR1 antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-FOLR1 antibody or fragment thereof). In one aspect the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). In certain embodiments, the drug is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl)maytansine (DM4). Thus, in a certain embodiment, the antibody huMov19 is conjugated to DM1 or DM4. In another embodiment, the antibody FR-1-21 is conjugated to DM1 or DM4. In another embodiment, the antibody FR-1-48 is conjugated to DM1 or DM4. In another embodiment, the antibody FR-1-49 is conjugated to DM1 or DM4. In another embodiment, the antibody FR-1-57 is conjugated to DM1 or DM4. In another embodiment, the antibody FR-1-65 is conjugated to DM1 or DM4.

Thus, in one aspect, an immunoconjugate comprises 1 maytansinoid per antibody. In another aspect, an immunoconjugate comprises 2 maytansinoids per antibody. In another aspect, an immunoconjugate comprises 3 maytansinoids per antibody. In another aspect, an immunoconjugate comprises 4 maytansinoids per antibody. In another aspect, an immunoconjugate comprises 5 maytansinoids per antibody. In another aspect, an immunoconjugate comprises 6 maytansinoids per antibody. In another aspect, an immunoconjugate comprises 7 maytansinoids per antibody. In another aspect, an immunoconjugate comprises 8 maytansinoids per antibody.

In one aspect, an immunoconjugate comprises about 1 to about 8 maytansinoids per antibody. In another aspect, an immunoconjugate comprises about 2 to about 7 maytansinoids per antibody. In another aspect, an immunoconjugate comprises about 2 to about 6 maytansinoids per antibody. In another aspect, an immunoconjugate comprises about 2 to about 5 maytansinoids per antibody. In another aspect, an immunoconjugate comprises about 3 to about 5 maytansinoids per antibody. In another aspect, an immunoconjugate comprises about 3 to about 4 maytansinoids per antibody.

In one aspect, a composition comprising immunoconjugates has an average of about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1) drug molecules (e.g., maytansinoids) attached per antibody. In one aspect, a composition comprising immunoconjugates has an average of about 1 to about 8 drug molecules (e.g., maytansinoids) per antibody. In one aspect, a composition comprising immunoconjugates has an average of about 2 to about 7 drug molecules (e.g., maytansinoids) per antibody. In one aspect, a composition comprising immunoconjugates has an average of about 2 to about 6 drug molecules (e.g., maytansinoids) per antibody. In one aspect, a composition comprising immunoconjugates has an average of about 2 to about 5 drug molecules (e.g., maytansinoids) per antibody. In one aspect, a composition comprising immunoconjugates has an average of about 3 to about 5 drug molecules (e.g., maytansinoids) per antibody. In one aspect, a composition comprising immunoconjugates has an average of about 3 to about 4 drug molecules (e.g., maytansinoids) per antibody. In one aspect, a composition comprising immunoconjugates has an average of about 3.5 to about 4 drug molecules (e.g., maytansinoids) per antibody.

In one aspect, a composition comprising immunoconjugates has an average of about 2±0.5, about 2.5±0.5, about 3±0.5, about 3.5±0.5, about 4±0.5, about 4.5±0.5, about 5±0.5, about 5.5±0.5, about 6±0.5, about 6.5±0.5, about 7±0.5, about 7.5±0.5, or about 8±0.5 drug molecules (e.g., maytansinoids) attached per antibody. In one aspect, a composition comprising immunoconjugates has an average of about 3.5±0.5 drug molecules (e.g., maytansinoids) per antibody.

The anti-FOLR1 antibody or fragment thereof can be modified by reacting a bifunctional crosslinking reagent with the anti-FOLR1 antibody or fragment thereof, thereby resulting in the covalent attachment of a linker molecule to the anti-FOLR1 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-FOLR1 antibody or fragment" refers to the conjugate molecule comprising at least one drug derivative bound to a cell-binding agent anti-FOLR1 antibody or fragment via a suitable linking group, or a precursor thereof. In certain embodiments, the linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

(III)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (IV):

(IV)

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula (V):

(V)

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In certain embodiments, the C-3 position is utilized. In certain embodiments, the C-3 position of maytansinol is utilized.

Structural representations of certain conjugates are shown below:

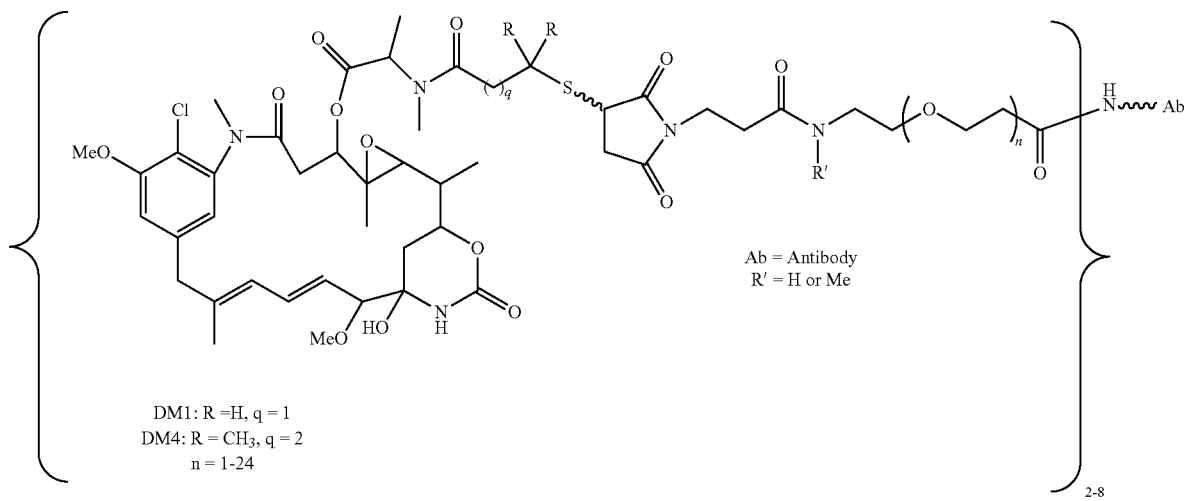

Ab-PEG-Mal-DM1/DM4 (VI)

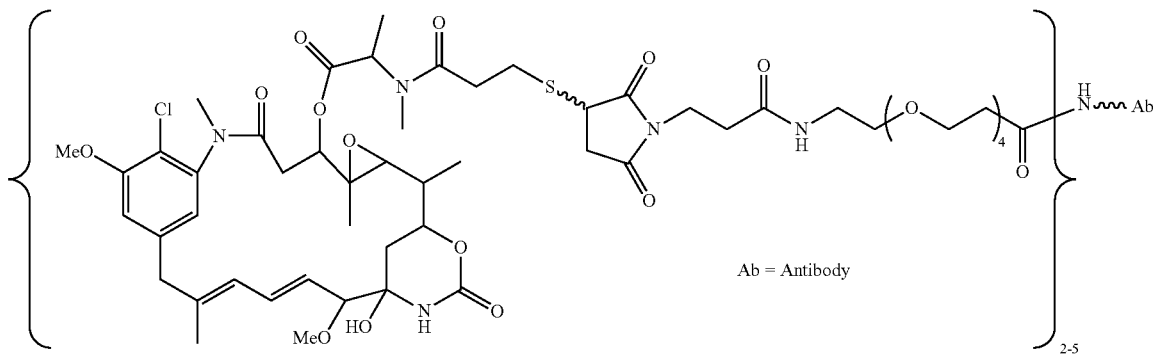

Ab-PEG4-Mal-DM1 (VII)

-continued
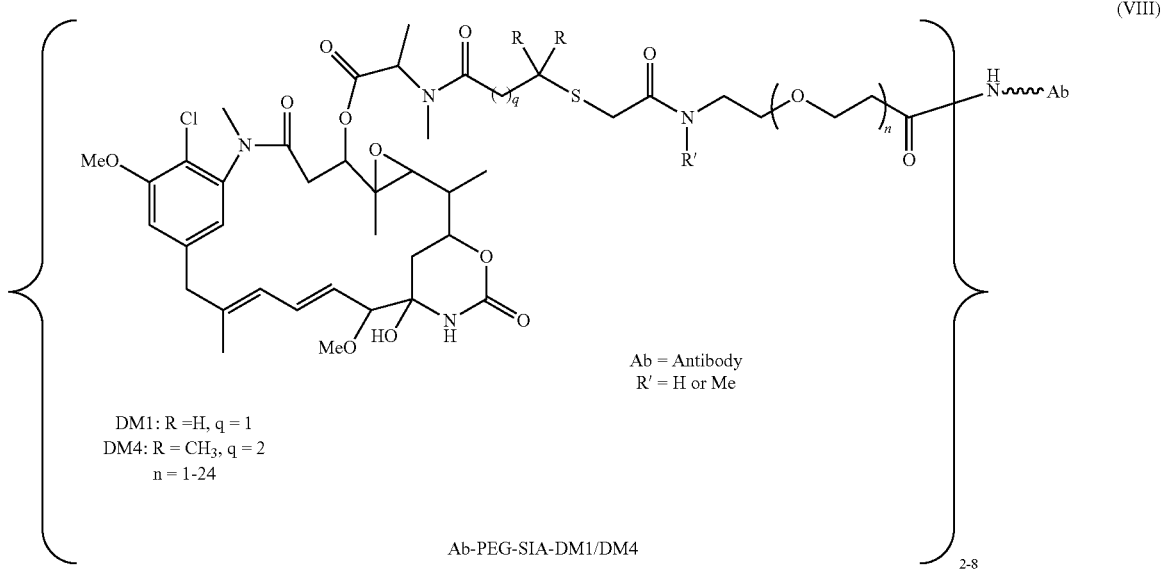
Ab-PEG-SIA-DM1/DM4
(VIII)
DM1: R = H, q = 1
DM4: R = CH₃, q = 2
n = 1-24
Ab = Antibody
R' = H or Me
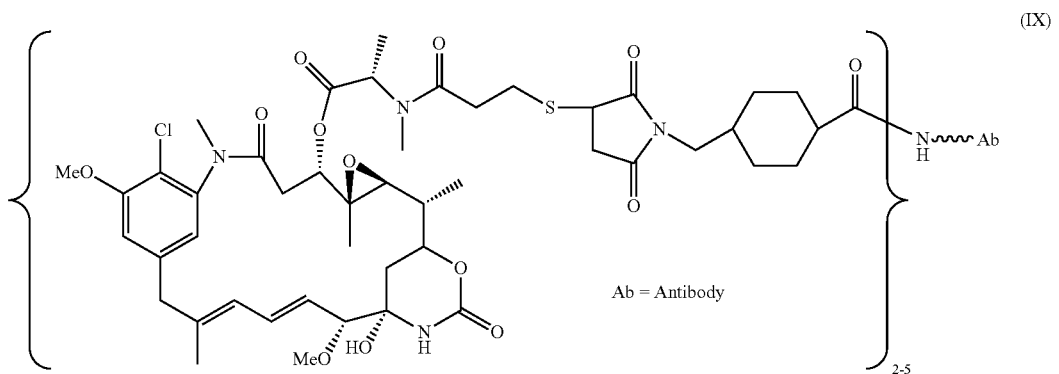
Ab-SMCC-DM1
(IX)
Ab = Antibody
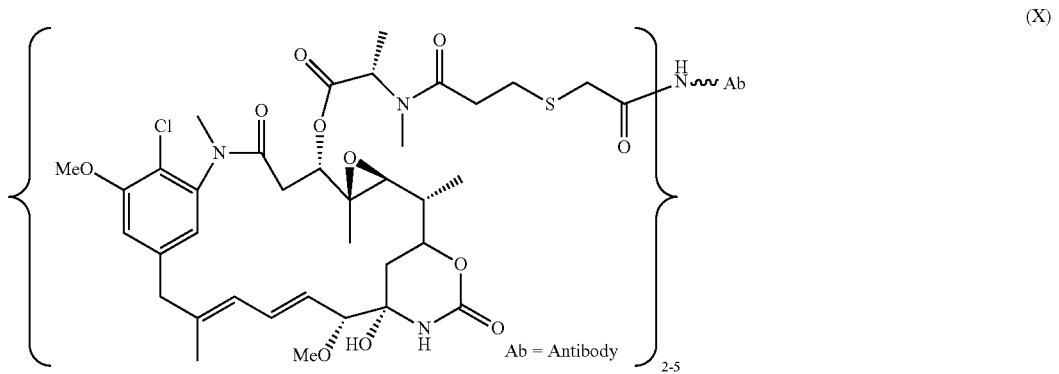
Ab-SIA-DM1
(X)
Ab = Antibody (XI)

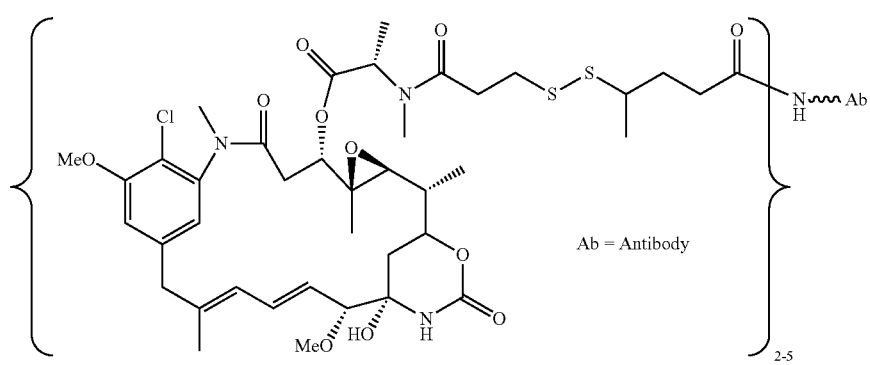

Ab-SPP-DM1

(XII)

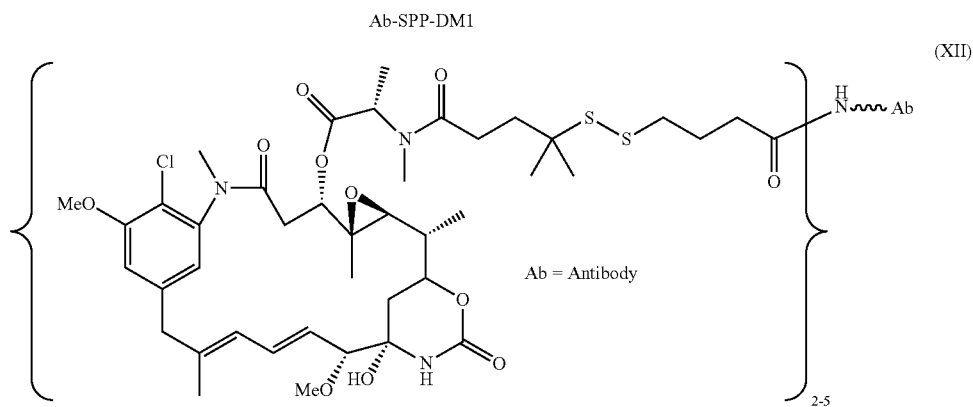

Ab-SPDB-DM4

(XIII)

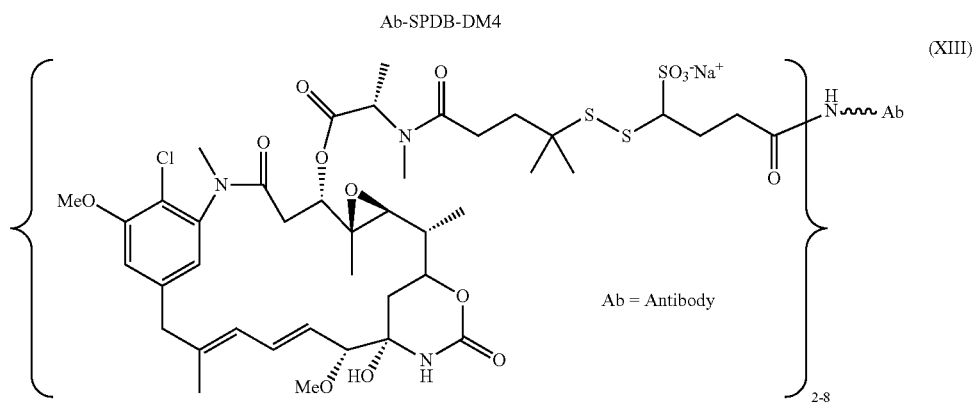

Ab-sulfo-SPDB-DM4

In a certain embodiment, the antibody is huMov19. In another embodiment, the antibody is FR1-21.

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration. The number of maytansinoid molecules bound per antibody molecule can be determined by measuring spectrophotometrically the ratio of the absorbance at 252 nm and 280 nm. An average of 1-10 maytansinoid molecules/antibody molecule is used and an average of 2-5 is also used in certain embodiments. The average number of maytansinoid molecules/antibody can be, for example, about 1-10, 2-5, 3-4, 3.5-4 or 3.5. In one aspect, the average number of maytansinoid molecules/antibody is about 3.5±0.5. In one aspect, the average number of maytansinoid molecules/antibody is about 3.5-4.

Conjugates of antibodies with maytansinoid drugs can be evaluated for their ability to suppress proliferation of various unwanted cell lines in vitro. For example, cell lines such as the human KB cell line, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

Benzodiazepine compounds described, for example, in U.S. Patent Application Publication No. 2010/0203007 (e.g., indolinobenzodiazepines or oxazolidinobenzodiazepines), derivatives thereof, intermediates thereof, may also be used to prepare anti-FOLR1 antibody fragment or conjugates.

Useful benzodiazepines include compounds of formula (XIV), (XV) and (XVI), in which the dimer compounds optionally bear a linking group that allows for linkage to cell binding agents.

to 10 carbon atoms, a polyethylene glycol unit (—OCH$_2$CH$_2$)n, wherein n is an integer from 1 to 2000, aryl having from 6 to 10 carbon atoms, heterocyclic ring having from 3 to 10 carbon atoms wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein the definitions of R$_7$, R$_8$, R$_9$, R$_{10}$, R$_{11}$ and R$_{12}$ are as given above, optionally R" is OH;

W is C=O, C=S, CH$_2$, BH, SO or SO$_2$;

R$_1$, R$_2$, R$_3$, R$_4$, R$_1$', R$_2$', R$_3$' and R$_4$' are each independently selected from H, substituted or unsubstituted linear, branched or cyclic alkyl, alkenyl or alkynyl having from 1 to 10 carbon atoms, a polyethylene glycol unit (—OCH$_2$CH$_2$)n, wherein n is an integer from 1 to 2000, or a substituent selected from a halogen, guanidinium [—NH(C=NH)NH$_2$], OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$,

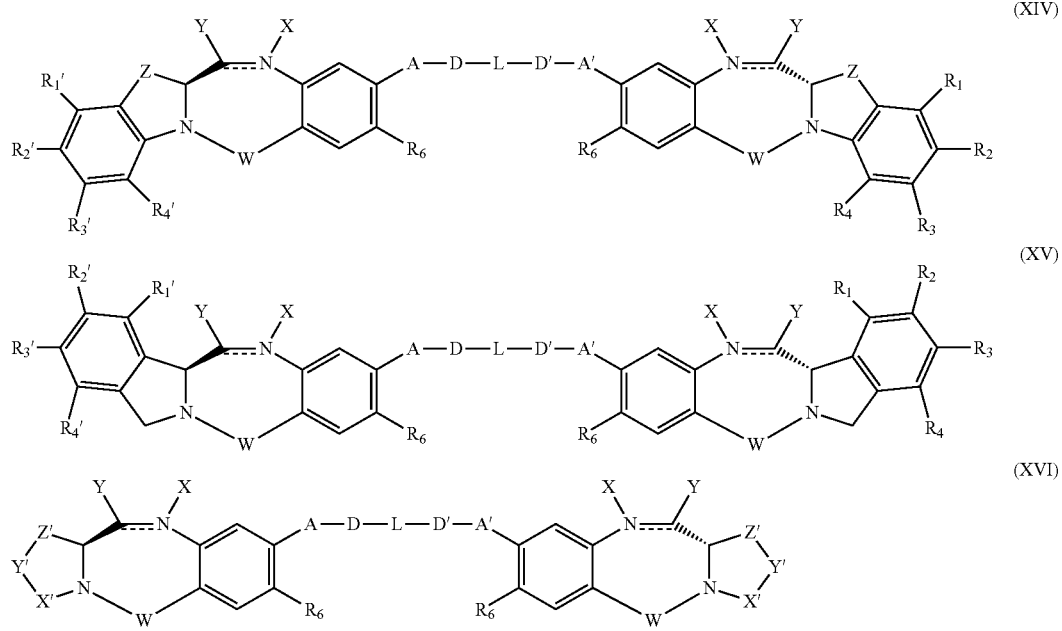

wherein the double line=between N and C represents a single bond or a double bond, provided that when it is a double bond X is absent and Y is H, and when it is a single bond, X is H or an amine protecting moiety that converts the compound into a prodrug;

Y is selected from —OR, an ester represented by —OCOR', a carbonate represented by —OCOOR', a carbamate represented by —OCONR'R", an amine or a hydroxyl amine represented by NR'R", amide represented by —NRCOR', a peptide represented by NRCOP, wherein P is an amino acid or a polypeptide containing between 2 to 20 amino acid units, a thioether represented by SR', a sulfoxide represented by SOR', a sulfone represented by —SO$_2$R', a sulfite —SO$_3$, a bisulfite —OSO$_3$, a halogen, cyano, an azido, or a thiol, wherein R, R' and R" are same or different and are selected from H, substituted or unsubstituted linear, branched or cyclic alkyl, alkenyl or alkynyl having from 1

OCOR$_{11}$ or OCONR$_{11}$R$_{12}$ wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, aryl having from 6 to 10 carbon atoms, heterocyclic ring having from 3 to 10 carbon atoms, optionally R$_{10}$ is SR$_{13}$ or COR$_{13}$, wherein R$_{13}$ is selected from linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, aryl having from 6 to 10 carbon atoms, heterocyclic ring having from 3 to 10 carbon atoms, optionally R$_{11}$ is OR$_{14}$, wherein R$_{14}$ has the same definition as R, optionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, poly-indolyl, poly-imidazolyl, polypyrrolloimidazolyl, poly-pyrollo-indolyl or polyimidazolo-indolyl unit optionally bearing a linking group that enables linkage to a cell binding agent;

Z is selected from $(CH_2)_n$, wherein n is 1, 2 or 3, $CR_{15}R_{16}$, $NR_{17}$, O or S, wherein $R_{15}$, $R_{16}$ and $R_{17}$ are each independently selected from H, linear, branched or cyclic alkyl having from 1 to 10 carbon atoms, a polyethylene glycol unit $(-OCH_2CH_2)_n$, wherein n is an integer from 1 to 2000;

$R_6$ is OR, SR or NRR', wherein R and R' have the same definition as given above;

X' is selected from $CH_2$, NR, CO, BH, SO or $SO_2$ wherein R has the same definition as given above;

Y' is O, $CH_2$, NR or S, wherein R has the same definition as given above;

Z' is $CH_2$ or $(CH_2)_n$, wherein n is 2, 3 or 4, provided that X', Y' and Z' are not all $CH_2$ at the same time;

A and A' are the same or different and are selected from O, —CRR'O, S, —CRR'S, —$NR_{15}$ or CRR'NHR$_{15}$, wherein R and R' have the same definition as given above and wherein $R_{15}$ has the same definition as given above for R;

D and D' are same or different and independently selected from linear, branched or cyclic alkyl, alkenyl or alkynyl having 1 to 10 carbon atoms, optionally substituted with any one of halogen, $OR_7$, $NR_8R_9$, $NO_2$, NRCOR', $SR_{10}$, a sulfoxide represented by SOR', a sulfone represented by —$SO_2R'$, a sulfite —$SO_3$, a bisulfite —$OSO_3$, a sulfonamide represented by $SO_2NRR'$, cyano, an azido, —$COR_{11}$, $OCOR_{11}$ or $OCONR_{11}R_{12}$, wherein the definitions of $R_7$, $R_8$, $R_9$, $R_{10}$, $R_{11}$ and $R_{12}$ are as given above, a polyethylene glycol unit $(-OCH_2CH_2)_n$, wherein n is an integer from 1 to 2000;

L is an optional phenyl group or a heterocycle ring having from 3 to 10 carbon atoms that is optionally substituted, wherein the substituent is a linking group that enables linkage to a cell binding agent via a covalent bond, or is selected from linear, branched or cyclic alkyl, alkenyl or alkynyl having from 1 to 10 carbon atoms, optionally substituted with any one of halogen, $OR_7$, $NR_8R_9$, $NO_2$, NRCOR', $SR_{10}$, a sulfoxide represented by SOR', a sulfone represented by —$SO_2R'$, a sulfite —$SO_3$, a bisulfite —$OSO_3$, a sulfonamide represented by $SO_2NRR'$, cyano, an azido, —$COR_{11}$, $OCOR_{11}$ or $OCONR_{11}R_{12}$, wherein the definitions of $R_7$, $R_8$, $R_9$, $R_{10}$, $R_{11}$ and $R_{12}$ are as given above, a polyethylene glycol unit $(-OCH_2CH_2)n$, wherein n is an integer from 1 to 2000; optionally, L itself is a linking group that enables linkage to a cell binding agent via a covalent bond; or their pharmaceutically acceptable solvates, salts, hydrates or hydrated salts, their optical isomers, racemates, diastereomers, enantiomers or the polymorphic crystalline structures of these compounds; provided that the compound has no more than one linking group that enables linkage to a cell binding agent via a covalent bond.

In one aspect, the double line $=$ between N and C represents a single bond or a double bond, provided that when it is a double bond X is absent and Y is H, and when it is a single bond, X is H or an amine protecting group that converts the compound into a prodrug;

Y is selected from —OR, NR'R", a sulfite —$SO_3$, or a bisulfite —$OSO_3$, wherein R is selected from H, linear, branched or cyclic alkyl, alkenyl or alkynyl having from 1 to 10 carbon atoms, a polyethylene glycol unit $(-OCH_2CH_2)_n$, wherein n is an integer from 1 to 2000, aryl having from 6 to 10 carbon atoms, heterocyclic ring having from 3 to 10 carbon atoms;

W is C=O, $CH_2$ or $SO_2$;

$R_1$, $R_2$, $R_3$, $R_4$, $R_1'$, $R_2'$, $R_3'$ and $R_4'$ are each independently selected from H, $NO_2$ or a linking group that enables linkage to a cell binding agent via a covalent bond;

$R_6$ is $OR_{18}$, wherein $R_{18}$ has the same definition as R;

Z is selected from $(CH_2)n$, wherein n is 1, 2 or 3, $CR_{15}R_{16}$, $NR_{17}$, O or S, wherein $R_{15}$, $R_{16}$ and $R_{17}$ are each independently selected from H, linear, branched or cyclic alkyl having from 1 to 10 carbon atoms, a polyethylene glycol unit $(-OCH_2CH_2)_n$, wherein n is an integer from 1 to 2000;

X' is selected from $CH_2$, or C=O;

Y' is O, NR, or S, wherein R is defined as above;

Z' is $CH_2$ or $(CH_2)_2$;

A and A' are each O;

D and D' are same or different and independently selected from linear, branched or cyclic alkyl, alkenyl or alkynyl having from 1 to 10 carbon atoms;

L is an optional phenyl group or a heterocycle ring having from 3 to 10 carbon atoms that is optionally substituted, wherein the substituent is a linking group that enables linkage to a cell binding agent via a covalent bond, or is selected from linear, branched or cyclic alkyl, alkenyl or alkynyl having from 1 to 10 carbon atoms, optionally substituted with any one of halogen, $OR_7$, $NR_8R_9$, $NO_2$, NRCOR', $SR_{10}$, a sulfoxide represented by SOR', a sulfone represented by —$SO_2R'$, a sulfite —$SO_3$, a bisulfite —$OSO_3$, a sulfonamide represented by $SO_2NRR'$, cyano, an azido, —$COR_{11}$, $OCOR_{11}$ or $OCONR_{11}R_{12}$, a polyethylene glycol unit $(-OCH_2CH_2)n$, wherein n is an integer from 1 to 2000; optionally, L itself is a linking group that enables linkage to a cell binding agent via a covalent bond; or their pharmaceutically acceptable solvates, salts, hydrates or hydrated salts, their optical isomers, racemates, diastereomers, enantiomers or the polymorphic crystalline structures of these compounds.

In another aspect the compound is represented by formula (XVII):

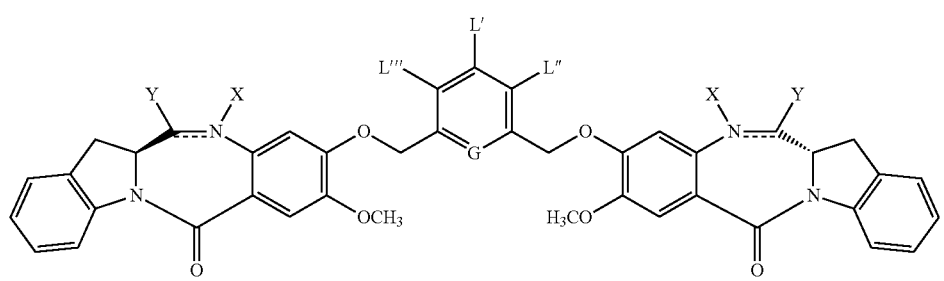

wherein the double line ═ between N and C represents a single bond or a double bond, provided that when it is a double bond X is absent and Y is H, and when it is a single bond, X is H or an amine protecting group that converts the compound into a prodrug, and Y is selected from OH, an ether represented by —OR, a sulfite —SO₃, or a bisulfite —OSO₃, wherein R is selected from linear, branched or cyclic alkyl, alkenyl or alkynyl bearing from 1 to 10 carbon atoms one of R2, R3 is a linking group that enables linkage to a cell binding agent via a covalent bond and the other is H, one of L', L" or L''' is a linking group that enables linkage to a cell binding agent, while the others are H; L' can be the linking group and G is CH or N. Other examples are described in U.S. Patent Application No. 61/150,201, the entire content of which is incorporated herein by reference. Thus, in a certain embodiment, the antibody huMov19 is conjugated to a benzodiazepene having a structure shown in XIX-XXII above. In another embodiment, the antibody FR-1-21 is conjugated to a benzodiazepene having a structure shown in XIX-XXII above.

IV. Polynucleotides

In certain embodiments, the invention encompasses polynucleotides comprising polynucleotides that encode a polypeptide that specifically binds a human FOLR1 receptor or a fragment of such a polypeptide. For example, the invention provides a polynucleotide comprising a nucleic acid sequence that encodes an antibody to a human FOLR1 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (antisense) strand.

In certain embodiments, the polynucleotides are isolated. In certain embodiments, the polynucleotides are substantially pure.

The invention provides a polynucleotide comprising a polynucleotide encoding a polypeptide comprising a sequence selected from the group consisting of SEQ ID NOs: 4, 10, 11, 41, 42, and 88-103. Also provided is a polynucleotide encoding a polypeptide having at least about 95%, at least about 96%, at least about 97%, at least about 98%, or at least about 99% sequence identity to SEQ ID NOs: 4, 10, 11, 41, 42, and 88-103.

The polynucleotides SEQ ID NOs: 5, 14, and 15 comprise the coding sequence for huMov19 variable domain heavy chain, variable domain light chain version 1.00, and variable domain light chain version 1.60, respectively.

The invention further provides a polynucleotide comprising a sequence selected from the group consisting of SEQ ID NOs:5, 14, 15, 37, 38, 43, 44, 47, 48, and 120-127. Also provided is a polynucleotide having at least about 95%, at least about 96%, at least about 97%, at least about 98%, or at least about 99% sequence identity to SEQ ID NOs: 5, 14, 15, 37, 38, 43, 44, 47, 48, and 120-127. Thus, in certain embodiments, the polynucleotide comprises (a) a polynucleotide having at least about 95% sequence identity to SEQ ID NO:5, and/or (b) a polynucleotide having at least about 95% sequence identity to SEQ ID NO:14 or 15. In certain embodiments, the polynucleotide comprises (a) a polynucleotide having the amino acid sequence of SEQ ID NO: 5; and/or (b) a polynucleotide having the amino acid sequence of SEQ ID NO:14 or SEQ ID NO:15.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also provided.

V. Methods of use and Pharmaceutical Compositions

The FOLR1-binding agents (including antibodies, immunoconjugates, and polypeptides) of the invention are useful in a variety of applications including, but not limited to, therapeutic treatment methods, such as the treatment of cancer. In certain embodiments, the agents are useful for inhibiting tumor growth, inducing differentiation, reducing tumor volume, and/or reducing the tumorigenicity of a tumor. The methods of use may be in vitro, ex vivo, or in vivo methods. In certain embodiments, the FOLR1-binding agent or antibody or immunoconjugate, or polypeptide is an antagonist of the human FOLR1 to which it binds.

In one aspect, anti-FOLR1 antibodies and immunoconjugates of the invention are useful for detecting the presence of FOLR1 in a biological sample. The term "detecting" as used herein encompasses quantitative or qualitative detection. In certain embodiments, a biological sample comprises a cell or tissue. In certain embodiments, such tissues include normal and/or cancerous tissues that express FOLR1 at higher levels relative to other tissues. In certain embodiments, FOLR1 overexpression detects the presence of ovarian cancer, lung cancer, brain cancer, breast cancer, uterine cancer, renal cancer or pancreatic cancer.

In one aspect, the invention provides a method of detecting the presence of FOLR1 in a biological sample. In certain embodiments, the method comprises contacting the biological sample with an anti-FOLR1 antibody under conditions permissive for binding of the anti-FOLR1 antibody to FOLR1, and detecting whether a complex is formed between the anti-FOLR1 antibody and FOLR1.

In one aspect, the invention provides a method of diagnosing a disorder associated with increased expression of FOLR1. In certain embodiments, the method comprises contacting a test cell with an anti-FOLR1 antibody; determining the level of expression (either quantitatively or qualitatively) of FOLR1 by the test cell by detecting binding of the anti-FOLR1 antibody to FOLR1; and comparing the level of expression of FOLR1 by the test cell with the level of expression of FOLR1 by a control cell (e.g., a normal cell of the same tissue origin as the test cell or a cell that expresses FOLR1 at levels comparable to such a normal cell), wherein a higher level of expression of FOLR1 by the test cell as compared to the control cell indicates the presence of a disorder associated with increased expression of FOLR1. In certain embodiments, the test cell is obtained from an individual suspected of having a disorder associated with increased expression of FOLR1. In certain embodiments, the disorder is a cell proliferative disorder, such as a cancer or a tumor.

In certain embodiments, a method of diagnosis or detection, such as those described above, comprises detecting binding of an anti-FOLR1 antibody to FOLR1 expressed on the surface of a cell or in a membrane preparation obtained from a cell expressing FOLR1 on its surface. In certain embodiments, the method comprises contacting a cell with an anti-FOLR1 antibody under conditions permissive for binding of the anti-FOLR1 antibody to FOLR1, and detecting whether a complex is formed between the anti-FOLR1 antibody and FOLR1 on the cell surface. An exemplary assay for detecting binding of an anti-FOLR1 antibody to FOLR1 expressed on the surface of a cell is a "FACS" assay.

Certain other methods can be used to detect binding of anti-FOLR1 antibodies to FOLR1. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-FOLR1 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-FOLR1 antibodies are immobilized on an insoluble matrix. Immobilization entails separating the anti-FOLR1 antibody from any FOLR1 that remains free in solution. This conventionally is accomplished by either insolubilizing the anti-FOLR1 antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-FOLR1 antibody after formation of a complex between the anti-FOLR1 antibody and FOLR1, e.g., by immunoprecipitation.

Any of the above embodiments of diagnosis or detection may be carried out using an immunoconjugate of the invention in place of or in addition to an anti-FOLR1 antibody.

In certain embodiments, the disease treated with the FOLR1-binding agent or antagonist (e.g., a huMov19 antibody or immunoconjugate) is a cancer. In certain embodiments, the cancer is characterized by tumors expressing folate receptor 1 to which the FOLR1-binding agent (e.g., antibody) binds.

The present invention provides for methods of treating cancer comprising administering a therapeutically effective amount of a FOLR1-binding agent to a subject (e.g., a subject in need of treatment). In certain embodiments, the cancer is a cancer selected from the group consisting of colorectal cancer, pancreatic cancer, lung cancer, ovarian cancer, liver cancer, breast cancer, brain cancer, kidney cancer, prostate cancer, gastrointestinal cancer, melanoma, cervical cancer, bladder cancer, glioblastoma, and head and neck cancer. In certain embodiments, the cancer is ovarian cancer. In certain embodiments, the cancer is lung cancer. In certain embodiments, the subject is a human.

The present invention further provides methods for inhibiting tumor growth using the antibodies or other agents described herein. In certain embodiments, the method of inhibiting the tumor growth comprises contacting the cell with a FOLR1-binding agent (e.g., antibody) in vitro. For example, an immortalized cell line or a cancer cell line that expresses FOLR1 is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added an FOLR1-binding agent to inhibit tumor growth.

In some embodiments, the method of inhibiting tumor growth comprises contacting the tumor or tumor cells with the FOLR1-binding agent (e.g., antibody) in vivo. In certain embodiments, contacting a tumor or tumor cell with a FOLR1-binding agent is undertaken in an animal model. For example, FOLR1-binding agents can be administered to xenografts expressing one or more FOLR1s that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a FOLR1-binding agent to inhibit tumor cell growth. In some embodiments, the FOLR1-binding agent is administered at the same time or shortly after introduction of tumorigenic cells into the animal to prevent tumor growth. In some embodiments, the FOLR1-binding agent is administered as a therapeutic after the tumorigenic cells have grown to a specified size.

In certain embodiments, the method of inhibiting tumor growth comprises administering to a subject a therapeutically effective amount of a FOLR1-binding agent. In certain embodiments, the subject is a human. In certain embodiments, the subject has a tumor or has had a tumor removed.

In certain embodiments, the tumor expresses the folate receptor to which the FOLR1-binding agent or antibody binds. In certain embodiments, the tumor overexpresses the human FOLR1.

In certain embodiments, the tumor is a tumor selected from the group consisting of brain tumor, colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is an ovarian tumor.

In addition, the invention provides a method of reducing the tumorigenicity of a tumor in a subject, comprising administering a therapeutically effective amount of a FOLR1-binding agent to the subject. In certain embodiments, the tumor comprises cancer stem cells. In certain embodiments, the frequency of cancer stem cells in the tumor is reduced by administration of the agent.

Thus, in certain embodiments the inventions provides methods of treating cancer using huMov19 antibody and immunoconjugates. In certain embodiments, the huMov19 immunoconjugate is huMov19-SPDB-DM4; huMov19-sulfo-SPP-DM1; huMov19-SPP-DM1; or huMov19-PEG4-Mal-DM4.

The invention further provides methods of differentiating tumorigenic cells into non-tumorigenic cells comprising contacting the tumorigenic cells with a FOLR1-binding agent (for example, by administering the FOLR1-binding agent to a subject that has a tumor comprising the tumorigenic cells or that has had such a tumor removed. In certain embodiments, the tumorigenic cells are ovarian tumor cells.

The present invention further provides methods of reducing myofibrolblast activation in the stroma of a solid tumor, comprising contacting the stroma with an effective amount of the FOLR1-binding agent, polypeptide or antibody.

The present invention further provides pharmaceutical compositions comprising one or more of the FOLR1-binding agents described herein. In certain embodiments, the pharmaceutical compositions further comprise a pharmaceutically acceptable vehicle. These pharmaceutical compositions find use in inhibiting tumor growth and treating cancer in human patients.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

An antibody or immunoconjugate of the invention can be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other. Pharmaceutical compositions comprising the FOLR1-binding agent and the second anti-cancer agent are also provided.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the antibody or other FOLR1-binding agent is given once every two weeks or once every three weeks. In certain embodiments, the dosage of the antibody or other FOLR1-binding agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

VI. Kits Comprising FOLR1-binding Agents

The present invention provides kits that comprise the antibodies, immunoconjugates or other agents described herein and that can be used to perform the methods described herein. In certain embodiments, a kit comprises at least one purified antibody against human folate receptor 1 in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies, immunoconjugates or other agents of the present invention can be readily incorporated into one of the established kit formats which are well known in the art.

Further provided are kits comprising a FOLR1-binding agent (e.g., a FOLR1-binding antibody), as well as a second anti-cancer agent. In certain embodiments, the second anti-cancer agent is a chemotherapeutic agent (e.g., gemcitabine or irinotecan).

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1

Chimerization of Murine Monoclonal Antibody Mov19

The variable region amino acid sequences for Mov19 were obtained from the NCBI database (accessions CAA68253 for the light chain (SEQ ID NO:24) and CAA68252 for the heavy chain (SEQ ID NO:23)) and then codon-optimized and synthesized by Blue Heron Biotechnology. The light chain variable region was cloned into the EcoRI and BsiWI sites of the pAbKZeo plasmid and the heavy chain variable region was cloned into the HindIII and Apa1 sites of the pAbG1Neo plasmid.

Example 2

Humanization of Murine Monoclonal Antibodies Mov19 and FR1-21

The Mov19 antibody was humanized following framework resurfacing methods previously described (Roguska M. et. al, *Proc. Natl. Acad Sci. USA* 1994 February; 91:969-973) and (Roguska et al., Protein Eng. 9(10):895-904 (1996)). Briefly, the average solvent accessibility for each variable region framework residue was calculated using closely related solved antibody structures from the PDB database, and positions with greater than a 30% average accessibility were marked as surface residues (Pedersen J. T. et. Al, J. Mol. Biol. 1994; 235: 959-973). The human surface replacement sequence was selected by aligning the surface positions of murine antibody sequences with the corresponding positions of the human antibody germline sequences in the Kabat database (Johnson, G. and Wu, T. T. (2001) *Nucleic Acids Research,* 29: 205-206). The most homologous human light chain variable region surface (clone DPK19, IMGT locus IGKV2D-30*01 for Mov19 and IMGT locus IGKV1/OR2-0*01 for FR1-21) and the most homologous human heavy chain variable region surface (clone 8M27, IMGT locus IGHV1-69*08 for Mov19 and IMGT locus IGHV5-51*02 for FR1-21) was selected to replace the murine Mov19 framework surface positions, leaving the 6 CDRs (Table 1) unaltered. The murine and human Mov19 and FR1-21 surface positions and residues are given in FIGS. 1A-D.

TABLE 1A

The Mov19 and FR1-21 light and heavy chain CDRs as defined for resurfacing are provided. The Kabat definition for heavy chain CDR2 is also given for both the murine and human antibodies.

| Mov19 CDRs | FR1-21 CDRs |
|---|---|
| *Light Chain* | |
| CDR1: KASQSVSFAGTSLMH (SEQ ID NO: 7) | CDR1: KASDHINNWLA (SEQ ID NO: 27) |
| CDR2: RASNLEA (SEQ ID NO: 8) | CDR2: GATSLET (SEQ ID NO: 28) |
| CDR3: QQSREYPYT (SEQ ID NO: 9) | CDR3: QQYWSTPFT (SEQ ID NO: 29) |
| *Heavy Chain* | |
| CDR1: GYFMN (SEQ ID NO: 1) | CDR1: SSYGMS (SEQ ID NO: 30) |
| CDR2 (AbM): RIHPYDGDTF (SEQ ID NO: 131) | CDR2 (AbM): TISSGGSYTY (SEQ ID NO: 31) |
| CDR3: YDGSRAMDY (SEQ ID NO: 3) | CDR3: DGEGGLYAMDY (SEQ ID NO: 32) |
| Kabat Defined Mov19 HC CDR2 | Kabat Defined FR1-21 HC CDR2 |
| *Murine* | |
| HC CDR2: RIHPYDGDTF<u>YNQNFKD</u> (SEQ ID NO: 128) | HC CDR2: TISSGGSYTYYPDGVKG (SEQ ID NO: 33) |
| *Human* | |
| HC CDR2: RIHPYDGDTF<u>YNQKFQG</u> (SEQ ID NO: 2) | HC CDR2: TISSGGSYTYYSPGFQG (SEQ ID NO: 34) |

None of the residue changes raised concerns for impacting the interactions of either the Mov19 or FR1-21 CDRs with their target epitopes on folate receptor 1, so no surface back mutations were considered for the humanized sequences of either antibody. The resurfaced Mov19 sequence did however introduce a consensus N-linked glycosylation site at the light chain N74 (light chain version 1.00), so a second humanized light chain version was made to remove this site. A review of the Kabat human light chain sequence database revealed that threonine is the most common residue found at light chain position 74 so the humanized Mov19 light chain version 1.60 was built with a threonine at position 74. Position 74 is not a surface residue so this residue substitution has no impact on the humanization by resurfacing. Alignments of the variable region sequences of murine and humanized Mov19, and FR1-21 are given in FIG. 2.

The variable region sequences for humanized Mov19 and FR1-21 were codon-optimized and synthesized by Blue Heron Biotechnology. The sequences are flanked by restriction enzyme sites to facilitate cloning in-frame with the respective constant sequences in single chain mammalian expression plasmids. The light chain variable region was cloned into the EcoRI and BsiWI sites of the pAbKZeo plasmid. The resulting plasmid DNAs encoding huMov19 light chain were deposited with the ATCC as ATCC Deposit Nos. PTA-10773 and PTA-10774 and the resulting plasmid DNA encoding huFR1-21 light chain was deposited as ATCC Deposit No. PTA-10776. The heavy chain variable region was cloned into the HindIII and ApaI sites of the pAbG1Neo plasmid. The resulting plasmid DNA encoding huMov19 heavy chain was deposited with the ATCC as ATCC Deposit No. PTA-10772 and the resulting plasmid DNA encoding huFR1-21 heavy chain was deposited as ATCC Deposit No. PTA-10775. These plasmids, were then transfected as described in example 3 to produce huMov19. The plasmid encoding either huMov19 light chain (i.e., that deposited as ATCC Deposit No. PTA-10773 or PTA-10774) can be paired with the plasmid encoding huMov19 heavy chain to create a huMov19 antibody according to the methods provided herein and as are well-known by one of ordinary skill in the art.

Example 3

Recombinant Antibody Expression

The chimeric and humanized antibody constructs were transiently produced in either adherent HEK-293T cells using a standard calcium phosphate procedure (BD Biosciences, CalPhos Mammalian Transfection Kit, Cat #631312) or in suspension adapted HEK-293T cells using a modified PEI procedure [Durocher Y, Perret S, Kamen A High-level and high-throughput recombinant protein production by transient transfection of suspension-growing human 293-EBNA1 cells. Nucleic Acids Res. 2002 Jan. 15; 30(2):E9] in spinner flasks. The PEI transient transfections were performed as previously described (Durocher, Y. et al., Nucleic Acids Res. 30(2):E9 (2002)), except the HEK-293T cells were grown in Freestyle 293 (Invitrogen) and the culture volume was left undiluted after the addition of the PEI-DNA complexes. Both the adherent and suspension transient transfections were incubated for a week and then the cleared supernatant was purified by a Protein A column followed by a CM column ion exchange chromatography as described below. As shown in FIG. 3, expression of huMov19 was at least 10-fold higher than expression of chimeric Mov19 in transfected cells.

Example 4

Antibody Purification

Antibodies were purified from cleared cell culture supernatants using standard methods, such as, for example Protein A or G chromatography (HiTrap Protein A or G HP, 1 mL, Amersham Biosciences). Briefly, supernatant was prepared for chromatography by the addition of 1/10 volume of 1 M Tris/HCl buffer, pH 8.0. The pH-adjusted supernatant was filtered through a 0.22 μm filter membrane and loaded onto column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1× PBS and sterilized by filtering through a 0.2 μm filter membrane. Purified antibody was quantified by absorbance at $A_{280}$.

Protein A purified fractions were further purified using ion exchange chromatography (IEX) with carboxymethyl (CM) chromatography. Briefly, samples from protein A purification were buffer exchanged into the start buffer (10 mM potassium phosphate, 10 mM sodium chloride, pH 7.5) and filtered through 0.22 μm filer. The prepared sample was then loaded onto a CM fast flow resin (GE lifesciences) that was equilibrated with the start buffer at a flow rate of 120 cm/hr. Column size was chosen to have sufficient capacity to bind all the antibody in the sample. The column was then washed with binding buffer until a stable baseline was obtained with no absorbance at 280 nm. Antibody was eluted by initiating a gradient from 10 mM to 500 mM sodium chloride in 20 column volume (CV). Fractions with the UV reading above 50 mAu of the major peak were collected. The purity (the percentage of monomer and soluble high molecular weight aggregates) was assessed with size exclusion chromatography (SEC) on a TSK gel G3000SWXL, 7.8×300 mm with a SWXL guard column, 6.0×40 mm (Tosoh Bioscience, Montgomeryville, Pa.) using an Agilent HPLC 1100 system (Agilent, Santa Clara, Calif.). Fractions with desired purity (>95%) were pooled, buffer exchanged to PBS (pH 7.4) using TFF system, and sterilized by filtering through a 0.2 μm filter membrane. Purified antibody was further tested for its purity by SEC and the IgG concentration was determined by absorbance measurement at 280 nm using an extinction coefficient of 1.47. Dilution was made if necessary. Alternatively, ceramic hydroxyapatite (CHT) can be used to polish both murine and humanized antibodies with improved selectivity. Type II CHT resin with 40 μm particle size (Bio-Rad Laboratories) was applied to the polishing of antibodies with similar protocol as IEX chromatography. The start buffer for CHT was 20 mM sodium phosphate, pH 7.0 and antibody was eluted with a gradient of 20-160 mM sodium phosphate over 20 CV.

Example 5

Development of Murine Anti-FOLR1 Antibodies

There were two different immunization/screening series. First series has led to generation of FR1-21 clone, second series has resulted in generation of FR1-48, FR1-49, FR1-57 and FR1-65 clones. In the first series mice were subcutaneously immunized with approximately $5 \times 10^6$ FOLR1-expressing KB cells (American Tissue Culture Collection, ATCC CCL-17). In the second series 300-19 cells expressing human FOLR1 on their surface were used to immunize mice. To make these cells, the human FOLR1 amino acid sequence was obtained from the NCBI website (accession NP_057937), then it was codon optimized and synthesized by Blue Heron biotechnologies, flanked by EcoRI and XbaI restriction sites to facilitate cloning into the pSRa mammalian expression vector. 300-19 cells, a pre-B cell line derived from a Balb/c mouse (Reth et al., *Nature,* 317:353-355 (1985)), Enzymology, Academic Press, volume 121, Florida) and Harlow et al. ("Antibodies: A Laboratory Manual"; Cold Spring Harbor Laboratory Press, New York (1988)).

TABLE 1B

The FR1-48, 49, 57, and 65 light and heavy chain CDRs are provided. The Kabat definition for heavy chain CDR2 is also given for both the murine and human antibodies.

| FR1-48 CDRs | FR1-49 CDRs | FR1-57 CDRs | FR1-65 CDRs |
|---|---|---|---|
| Light Chain | | | |
| CDR1-RASENIYSNLA (SEQ ID NO: 57) | CDR1-RASENIYTNLA (SEQ ID NO: 63) | CDR1-RASQNINNNLH (SEQ ID NO: 69) | CDR1-KASQNVGPNVA (SEQ ID NO: 75) |
| CDR2-AATNLAD (SEQ ID NO: 58) | CDR2-TASNLAD (SEQ ID NO: 64) | CDR2-YVSQSVS (SEQ ID NO: 70) | CDR2-SASYRYS (SEQ ID NO: 76) |
| CDR3-QHFWASPYT (SEQ ID NO: 59) | CDR3-QHFWVSPYT (SEQ ID NO: 65) | CDR3-QQSNSWPHYT (SEQ ID NO: 71) | CDR3-QQYNSYPYT (SEQ ID NO: 77) |
| Heavy Chain | | | |
| CDR1-TNYWMQ (SEQ ID NO: 60) | CDR1-TNYWMY (SEQ ID NO: 66) | CDR1-SSFGMH (SEQ ID NO: 72) | CDR1-TSYTMH (SEQ ID NO: 78) |
| CDR2-AIYPGNGDSR (SEQ ID NO: 61) | CDR2-AIYPGNSDTT (SEQ ID NO: 67) | CDR2-YISSGSSTIS (SEQ ID NO: 73) | CDR2-YINPISGYTN (SEQ ID NO: 79) |
| CDR3-RDGNYAAY (SEQ ID NO: 62) | CDR3-RHDYGAMDY (SEQ ID NO: 68) | CDR3-EAYGSSMEY (SEQ ID NO: 74) | CDR3-GGAYGRKPMDY (SEQ ID NO: 80) |
| Kabat BC CDR2 | Kabat HC CDR2 | Kabat HC CDR2 | Kabat HC CDR2 |
| Murine | | | |
| AIYPGNGDSRYTQKFKG (SEQ ID NO: 81) | AIYPGNSDTTYNLKFKG (SEQ ID NO: 83) | YISSGSSTISYADTVKG (SEQ ID NO: 85) | YINPISGYTNYNQKFKD (SEQ ID NO: 87) |
| Human | | | |
| AIYPGNGDSRYTQKFQG (SEQ ID NO: 82) | AIYPGNSDTTYNQKFQG (SEQ ID NO: 83) | YISSGSSTISYADSVKG (SEQ ID NO: 85) | YINPISGYTNYNQKFQG (SEQ ID NO: 87) | were transfected with the pSRa-FolR1 expression plasmid to stably express high levels of human FOLR1 on the cell surface. Standard immunization protocols known to those of skill, for example, such as those used at ImmunoGen, Inc were applied for both series. Immunized mice were boosted with antigen three days before being sacrificed for hybridoma generation. Spleens from mice was collected according to standard animal protocols, such as, for example grinding tissue between two sterile, frosted microscopic slides to obtain a single cell suspension in RPMI-1640 medium. The spleen cells were centrifuged, pelleted, washed, and fused with a murine myeloma, such as, for example P3X63Ag8.653 cells (Kearney et al., J. Immunol., 123:1548-1550 (1979)) using polyethylene glycol-1500 (Roche 783 641). The fused cells were resuspended in RPMI-1640 selection medium containing hypoxanthine-aminopterin-thymidine (HAT) (Sigma H-0262) and selected for growth in 96-well flat-bottomed culture plates (Corning-Costar 3596, 0.2 ml of cell suspension per well) at 37° C. with 5% $CO_2$. After 5 days of incubation, 0.1 ml of culture supernatant were removed from each well and replaced with 0.1 ml of RPMI-1640 medium containing hypoxanthine-thymidine (HT) supplement (Sigma H-0137). Incubation at 37° C. with 5% $CO_2$ was continued until hydridoma clones were ready for antibody screening. Other techniques of immunization and hybridoma production can also be used, including those described in Langone et al. (Eds., "Immunochemical Techniques, Part I", Methods in Example 6

Hybridoma Screening and Selection

FOLR1-300-19 cells transfected with human FOLR1 and KB cells were used in the first and second series of screenings correspondently. Culture supernatants from the hybridoma were screened by flow cytometry for secretion of mouse monoclonal antibodies that bind to FOLR1 positive cells, such as FOLR1-expressing 300-19 cells or KB cells, but not to the FOLR1 negative cells, such as non-transfected 300-19 cells. 0.1 ml of hybridoma supernatants was incubated for 3 h with either FOLR1-positive cells or the non-transfected 300-19 cells ($1 \times 10^5$ cells per sample) in 0.1 ml FACS buffer (RPMI-1640 medium supplemented with 2% normal goat serum). Then, the cells were centrifuged, pelleted, washed, and incubated for 1 hour with 0.1 ml of PE-conjugated goat anti mouse IgG-antibody (such as obtainable from, for example Jackson Laboratory, 6 µg/mL in FACS buffer). The cells were centrifuged, pelleted again, washed with FACS buffer and resuspended in 0.2 ml of PBS containing 1% formaldehyde. Cell-associated fluorescence was measured using a FACSCalibur flow cytometer with the HTS multiwell sampler or a FACS array flow cytometer and analyzed using CellQuest Pro (all from BD Biosciences, San Diego, US). Positive hybridoma clones were subcloned by limiting dilution. One subclone from each hybridoma, which showed the same reactivity against FOLR1 as the parental cells by flow cytometry, was chosen for subsequent analysis. Stable subclones were cultured and the isotype of each secreted anti-FOLR1 antibody was identified using commercial isotyping reagents (Roche 1493027). Murine antibodies were protein A purified from cleared hybridoma media as described above. These antibodies were designated FR-1 antibodies.

Example 7

Murine Monoclonal Antibody Purification

Antibodies were purified from hybridoma subclone supernatants using standard methods, such as, for example Protein A or G chromatography (HiTrap Protein A or G HP, 1 mL, Amersham Biosciences). Briefly, supernatant was prepared for chromatography by the addition of $\frac{1}{10}$ volume of 1 M Tris/HCl buffer, pH 8.0. The pH-adjusted supernatant was filtered through a 0.22 µm filter membrane and loaded onto column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of $\frac{1}{10}$ volume of 1M Tris/HCl, pH 8.0. The peak fraction(s) was dialyzed overnight twice against 1× PBS and sterilized by filtering through a 0.2 µm filter membrane. Purified antibody was quantified by absorbance at $A_{280}$.

Example 8

Binding Characterization by Flow Cytometry

Binding specificity was tested by flow cytometry using purified antibodies. FACS histograms demonstrating the binding of anti-FOLR1 to FOLR1-expressing 300-19 cells and the absence of binding to the parental 300-19 cells are shown in FIG. 4. Each antibody was incubated for 3 hours with either FOLR1-expressing 300-19 cells or the non-transfected 300-19 cells ($1 \times 10^5$ cells per sample) in 0.1 ml FACS buffer (RPMI-1640 medium supplemented with 2% normal goat serum). Then, the cells were pelleted, washed, and incubated for 1 hour with 0.1 ml of FITC-conjugated goat anti-mouse IgG-antibody (such as is obtainable from, for example Jackson Laboratory, 6 µg/mL in FACS buffer). The cells were pelleted again, washed with FACS buffer and resuspended in 200 µL of PBS containing 1% formaldehyde. Samples were acquired using a FACSCalibur flow cytometer with the HTS multiwell sampler or a FACS array flow cytometer and analyzed using CellQuest Pro (all from BD Biosciences, San Diego, US). The FACS histograms of anti-FOLR1 antibodies showed a fluorescence shift, while parental 300-19 cells did not. Also, no significant fluorescence shift was detected when either of the cell lines was incubated only with FITC conjugated goat anti-human IgG-antibody alone.

Example 9

Cloning and Sequencing of the VL and VH Regions of muFR1-21

Total cellular RNA was prepared from $5 \times 10^6$ hybridoma cells using an RNeasy kit (QIAgen) according to the manufacturer's protocol. cDNA was subsequently synthesized from total RNA using the SuperScript II cDNA synthesis kit (Invitrogen). The procedure for the first round degenerate PCR reaction on the cDNA derived from hybridoma cells was based on methods described in Wang et al. ((2000) J Immunol Methods. January 13; 233(1-2):167-77) and Co et al. ((1992) J Immunol. February 15; 148(4):1149-54). VH sequences were amplified by PCR using the following degenerate primers: EcoMH1 CTTCCGGAATTCSARGTNMAGCTGSAG-SAGTC (SEQ ID NO:50) EcoMH2 CTTCCGGAATTC-SARGTNMAGCTGSAGSAGTCWGG (SEQ ID NO:51) and BamIgG1 GGAGGATCCATAGACAGATGGGGGT-GTCGTTTTGGC (SEQ ID NO:52). VL sequences were amplified by PCR using the following degenerate primers: SacIMK GGAGCTCGAYATTGTGMTSACMCARWCT-MCA (SEQ ID NO:53) and HindKL TATAGAGCT-CAAGCTTGGATGGTGGGAAGATGGATA-CAGTTGGTGC (SEQ ID NO:54). (Mixed bases are defined as follows: N=G+A+T+C, S=G+C, Y=C+T, M=A+C, R=A+G, W=A+T).

The PCR reaction mixtures were then run on a 1% low melt agarose gel, the 300 to 400 bp bands were excised, purified using Zymo DNA mini columns, and sent to Agencourt Biosciences for sequencing. The respective 5' and 3' PCR primers were used as sequencing primers to generate the variable region cDNAs from both directions. The amino acid sequences of VH and VL regions were obtained by translating the DNA sequencing results with VectorNTI software.

To identify 5'end primer sequencing artifacts in the preliminary variable region cDNA sequences, the NCBI IgBlast site was utilized to search for the murine germline sequences from which the antibody sequence were derived. The cleaned up variable region sequences were then combined with the NCBI reference sequences for the specific antibody constant regions to assemble expected full length murine antibody sequences. The molecular weight of the expected murine Fr1-21 light and heavy chains were then calculated and compared with the mass measured by liquid chromatography/mass spectrophotometric analysis (LC/MS). The murine FR1-21 heavy chain matched the measured mass, but the light chain required a follow up sequencing effort to determine the 5' end sequence. The CD37-1LClead1 PCR primer SEQ ID NO:55) was designed to anneal to the germline linked leader sequence of the murine antibody so that this new PCR reaction would yield a complete variable region cDNA sequence, unaltered by the primers. The PCR reactions, band purifications, and sequencing were performed as described above and the new complete sequence encoded a light chain that matched the Fr1-21 light chain mass measured by LC/MS.

Example 10

Expression of Reference Antibodies

The Morphotech anti-FOLR1 antibody, MorAb-003 (Farletuzumab), amino acid sequence was obtained from the World Health Organization (WHO) International Nonproprietary Names for Pharmaceutical Substances (INN) list and was codon-optimized and synthesized by Blue Heron Biotechnology. The light chain variable region sequence is flanked by EcoRI and BsiWI restriction enzyme sites and the heavy chain variable region sequence flanked by HindIII and Apa1 restriction enzyme sites for cloning in-frame with the respective constant sequences in single chain mammalian expression plasmids. Cloning, expression and purification was carried out as described for humanized Mov19 and Fr1-21 above.

Example 11

ADCC Activity of huMov19

A lactate dehydrogenase (LDH) release assay was used to measure antibody-dependent cell mediated cytotoxicity (ADCC) of tumor cells lines using freshly isolated human natural killer (NK) cells as effector cells (e.g., Shields, J. Biol. Chem., 276(9):6591-6604 (2001)). NK cells were first isolated from human blood from a normal donor (Research Blood Components, Inc., Brighton, Mass.) using a modified protocol for the NK Isolation Kit II (Miltenyi Biotech, 130-091-152). Blood was diluted 2-fold with 1× PBS. 25 mL of diluted blood was carefully layered over 25 mL of Ficoll Paque in a 50 mL conical tube and centrifuged at 400 g for 45 min at RT. The peripheral blood mononuclear cells (PBMC) were collected from the interface, transferred into a new conical 50 mL tube, and washed once with 1× PBS. The PBMC were resuspended in 2 mL of NK-isolation buffer (1× PBS, 0.5% BSA, 2 mM EDTA), and then 500 µL of Biotin-Antibody Cocktail were added to the cell suspension. The Biotin-Antibody Cocktail contains biotinylated antibodies that bind to the lymphocytes, except for NK cells, resulting in a negative selection of NK cells. The mixture was incubated at 4° C. for 10 minutes, and then 1.5 mL of NK-isolation buffer and 1 mL of Anti-Biotin Micro Beads were added. The cell antibody mixture was incubated for another 15 minutes at 4° C. Next, cells were washed once with 50 mL of NK-isolation buffer and resuspended in 3 mL of NK-isolation buffer. Then, a MACS LS column was mounted on the autoMACS separator (Miltenyi Biotech) and pre-washed with 3 mL of NK-isolation Buffer. The cell suspension was automatically applied onto the column, washed and the effluent fraction with unlabeled NK cells was collected into a new 50 mL conical tube. The resulting NK cells were plated into 30 mL of complete RPMI media (RPMI-1640 supplemented with 5% fetal bovine serum, 1% penicillin-streptomycin, 1 mM HEPES, 1 mM Sodium Pyruvate, 1% 100× MEM non-essential Amino Acid Solution) overnight. The subsequent assay and all dilutions were carried out in RHBP medium (RPMI 1640 medium supplemented with 20 mM HEPES, pH 7.4, 0.1% BSA and 1% penicillin streptomycin). Various concentrations of antibodies in RHBP medium were aliquoted in duplicate at 50 µL/well into a round bottom 96-well plate. The target cells were resuspended at $10^6$ cells/mL in RHBP medium and added at 100 µL/well to each well containing antibody dilutions. The plate containing target cells and antibody dilutions was incubated for 30 minutes at 37° C. NK cells were then added to the wells containing the target cells at 50 µL/well. The typical ratio was about 1 target cell to 3-4 NK cells. At least the following controls were set up for each experiment: NK cells alone, target cells alone (spontaneous LDH release), target cells with NK cells (antibody independent LDH release), target cells with 10% TritonX-100 (maximum LDH release). The mixtures were incubated at 37° C. for 4 hours to allow for cell lysis. Plates were centrifuged for 10 minutes at 1200 rpm, and 100 µL of the supernatant was carefully transferred to a new flat bottom 96-well plate. LDH reaction mixture (100 µL/well) from the Cytotoxicity Detection Kit (Roche 1 644 793) was added to each well and incubated at room temperature for 5 to 30 min. The optical density of samples was measured at 490 nm ($OD_{490}$). The percent specific lysis of each sample was determined using the following formula: percent specific lysis= (sample value−spontaneous release)/(maximum release−spontaneous release)*100.

Incubation with huMov19 lead to good ADCC activity against IGROV-1 cells in the presence of human NK effector cells. ADCC activity on IGROV-1 cells was compared for huMov19, huFR-1-21, Mor003, and chTK1 (isotype contol) (FIG. 6). Treatment with 0.9 ng/ml huMov19 resulted in approximately 30% IGROV-1 cell lysis, similar to activity that was observed with the other anti-FOLR1 antibodies. ADCC activity by huMov19 had an $EC_{50}$ of 0.20 ng/mL, huFr-1-21 had an $EC_{50}$ of 0.11 ng/mL, Mor003 of 0.16 ng/mL and chTK1 did not show any activity against IGROV-1 cells.

Example 12

Preparation of Anti-FOLR1 Immunoconjugates

Preparation of huMOV19v1.6-sulfo-SPDB-DM4

The exemplary 2-sulfo-SPDB linker was dissolved in DMA. The huMOV19v1.6 antibody was incubated at 8 mg/mL with a 12 fold molar excess of 2-sulfo-SPDB linker for approximately 2 hours at 25° C. at pH 7.5. The reaction mixture was purified using a SEPHADEX™ G25F column equilibrated with 50 mM potassium phosphate buffer containing 50 mM NaCl, 2 mM EDTA, pH 6.5. The maytansinoid DM4 was dissolved in dimethylacetamide (DMA, final concentration is 5%) and a 1.7 fold molar excess compared to the linker was added drop wise to the sulfo-SPDB modified antibody. The reaction mixture was adjusted to pH 7.5 with 1 m HEPES buffer. After overnight incubation at room temperature, the conjugated antibody was purified by chromatography on SEPHADEX™ G25F equilibrated with 10 mM histidine, 250 mM glycine, 1% sucrose, pH 5.5 The number of DM4 molecules linked per antibody molecule was determined using the previously reported extinction coefficients for antibody and maytansinoid (Widdison, W C, et al. J Med Chem, 49:4392-4408 (2006)). The percentage of total free maytansinoid species were determined as described above. Conjugates with 3.5-4 DM4 molecules per huMov19v1.6 antibody were obtained with <1% present as unconjugated maytansinoid.

Preparation of huMOV19v1.6-SPP-DM1

The exemplary N-succinimidyl 4-(2-pyridyldithio)pentanoate (SPP) linker was dissolved in ethanol. The huMOV19v1.6 antibody was incubated at 8 mg/mL with a 6.5 to 6-fold molar excess of SPP linker for approximately 2 hours at room temperature in 50 mM potassium phosphate buffer (pH 6.5) containing 50 mM NaCl, 2 mM EDTA, and 5% ethanol. The SPP modified antibody was diluted 2-fold in PBS, pH 6.5 and modified with a 1.5 fold molar excess of the maytansinoid DM1 by the addition of a concentrated solution (15-30 mM) of DM1 in dimethylacetamide (DMA). The concentration of DMA was adjusted to 5% and after overnight incubation at room temperature, the conjugated antibody was purified by chromatography on SEPHADEX™ G25F equilibrated 10 mM, 250 mM glycine, 1% sucrose pH 5.5. The number of DM1 molecules linked per antibody molecule was determined using the previously reported extinction coefficients for antibody and DM1 (Liu et al., Proc. Natl. Acad. Sci. USA, 93, 8618-8623 (1996)). The percentage of free maytansinoid present after the conjugation reaction was determined by injecting 20-50 µg conjugate onto a HiSep™ column equilibrated in 25% acetonitrile in 100 mM ammonium acetate buffer, pH 7.0, and eluting in acetonitrile. The peak area of total free maytansinoid species (eluted in the gradient and identified by comparison of elution time with known standards) was measured using an absorbance detector set to a wavelength of 252 nm and compared with the peak area related to bound maytansinoid (elated in the conjugate peak in the column flow-through fractions) to calculate the percentage of total free maytansinoid species. Conjugates with 3.5-4 DM1 molecules per huMOV19v1.6 were obtained with <1% present as unconjugated maytansinoid.

Preparation of huMOV19v1.6 SPDB-DM4

The exemplary N-succinimidyl 4-(2-pyridyldithio)butanoate (SPDB) linker was dissolved in ethanol. The huMOV19v1.6 antibody was incubated at 8 mg/mL with a 5.5-5 fold molar excess of SPDB linker for approximately 2 hours at room temperature in 50 mM potassium phosphate buffer (pH 6.5) containing 50 mM NaCl, 2 mM EDTA, and 3% ethanol. The SPDB modified antibody was diluted 2-fold in PBS, pH 6.5 and modified with a 1.5 fold molar excess of the maytansinoid DM4 by the addition of a concentrated solution (15-30 mM) of DM4 in dimethylacetamide (DMA). After overnight incubation at room temperature, the conjugated antibody was purified by chromatography on SEPHADEX™ G25F equilibrated with 10 mM histidine, 250 mM glycine, 1% sucrose pH 5.5. The number of DM4 molecules linked per antibody molecule was determined using the previously reported extinction coefficients for antibody and maytansinoid (Widdison, W C, et al. J Med Chem, 49:4392-4408 (2006)). The percentage of total free maytansinoid species were determined as described above. Conjugates with 3.5-4 DM4 molecules per huMOV19v1.6antibody were obtained with <1% present as unconjugated maytansinoid.

Preparation of huMOV19v1.0-3-sulfo-mal-DM4

The NHS-3-sulfo-mal linker and DM4 were dissolved separately in DMA. The linker and DM4 thiol were mixed together in a solution of DMA containing 40% 200 mM succinate buffer, 2 mM EDTA, pH5.0 to give a molar ratio of DM4 to linker of 1.6:1 and a final concentration of DM4 equal to 10 mM. The mixture was reacted for 2 hours at 25 C. Without purification, the reaction mixture was added so that an equivalent of 9.6 molar excess of linker to antibody was added to a solution of huMOV19v1.0 antibody in phosphate buffer (pH7.5) under final conjugation conditions of 4 mg/mL antibody, 90% phosphate buffer/10% DMA pH7.5 (v/v). After an overnight incubation at room temperature, the conjugation mixture was purified by chromatography on SEPHADEX G25 equilibrated in PBS pH7.5. The huMOV19v1.0-3-sulfo-mal-DM4 was then dialyzed into a buffer containing 9.55 mM Phosphate, 139.6 mM NaCl, pH6.5. The number of DM4 molecules linked per antibody molecule was determined using the previously reported extinction coefficients for antibody and maytansinoid (Widdison, W C, et al. J Med Chem, 49:4392-4408 (2006)). The percentage of total free maytansinoid species was determined as described above. Conjugates with 3.5-4 DM4 molecules per huMOV19v1.0 antibody were obtained with <1% present as unconjugated maytansinoid.

Preparation of huMOV19v1.0-SMCC-DM1

The NHS-sulfo-SMCC linker and DM1 were dissolved separately in DMA. The linker and DM1 thiol were mixed together in a solution of DMA containing 40% 200 mM succinate buffer, 2 mM EDTA, pH5.0 to give a molar ratio of DM1 to linker of 1.2:1 and a final concentration of DM1 equal to 3.75 mM. The mixture was reacted for 75 minutes at 20° C. Without purification, the reaction mixture was added so that an equivalent of 6.4 molar excess of linker to antibody was added to a solution of huMOV19v1.0 antibody in phosphate buffer (pH7.5) under final conjugation conditions of 4 mg/mL antibody, 88% 50 mM Potassium Phosphate, 50 mM NaCl, 2 mM EDTA, pH 7.5/12% DMA pH7.5 (v/v). After 2 hour incubation at 20° C., the conjugation mixture was purified by chromatography on SEPHADEX G25 equilibrated in PBS pH7.5. The huMOV19v1.0-SMCC-DM1 was then dialyzed into a buffer containing 250 mM Glycine, 10 mM Histidine pH5.5. The number of DM1 molecules linked per antibody molecule was determined using the previously reported extinction coefficients for antibody and maytansinoid (Widdison, W C, et al. J Med Chem, 49:4392-4408 (2006)). The percentage of total free maytansinoid species was determined as described above. Conjugates with 3.5-4 DM1 molecules per huMOV19v1.0 antibody were obtained with <2.8% present as unconjugated maytansinoid.

Preparation of huMOV19v1.0-PEG4-mal-DM1

The NHS-PEG4-mal-DM1 1 step reagent was dissolved in DMA. The huMov19v1.0 antibody was incubated at 5 mg/mL with a 5.7 fold molar excess of NHS-PEG4-mal-DM1 overnight at 25° C. in 50 mM KPi, 50 mM NaCl, 2 mM EDTA, pH 7.5 and 10% DMA by volume. The reaction mixture was purified by SEPHADEX G25 column equilibrated in PBS pH7.5. The huMOV19v1.0-PEG4-mal-DM1 was dialyzed into buffer containing 250 mM Glycine, 10 mM Histidine pH5.5. The number of DM1 molecules linked per antibody molecule was determined using the previously reported extinction coefficients for antibody and maytansinoid (Widdison, W C, et al. J Med Chem, 49:4392-4408 (2006)). The percentage of total free maytansinoid species was determined as described above. Conjugates with 3.5-4 DM1 molecules per huMOV19v1.0 antibody were obtained with <1.1% present as unconjugated maytansinoid.

Example 13

Binding Affinity of Antibodies and Conjugates

Binding affinities of anti-FOLR1 antibodies and of their SPDB-DM4, PEG4Mal-DM4, SMCC-DM1, or anti-FOLR1-sulfo-SPDB-DM4 conjugates were assayed by Flow Cytometry. FOLR1-expressing SKOV3 cells were incubated with varying concentrations of anti-FOLR1 antibodies or their conjugates and processed as described above for flow cytometry analysis. Data analysis was performed using CellQuest Pro (BD Biosciences, San Diego, US) and for each sample the mean fluorescence intensity for FL1 (MFI) was exported and plotted against the antibody concentration in a semi-log plot. A dose-response curve was generated by non-linear regression and the value for the apparent equilibrium dissociation constant ($K_d$) of the test-samples for the binding to SKOV3 cells was calculated using GraphPad Prism v4 (GraphPad software, San Diego, Calif.) and presented in FIG. 5. The results demonstrate that conjugation to either DM1 or DM4 through either of the linkers used, did not notably alter the affinity of either of the antibodies (e.g., huMov19).

Example 14

In Vitro Cytotoxicity Assays

The ability of exemplary muFR1-9, muFR1-13, muFR1-22, muFR1-23, huFR1-23, muFR1-21, and huFR1-21 conjugates to inhibit cell growth was measured using in vitro cytotoxicity assays by the method described in Kovtun Y V et al. (*Cancer Res* 66: 3214-3221 (2006)). A PEG4-mal-DM4 conjugate in various concentrations was added to FOLR1-expressing KB cells in a 96 well plate at 1,000 cells per well in 100 μL in complete RPMI medium (RPMI-1640, 10% fetal bovine serum, 2 mM glutamine, 1% gentamycin, all reagents from Invitrogen). Antibodies and conjugates were diluted into complete RPMI medium using 3-fold dilution series and 100 μL were added per well. The final concentration typically ranged from $3 \times 10^{-8}$ M to $4.6 \times 10^{-12}$ M. Control wells containing cells and the medium but lacking the conjugates, and wells containing medium only were included in each assay plate. The plates were incubated from four to six days at 37° C. in a humidified atmosphere containing 5% $CO_2$. WST-8 reagent, 10% v/v (Dojindo Molecular Technologies, Gaithersburg, Md., US) was then added to the wells and the plates were incubated at 37° C. for 2-6 h. WST-8 is reduced by dehydrogenases in living cells to an orange (maximum formazan product that is soluble in tissue culture medium. The amount of formazan produced is directly proportional to the number of living cells. Plates were analyzed by measuring the absorbance at 450 nm ($A_{450}$) and at and 650 nm ($A_{650}$) in a multiwell plate reader. First, the background of cells' opalescence ($A_{650}$) was subtracted from $A_{650}$. The resulting $A*_{450}$ was then used to determine the surviving fraction of cells. Background $A*_{450}$ absorbance was that of wells with medium and WST-8 only. The surviving fraction was calculated as follows: Percent viability=100×($A*_{450}$ treated sample–$A*_{450}$ background)/($A*_{450}$ untreated sample–$A*_{450}$ background). The surviving fraction values were plotted against antibody or conjugate concentration in a semi-log plot for each treatment. From these data $IC_{50}$ values were then determined using GraphPad Prism v4 (GraphPad software, San Diego, Calif.) and presented in FIG. 5. The results shown in FIG. 5 demonstrate that all conjugates are similarly active in their cytotoxic potency against FOLR1-expressing KB cells. To further verify the specificity of the anti-FOLR1-maytansinoid conjugates towards FOLR1, their activities were evaluated in the presence of an excess of non-conjugated antibodies against KB cells. Addition of an excess of competing non-conjugated antibody to the conjugates suppressed their cytotoxicity, as seen in FIG. 7. These data indicate that the conjugates kill KB cells in an antigen-dependent manner. Additional data demonstrated that huMov19-SPDB-DM4 induced cell cycle arrest in the G2/M phase in KB cells in in vitro assays.

Example 15

In vivo Efficacy of huMov19-PEG4Mal-DM4 and huMov19-SPDB-DM4 Conjugates in Comparison with Similar Non-targeting Conjugates in a KB Xenograft Model FOLR1-targeting cleavable conjugate huMov19-SPDB-DM4 in comparison with non-targeting huC242-SPDB-DM4, and non-cleavable conjugate huMov19-PEG4-Mal-DM4 in comparison with non-targeting huC242-PEG4Mal-DM4 were tested using an established xenograft model of KB cells implanted subcutaneous into SCID mice. Mice were randomized by body weight into treatment groups and treated either singly (SPDB conjugates) on day 3 post cell inoculation, or three times weekly on days 3, 10, and 17 post cell inoculation with 5 and 10 mg/kg of a conjugate, respectively. The median tumor volume of the different treatment groups is plotted in FIG. 8. The treatments with either huMov19-SPDB-DM4, or huMov19-PEG4Mal-DM4 resulted in a decrease in median tumor volume as compared to the PBS control, while the treatments with either of the respective non-targeting conjugate did not produce any significant effect.

Example 16

In vivo Efficacy of Anti-FOLR1-PEG4Mal-DM4 Conjugates in a KB Xenograft Model

PEG4Mal-DM4 conjugates of the exemplary anti-FOLR1 antibodies huMov19, muFR-1-9, muFR-1-13, muFR-1-22, muFR-1-23, and huFR-1-21 were tested using an established xenograft model of KB cells implanted subcutaneous into SCID mice. Mice were randomized by body weight into treatment groups and treated once on day 3 post cell inoculation with 10 mg/kg of one of the conjugates listed above or with PBS only. HuMov19-PEG4Mal-DM4 was shown above to be similar to PEG4Mal-DM4 conjugates of muFR-1-9, muFR-1-13, muFR-1-22, muFR-1-23, and huFR-1-21 in its cytotoxic potency in vitro. HuMov19-PEG4Mal-DM4 and huFR-1-21-PEG4Mal-DM4 were significantly more potent in vivo than any of the other conjugates, resulting in a more pronounced decrease in median tumor volume (FIGS. 9 and 10). The potency was also demonstrated to be dose-dependent (FIG. 11) and choice of linker played a role as well (FIGS. 12 and 13).

Example 17

In vivo Efficacy of Anti-FOLR1-sulfo-SPDB-DM4 Conjugates in a Xenograft Models

Figure 16:
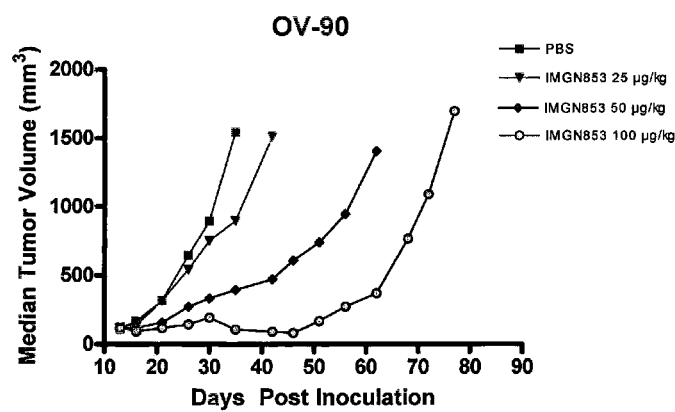

Anti-FOLR1 huMov19-sulfo-SPDB-DM4 conjugates were tested in three ovarian serous adenocarcinoma xenografts: OVCAR-3, IGROV-1, and OV-90. Each of these xenograft tumors showed FOLR1 expression levels comparable to patient tumors when measured using a calibrated immunohistochemical (IHC) staining method on formalin-fixed paraffin-embedded sections. Mice bearing established subcutaneous xenograft tumors (approximately 100 mm$^3$) were treated with a single intravenous injection of huMov19-sulfo-SPDB-DM4 conjugate at 1.2, 2.5, and 5.0 mg/kg (based on antibody concentration; FIGS. 14-16 show the concentration of the maytansanoid conjugate in μg/kg). The conjugate was active in all three models evaluated. In OVCAR-3 xenografts, the minimally efficacious dose (MED) was 1.2 mg/kg (FIG. 14). The higher dose levels were highly active, resulting in complete regressions (CR) in 4/6 and 2/6 mice in the 2.5 and 5.0 mg/kg treatment groups, respectively. Treatment with the conjugate resulted in strong anti-tumor activity in both IGROV-1 and OV-90 xenograft models, with a MED of 2.5 mg/kg, single injection (FIGS. 15 and 16). These data demonstrate the strong anti-tumor activity of huMov19-sulfo-SPDB-DM4 conjugates against ovarian xenograft tumors with FOLR1 expression levels comparable to patient tumors.

Example 18

Effect of Linkers on Immunoconjugate Efficacy

The anti-FOLR1 antibody huMov19 was linked to DM1 or DM4 via the disulfide-containing cleavable linkers SPP, SPDB, or sulfo-SPDB, or via the non-cleavable linker SMCC. The in vitro cytotoxic activities of these conjugates on KB, IGROV-1 and JEG-3 cell lines was examined. FACS analysis indicated that the KB (cervical) cells had >2,000,000 antibody binding sites per cell. The IGROV-1 (ovarian) cells had 260,000 antibody binding sites per cell, and the JEG-3 (choriocarcinoma) cells had 40,000 antibody binding sites per cell. The results of the in vitro cytotoxicity are summarized in Table 2 below. The cleavable conjugates displayed markedly greater in vitro activities compared with those of the SMCC-conjugate.

TABLE 2

Effect of immunoconjugate linkers on cytotoxicity in vitro.

| | IC$_{50}$, nM (n = 3), Ab-based | | | |
|---|---|---|---|---|
| Cells | SPP-DM1 | SPDB-DM4 | Sulfo-SPDM-DM4 | SMCC-DM1 |
| KB | 0.1 | 0.1 | 0.1 | 0.1 |
| Igrov 1 | 0.1 | 0.1 | 0.3 | 1.0 |
| Jeg3 | 0.2 | 0.2 | 3.0 | 20 |

The in vivo activities of the conjugates in FOLR1-positive KB- and OVCAR-3-tumor models were also tested. The results shown in FIG. 17 demonstrate that cleavable SPDB-DM4 and sulfo-SPDB-DM4 conjugates are more patent than non-cleavable SMCC-DM1 conjugates in vivo. In addition, among the cleavable conjugates, the SPP-DM1 conjugate was less active than either the SPDB-DM4 or sulfo-SPDB-DM4 conjugates in both xenograft models (FIG. 18). The two latter conjugates were similarly active against KB tumors, whereas the sulfo-SPDB-DM4 conjugate was more active against the OVCAR-3 model. The data obtained using the OVCAR-3 model is summarized in Table 3 below.

TABLE 3

Effect of immunoconjugate linkers on tumor size in OVCAR-3 xenograft model.

| Conjugate | Tumor over control (%) | Partial Response | Complete Response | Response |
|---|---|---|---|---|
| SPP-DM1 | 54 | 0/6 | 0/6 | Inactive |
| SPDB-DM4 | 9 | 6/6 | 1/6 | Highly active |
| Sulfo-DPDB-DM4 | 0 | 6/6 | 4/6 | Highly active |

These data demonstrate that immunoconjugates containing a cleavable linker show increased efficacy both in vitro and in vivo, and anti-FOLR1 immunoconjugates containing sulfo-SPDB are highly active in tumor models.

Example 19

In Vitro and in Vivo Efficacy of huFR1 Antibody SMCC-DM1 Conjugate

Anti-FOLR1 huFR1-48, huFR1-49, huFR1-57, and huFR1-65 were conjugated with SMCC linker and DM1 and the effects on KB cells, and in vivo using the above-described xenograft models were analyzed as described above. While each of the antibodies showed similar efficacy in the KB cell model, the huFR1-48, huFR1-49, huFR1-57, and huFR1-65 immunoconjugates showed variable, but significant, in vivo efficacy at a 200 µg/kg dose in a xenograft model system (Table 4 and FIG. 19).

TABLE 4

In vitro and in vivo efficacy of huFR1 antibody SMCC-DM1 conjugate

| Clone # | Apparent affinity (nM) | huAb-smcc-DM1 activity on KB in vitro (nM) | huAb-smcc-DM1 activity in vivo |
|---|---|---|---|
| huFR1-48 | 0.13 | 0.05 | + |
| huFR1-49 | 0.08 | 0.10 | + |
| huFR1-57 | 0.14 | 0.10 | + |
| huFR1-65 | 0.15 | 0.10 | + |
| huMov19 | 0.06 | 0.10 | ++ |

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A method of treating cancer in a subject, comprising administering a therapeutically effective amount of an antibody that specifically binds a human folate receptor to the subject, wherein the antibody comprises:
   (a) a heavy chain CDR1 comprising GYFMN (SEQ ID NO:1); a heavy chain CDR2 comprising RIHPYDGDT-FYNQKFQG (SEQ ID NO:2); and a heavy chain CDR3 comprising YDGSRAMDY (SEQ ID NO:3); and
   (b) a light chain CDR1 comprising KASQSVSF-AGTSLMH (SEQ ID NO:7); a light chain CDR2 comprising RASNLEA (SEQ ID NO:8); and a light chain CDR3 comprising QQSREYPYT (SEQ ID NO:9).

2. The method of claim 1, wherein the antibody competes with chimeric Mov19 for specific binding to a human folate receptor; and wherein the chimeric Mov19 comprises a heavy chain of SEQ ID NO:19 and a light chain of SEQ ID NO:20.

3. The method of claim 1, wherein the antibody comprises a heavy chain variable domain of SEQ ID NO:4 and a light chain variable domain of SEQ ID NO:10 or SEQ ID NO:11.

4. The method of claim 1, wherein the antibody comprises a heavy chain of SEQ ID NO:6 and a light chain of SEQ ID NO:12 or SEQ ID NO:13.

5. The method of claim 1, wherein the antibody comprises a heavy chain encoded by the plasmid DNA deposited with the ATCC on Apr. 7, 2010 and having ATCC deposit no. PTA-10772 and a light chain encoded by the plasmid DNA deposited with the ATCC on Apr. 7, 2010 and having ATCC deposit no. PTA-10773 or 10774.

6. The method of claim 1, wherein the cancer is selected from the group consisting of: ovarian cancer, breast cancer, uterine cancer, endometrial cancer, pancreatic cancer, renal cancer, and lung cancer.

7. The method of claim 6, wherein the cancer is ovarian cancer.

8. The method of claim 6, wherein the cancer is lung cancer.

9. The method of claim 6, wherein the cancer is endometrial cancer.

10. The method of claim 1, further comprising administering a second anti-cancer agent to the subject.

11. The method of claim 10, wherein said second anti-cancer agent is a chemotherapeutic agent.

12. A method of inhibiting cancer growth in a subject, comprising administering a therapeutically effective amount of an immunoconjugate having the formula (A) -(L)-(C) to the subject, wherein:
   (A) is an antibody or antigen binding fragment thereof that specifically binds a human folate receptor;
   (L) is a linker; and
   (C) is a cytotoxic agent;
   wherein (L) links (A) to (C),
   wherein the antibody or antigen binding fragment thereof comprises:
   (a) a heavy chain CDR1 comprising GYFMN (SEQ ID NO:1); a heavy chain CDR2 comprising RIHPYDGDTFYNQKFQG (SEQ ID NO:2); and a heavy chain CDR3 comprising YDGSRAMDY (SEQ ID NO:3); and
   (b) a light chain CDR1 comprising KASQSVSFAGTSLMH (SEQ ID NO:7); a light chain CDR2 comprising RASNLEA (SEQ ID NO:8); and a light chain CDR3 comprising QQSREYPYT (SEQ ID NO:9).

13. The method of claim 12, wherein the antibody or antigen binding fragment thereof comprises a heavy chain variable domain of SEQ ID NO:4 and a light chain variable domain of SEQ ID NO:10 or SEQ ID NO:11.

14. The method of claim 12, wherein the antibody comprises a heavy chain of SEQ ID NO:6 and a light chain of SEQ ID NO:12 or SEQ ID NO:13.

15. The method of claim 12, wherein the antibody comprises a heavy chain encoded by the plasmid DNA deposited with the ATCC on Apr. 7, 2010 and having ATCC deposit no. PTA-10772 and a light chain encoded by the plasmid DNA deposited with the ATCC on Apr. 7, 2010 and having ATCC deposit no. PTA-10773 or PTA-10774.

16. The method of claim 12, wherein the cancer is selected from the group consisting of: ovarian cancer, breast cancer, uterine cancer, endometrial cancer, pancreatic cancer, renal cancer, and lung cancer.

17. The method of claim 16, wherein the cancer is ovarian cancer.

18. The method of claim 16, wherein the cancer is lung cancer.

19. The method of claim 16, wherein the cancer is endometrial cancer.

20. The method of claim 12, further comprising administering a second anti-cancer agent to the subject.

21. The method of claim 20, wherein said second anti-cancer agent is a chemotherapeutic agent.

22. The method of claim 12, wherein (L) is a linker selected from the group consisting of a cleavable linker, a non-cleavable linker, a hydrophilic linker, and a dicarboxylic acid based linker.

23. The method of claim 12, wherein (L) is a linker selected from the group consisting of N-succinimidyl 4-(2-pyridyldithio)pentanoate (SPP) or N-succinimidyl 4-(2-pyridyldithio)-2-sulfopentanoate (sulfo-SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide).

24. The method of claim 23, wherein (L) is N-succinimidyl 4-(2-pyridyldithio)butanoate (SPDB) or N-succinimidyl 4-(2-pyridyldithio)-2-sulfobutanoate (sulfo-SPDB).

25. The method of claim 12, wherein (C) is a cytotoxic agent selected from the group consisting of a maytansinoid, benzodiazepine, taxoid, CC-1065, duocarmycin, calicheamicin, dolastatin, auristatin, tomaymycin, and leptomycin or a prodrug of the cytotoxic agent.

26. The method of claim 25, wherein (C) is a maytansinoid.

27. The method of claim 12, wherein (C) is N(2')-deacetyl-N(2')-(3-mercapto-1-oxopropyl)-maytansine or N(2')-deacetyl-N(2')-(4-mercapto-4-methyl-1-oxopentyl)-maytansine.

28. The method of claim 12, wherein the immunoconjugates have an average of about 3 to about 4 (C) per (A).

29. The method of claim 12, wherein the immunoconjugate comprises:
   (A) a humanized antibody comprising the heavy chain variable domain of SEQ ID NO:4, and the light chain variable domain of SEQ ID NO:10 or SEQ ID NO:11;
   (L) N-succinimidyl 4-(2-pyridyldithio)-2-sulfobutanoate (sulfo-SPDB); and
   (C) N(2')-deacetyl-N(2')-(4-mercapto-4-methyl-1-oxopentyl)-maytansine.

30. A method of treating cancer in a subject, comprising administering a therapeutically effective amount of an immunoconjugate having the formula (A) -(L)-(C) to the subject, wherein:
   (A) comprises a humanized antibody or antigen binding fragment thereof that specifically binds a human folate receptor;
   (L) comprises the linker N-succinimidyl 4-(2-pyridyldithio)-2-sulfobutanoate (sulfo-SPDB); and
   (C) comprises the cytotoxic agent N(2')-deacetyl-N(2')-(4-mercapto-4-methyl-1-oxopentyl)-maytansine;
   wherein (L) links (A) to (C);
   wherein the antibody or antigen binding fragment thereof comprises:
   (a) a heavy chain CDR1 comprising GYFMN (SEQ ID NO:1); a heavy chain CDR2 comprising RIHPYDGDTFYNQKFQG (SEQ ID NO:2); and a heavy chain CDR3 comprising YDGSRAMDY (SEQ ID NO:3); and
   (b) a light chain CDR1 comprising KASQSVSFAGTSLMH (SEQ ID NO:7); a light chain CDR2 comprising RASNLEA (SEQ ID NO:8); and a light chain CDR3 comprising QQSREYPYT (SEQ ID NO:9).

31. The method of claim 30, wherein the antibody or antigen binding fragment thereof comprises a heavy chain variable domain of SEQ ID NO:4 and a light chain variable domain of SEQ ID NO:10 or SEQ ID NO:11.

32. The method of claim 31, wherein the antibody or antigen binding fragment thereof comprises the light chain variable domain of SEQ ID NO:11.

33. The method of claim 30, wherein the antibody comprises a heavy chain of SEQ ID NO:6 and a light chain of SEQ ID NO:12 or SEQ ID NO:13.

34. The method of claim 30, wherein the cancer is selected from the group consisting of: ovarian cancer, breast cancer, uterine cancer, endometrial cancer, pancreatic cancer, renal cancer, and lung cancer.

35. The method of claim 34, wherein the cancer is ovarian tumor.

36. The method of claim 34, wherein the cancer is lung cancer.

37. The method of claim 34, wherein the cancer is endometrial cancer.

38. The method of claim 30, further comprising administering a second anti-cancer agent to the subject.

39. The method of claim 38, wherein said second anti-cancer agent is a chemotherapeutic agent.

40. The method of claim 30, wherein the immunoconjugates have an average of about 3 to about 4 (C) per (A).

41. The method of claim 12, wherein the cancer is brain cancer, and wherein the immunoconjugate is administered intracranially.

42. The method of claim 41, wherein the immunoconjugate is administered intrathecally or intraventricularly.

43. The method of claim 30, wherein the cancer is brain cancer, and wherein the immunoconjugate is administered intracranially.

44. The method of claim 43, wherein the immunoconjugate is administered intrathecally or intraventricularly.

* * * * *

UNITED STATES PATENT AND TRADEMARK OFFICE
CERTIFICATE OF CORRECTION

Page 1 of 1

PATENT NO.         : 9,133,275 B2
APPLICATION NO.    : 13/800835
DATED              : September 15, 2015
INVENTOR(S)        : Ab et al.

It is certified that error appears in the above-identified patent and that said Letters Patent is hereby corrected as shown below:

In the specification

"AIYPGNSDTTYNLKFKG (SEQ ID NO: 83)" should be corrected to read "AIYPGNSDTTYNLKFKG (SEQ ID NO: 130)"    In columns 63-64, line 33 (Table 1B)

"YISSGSSTISYADTVKG (SEQ ID NO: 85)" should be corrected to read "YISSGSSTISYADTVKG (SEQ ID NO: 84)"    In columns 63-64, line 33 (Table 1B)

"YINPISGYTNYNQKFKD (SEQ ID NO: 87)" should be corrected to read "YINPISGYTNYNQKFKD (SEQ ID NO: 86)"    In columns 63-64, line 33 (Table 1B)

In the claims

"SEQ IS NO:20" should be corrected to read "SEQ ID NO:20"    In column 179, line 64 (Claim 2)

"A method of inhibiting cancer growth in a subject" should be corrected to read "A method of treating cancer in a subject"    In column 181, line 5 (Claim 12)

"(A) –(L)-(C)" should be corrected to read "(A)-(L)-(C)"    In column 181, line 7 (Claim 12)

"(A) –(L)-(C)" should be corrected to read "(A)-(L)-(C)"    In column 182, line 28 (Claim 30)

"ovarian tumor" should be corrected to read "ovarian cancer"    In column 182, lines 62-63 (Claim 35)

Signed and Sealed this
Twenty-second Day of March, 2016

Michelle K. Lee
*Director of the United States Patent and Trademark Office*